United States Patent [19]

Döbeli et al.

[11] Patent Number: 5,310,663

[45] Date of Patent: May 10, 1994

[54] AFFINITY PEPTIDES

[75] Inventors: Heinz Döbeli, Ziefen; Bernhard Eggimann, Basel, both of Switzerland; Reiner Gentz, Rheinfelden, Fed. Rep. of Germany; Erich Hochuli, Arisdorf, Switzerland; Dietrich Stüber, Grenzach-Wyhlen, Fed. Rep. of Germany

[73] Assignee: Hoffman-La Roche Inc., Nutley, N.J.

[21] Appl. No.: 80,043

[22] Filed: Jun. 18, 1993

Related U.S. Application Data

[62] Division of Ser. No. 158,962, Feb. 22, 1988.

[30] Foreign Application Priority Data

Oct. 3, 1987 [CH] Switzerland .......................... 895/87

[51] Int. Cl.⁵ .................. C12N 15/00; C12P 21/02
[52] U.S. Cl. ................... 435/69.7; 435/240.1; 435/320.1; 536/23.1; 530/413
[58] Field of Search ............... 536/23.1; 435/69.7, 435/240.1, 320.1; 530/413

[56] References Cited

U.S. PATENT DOCUMENTS 4,569,794 2/1986 Smith et al. .................. 260/113
4,877,830 10/1989 Dobeli et al. .................. 525/54.3

FOREIGN PATENT DOCUMENTS 0161937 11/1985 European Pat. Off. .

OTHER PUBLICATIONS

Germino et al., Proc. Nat'l. Acad. sci., USA 80:6848 (1983).
Hopp et al., European Pat. Appl. Pub. No. 150261 (1985).
Nelsson et al., Nucleic Acids Res. 13: 1151 (1985).

Primary Examiner—Robert J. Hill, Jr.
Assistant Examiner—Sally P. Teng
Attorney, Agent, or Firm—George M. Gould; William H. Epstein

[57] ABSTRACT

Fusion proteins and a process for their purification by means of metal chelate affinity chromatography on NTA resins are provided by this invention.

11 Claims, 58 Drawing Sheets

|      | 10         | 20         | 30         | 40         | 50         |
|------|------------|------------|------------|------------|------------|
| 0    | CCTCGAGGCT | GGCATCCCTA | ACATATCCGA | ATGGTTACTT | AAACAACGGA |
| 50   | GGACTAGCGT | ATCCCTTCGC | ATAGGGGTTG | AGTTAGATAA | AGTATATGCT |
| 100  | GAACTTCTT  | CTTTGCTCAA | AGAATCATAA | AAAATTTATT | TGCTTTCAGG |
| 150  | AAAATTTTTC | TGTATAATAG | ATTCAAATTG | TGAGCGGATA | ACAATTTGAA |
| 200  | TTCATTAAAG | AGGAGAAATT | AAGCATGCGA | GGATCCGGCA | TCATGGTTCG |
| 250  | ACCATTGAAC | TGCATCGTCG | CCGTGTCCCA | AAATATGGGG | ATTGGCAAGA |
| 300  | ACGGAGACCT | ACCCTGGCCT | CCGCTCAGGA | ACGAGTTCAA | GTACTTCCAA |
| 350  | AGAATGACCA | CAACCTCTTC | AGTGGAAGGT | AAACAGAATC | TGGTGATTAT |
| 400  | GGGTAGGAAA | ACCTGGTTCT | CCATTCCTGA | GAAGAATCGA | CCTTTAAAGG |
| 450  | ACAGAATTAA | TATAGTTCTC | AGTAGAGAAC | TCAAAGAACC | ACCACGAGGA |
| 500  | GCTCATTTTC | TTGCCAAAAG | TTTGGATGAT | GCCTTGAGAC | TTATTGAACA |
| 550  | ACCGGAATTG | GCAAGTAAAG | TAGACATGGT | TTGGATAGTC | GGAGGCAGTT |
| 600  | CTGTTTACCA | GGAAGCCATG | AATCAACCAG | GCCACCTTAG | ACTCTTTGTG |
| 650  | ACAAGGATCA | TGCCAGGAAT | TGAAAGTGAC | ACGTTTTTCC | CAGAAATTGA |
| 700  | TTTGGGAAA  | TATAAACTTC | TCCCAGAATA | CCCAGGCGTC | CTCTCTGAGG |
| 750  | TCCAGGAGGA | AAAAGGCATC | AAGTATAAGT | TTGAAGTCTA | CGAAGAAA   |
| 800  | GACTAACAGG | AAGATGCTTT | CAAGTTCTCT | GCTCCCCTCC | TAAAGCTATG |
| 850  | CATTTTTATA | AGACCATGGG | ACTTTTGCTG | GCTTTAGATC | CGCGCAAGCT |
| 900  | TGGACTCCTG | TTGATAGATC | CAGTAATGAC | CTCAGAACTC | CATCTGGATT |
| 950  | TGGTCAGAAC | GCTCGGTTGC | CGCCGGGCGT | TTTTTATTGG | TGAGAATCCA |
| 1000 | AGCTAGCTTG | GCCAGATTTT | CAGGAGCTAA | GGAAGCTAAA | ATGGAGAAAA |
| 1050 | AAATCACTGG | ATATACCACC | CAGGAGCTAA | CCCAATGGCA | TCGTAAAGAA |
| 1100 | CATTGTGAGG | CATTTCAGTC | AGTTGCTCAA | TGTACCTATA | ACCAGACCGT |
| 1150 | TCAGCTGGAT | ATTACGGCCT | TTTAAAGAC  | CGTAAAGAAA | AATAAGCACA |

FIG. 2A

|      | 10         | 20         | 30         | 40         | 50         |
|------|------------|------------|------------|------------|------------|
| 1200 | AGTTTTATCC | GGCCTTTATT | CACATTCTTG | CCCGCCTGAT | GAATGCTCAT |
| 1250 | CCGGAATTTC | GTATGGCAAT | GAAAGACGGT | GAGCTGGTGA | TATGGGATAG |
| 1300 | TGTTCACCCT | TGTTACACCG | TTTTCCATGA | GCAAACTGAA | ACGTTTTCAT |
| 1350 | CGGTGTGGAG | TGAATACCAC | GACGATTTCC | GGCAGTTTCT | ACACATATAT |
| 1400 | TCGCAAGATC | TGGCCGTGTTA | CGGTGAAAAC | CTGGCCTATT | TCCCTAAAGG |
| 1450 | GTTTATTGAG | AATATGTTTT | TCGTCTCAGC | CAATCCCTGG | GTGAGTTTCA |
| 1500 | CCAGTTTTGA | TTTAAACGTG | GCCAATATGG | ACAACTTCTT | CGCCCCCGTT |
| 1550 | TTCACCATGG | GCAAATATTA | TACGCAAGGC | GACAAGGTGC | TGATGCCGGT |
| 1600 | GGCGATTCAG | GTTCATCATG | CCGTCTGTGA | TGGCGTCCAT | GTCGGCAGAA |
| 1650 | TGCTTAATGA | ATTACAACAG | TACTGCGATG | AGTGCAGGG  | CGGGGCGTAA |
| 1700 | TTTTTTAAG  | GCAGTTATTG | GTGCCCTTAA | ACGCCTGGGG | TAATGACTCT |
| 1750 | CTAGCTTGAG | GCATCAAATA | AACGAAAGG  | CTCAGTCGAA | AGACTGGGCC |
| 1800 | TTTCGTTTA  | TCTGTTGTTT | GTCGGTGAAC | GCTCTCCTGA | GTAGGACAAA |
| 1850 | TCCGCCGCTC | TAGAGC     |            |            |            |

|—— 2068                    pBR322 ——————————————— A         |
|                                                  4358      |

FIG. 2B

|      | 10         | 20         | 30         | 40         | 50         |
|------|------------|------------|------------|------------|------------|
| 0    | CCTCGAGGCT | GGCATCCCTA | ACATATCCGA | ATGGTTACTT | AAACAACGGA |
| 50   | GGACTAGCGT | ATCCCTTCGC | ATAGGGTTTG | AGTTAGATAA | AGTATATGCT |
| 100  | GAACTTTCTT | CTTTGCTCAA | AGAATCATAA | AAATTTATT  | TGCTTTCAGG |
| 150  | AAAATTTTTC | TGTATAATAG | ATTCAAATTG | TGAGCGGATA | ACAATTTGAA |
| 200  | TTCATTAAAG | AGGAGAAAT  | AACTATAGGG | GGATCCGTCG | CCCTGCAGCC |
| 250  | AAGCTTGGCG | AGATTTTCAG | GAGCTAAGGA | AGCTAAAATG | GAGAAAAAA  |
| 300  | TCACTGGATA | TACCACCGT  | GATATATCCC | AATGGCATCG | TAAAGAACAT |
| 350  | TTTGAGGCAT | TCAGTCAGT  | TGCTCAATGT | ACCTATAACC | AGACCGTTCA |
| 400  | GCTGGATATT | ACGGCCTTT  | TAAAGACCGT | AAAGAAAAT  | AGCACAAGT  |
| 450  | TTATCCGGC  | CTTATTCAC  | ATTCTTGCCC | GCCTGATGAA | TGCTCATCCG |
| 500  | GAATTCGTA  | TGGCAATGAA | AGACGGTGAG | CTGGTATAT  | GGGATAGTGT |
| 550  | TCACCCTTGT | TACACCTTTT | TCCATGAGCA | AACTGAAACG | TTTTCATCGC |
| 600  | TCTGGAGTGA | ATACCACGAC | GATTTCCGGC | AGTTTCTACA | CATATATCG  |
| 650  | CAAGATGTGG | CGTGTTACGG | TGAAAACCTG | GCCTATTTCC | CTAAAGGTT  |
| 700  | TATTGAGAAT | ATGTTTTTCG | TCTCAGCCAA | TCCCTGGGTG | AGTTTCACCA |
| 750  | GTTTTGATT  | AACGTGGCC  | AATATGGACA | ACTTCTTCGC | CCCCGTTTC  |
| 800  | ACCATGGGCA | AATATTATAC | GCAAGGCGAC | AAGGTGCTGA | TGCCGCTGGC |
| 850  | GATTCAGGTT | CATCATGCCG | TCTGTGATGG | CTTCCATGTC | GGCAGAATGC |
| 900  | TAATGAAT   | ACAACAGTAC | TGCGATGAGT | GGCAGGGCGG | GGCGTAATT  |
| 950  | TTTAAGGCA  | GTTATTGGTG | CCCTTAAACG | CCTGGGGTAA | TGACTCTCTA |
| 1000 | GCTTGAGGCA | TCAAATAAAA | CGAAAGGCTC | AGTCGAAAGA | CTGGGCCTTT |
| 1050 | CGTTTTATCT | GTGTTTGTC  | GGTGAACGCT | CTCCTGAGTA | GGACAAATCC |
| 1100 | GCCGCTCTAG | AGCTGCCTCG | CGCGTTTCGG | TGATGACGGT | GAAAACCTCT |
| 1150 | GACACATGCA | GCTCCCGGAG | ACGGTCACAG | CTTGTCTGTA | AGCGGATGCC |

FIG. 4A

```
        10          20          30          40          50
1200 GGGAGCAGAC AAGCCCGTCA GGGCGCGTCA GCGGGTGTTG GCGGGTGTCG
1250 GGGCGGCAGCC ATGACCCAGT CACGTAGCGA TAGCGGAGTG TATACTGACT
1300 TAACTATGCG GCATCAGAGC AGATTGTACT GAGAGTGCAC CATATGCGGT
1350 GTGAAATACC GCACAGATGC GTAAGGAGAA AATACCGCAT CAGGCGCTCT
1400 TCCGCTTCCT CGCTCACTGA CTCGCTGCGC TCGGTCGTTC GGCTGCGGCG
1450 AGCGGTATCA GCTCACTCAA AGGCGGTAAT ACGGTTATCC ACAGAATCAG
1500 GGGATAACGC AGGAAAGAAC ATGTGAGCAA AAGGCCAGCA AAGGCCAGG
1550 AACCGTAAAA AGGCCGCGTT GCTGGCGTTT TTCCATAGGC TCCGCCCCC
1600 TGACGAGCAT CACAAAATC GACGCTCAAG TCAGAGGTGG CGAAACCCGA
1650 CAGGACTATA AAGATACCAG GCGTTTCCCC CTGGAAGCTC CCTCGTGCGC
1700 TCTCCTGTTC CGACCCTGCC GCTTACCGGA TACCTGTCCG CCTTTCTCCC
1750 TTCGGGAAGC GTGGCGCTTT CTCAATGCTC ACGCTGTAGG TATCTCAGTT
1800 CGGTGTAGGT CGTTCGCTCC AAGCTGGGCT GTGTGCACGA ACCCCCCGTT
1850 CAGCCCGACC GCTGCGCCTT ATCCGGTAAC TATCGTCTTG AGTCCAACCC
1900 GGTAAGACAC GACTTATCGC CACTGGCACG AGCCACTGGT AACAGGATTA
1950 GCAGAGCGAG GTATGTAGGC GGTGCTACAG AGTTCTTGAA GTGGTGGCCT
2000 AACTACGGCT ACACTAGAAG GACAGTATTT GGTATCTGCG CTCTGCTGAA
2050 GCCAGTTACC TTCGGAAAAA GAGTTGGTAG CTCTTGATCT GGCAAACAAA
2100 CCACCGCTGG TAGCGGTGGT TTTTTGTTT GCAAGCAGCA GATTACGCGC
2150 AGA(AAAAG GATCTCAAGA AGATCCTTTG ATCTTTTCTA AGGGTCTGA
2200 CGCTCAGTGG AACGAAAACT CACGTTAAGG GATTTTGGTC ATGAGATTAT
2250 CAAAAAGGAT CTTCACCTAG ATCCTTTTAA ATTAAAAATG AAGTTTTAAA
2300 TCAATCTAAA GTATATATGA GTAAACTTGG TCTGACAGTT ACCAATGCTT
2350 AATCAGTGAG GCACCTATCT CAGCGATCTG TCTATTTCGT TCATCCATAG
2400 TTGCCTGACT CCCGTCGTG TAGATAACTA CGATACGGGA GGGCTTACCA
2450 TCTGGCCCCA GTGCTGCAAT GATACCGCGA GACCCACGCT CACCGGCTGG
2500 AGATTTATCA GCAATAAACC AGCCAGCCGG AAGGGCCGAG CGCAGAAGTG
2550 GTCCTGCAAC TTTATCCGCC TCCATCCAGT CTATTAATTG TTGCCGGGAA
```

FIG. 4B

|  | 10 | 20 | 30 | 40 | 50 |
|---|---|---|---|---|---|
| 2600 | GCTAGAGTAA | GTAGGTCGCC | AGTTAATAGT | TTGCGCAACG | TTGTTGCCAT |
| 2650 | TGCTACAGGC | ATCGTGGTGT | CACGCTCGTC | GTTTGGTATG | GCTTCATTCA |
| 2700 | GCTCGCGTTC | CCAACGATCA | AGGCGAGTTA | CATGATCCCC | CATGTTGTGC |
| 2750 | AAAAAGCGG | TTAGCTCCTT | CGGTCCTCCG | ATCGTTGTCA | GAAGTAAGTT |
| 2800 | GGCCGCAGTG | TTATCACTCA | TGGTTATGGC | AGCACTGCAT | AATTCTCTTA |
| 2850 | CTGTCATGCC | ATCCGTAAGA | TGCTTTTCTG | TGACTGGTGA | GTACTCAACC |
| 2900 | AAGTCATTCT | GAGAATAGTG | TATGCGGGCA | CCGAGTTGCT | CTTGCCCGGC |
| 2950 | GTCAATACGG | GATAATACCG | CGCCACATAG | CAGAACTTTA | AAAGTGCTCA |
| 3000 | TCATTGGAAA | ACGTTCTTCG | GGGCGAAAAC | TCTCAAGGAT | CTTACCGCTG |
| 3050 | TTGAGATCCA | GTTCGATGTA | ACCCACTCGT | GCACCCAACT | GATCTTCAGG |
| 3100 | ATCTTTTACT | TTCACCAGCG | TTTCTGGGTG | AGCAAAAACA | GGAAGGCAAA |
| 3150 | ATGCCGCAAA | AAAGGGAATA | AGGGCGACAC | GGAAATGTTG | AATACTCATA |
| 3200 | CTCTTCCTTT | TTCAATATTA | TTGAAGCATT | TATCAGGGTT | ATTGTCTCAT |
| 3250 | GAGCGGATAC | ATATTTGAAT | GTATTTAGAA | AAATAAACAA | ATAGGGGTTC |
| 3300 | CGCGCACATT | TCCCCGAAAA | GTGCCACCTG | ACGTCTAAGA | AACCATTATT |
| 3350 | ATCATGACAT | TAACCTATAA | AAATAGGCGT | ATCACGAGGC | CCTTTCGTCT |
| 3400 | TCA | | | | |

FIG. 4C

```
              10         20         30         40         50
   1  CTCGAGAAAT CATAAAAAAT TTATTGCTT  TGTGAGCGGA TAACAATTAT
  51  AATAGATTCA ATTGTGAGCG GATAACAATT TCACACAGAA TTCATTAAAG
 101  AGGAGAAATT AACTATGAGA GGATCCGGCA TCATGGTTCG ACCATTGAAC
 151  TGCATCGTCG CCGTGTCCCA AAATATGGGG ATTGGCAAGA ACGGAGACCT
 201  ACCCTGGCCT CCGTCAGGA  ACGAGTCAA  GTACTCCAA  AGAATGACCA
 251  CAACCTCTTC AGTGGAAGGT AAACAGAATC TGGTGATTAT GGGTAGGAA
 301  ACCTGGTTCT CCATTCCTGA GAAGATCGA  CCTTTAAAGG ACAGAATTAA
 351  TATAGTTCTC AGTAGAGAAC TCAAAGAACC ACCACGAGGA GCTCATTTTC
 401  TTGCCAAAG  TTTGGATGAT GCCTTAAGAC TTATTGAACA ACCGGAATTG
 451  GCAAGTAAAG TAGACATGGT TGGATAGTC  GGAGGCAGTT CTGTTTACCA
 501  GGAAGCCATG AATCAACCAG GCCACTTAG  ACTCTTTGTG ACAAGGATCA
 551  TGCACCAAT  TGAAGTGAC  AGTTTTTCC  CAGAAATTGA TTGGGAAA
 601  TATAAACTTC TCCCAGAATA CCCAGGCCGTC CTCTCTGAGG TCCAGGAGGA
 651  AAAAGGCATC AGTATAAAGT TGAAGTCTA  CGAGAACAAA GGTTCCAGAT
 701  CTGTTAACCT AGTTAACAG  GAAGATGCTT TCAAGTTCTC TGCTCCCCTC
 751  CTAAAGCTAT GCATTTTAT  AAGACCATGG GACTTTTGCT GGCTTTAGAT
 801  CCGGCCAAGC TTGGACTCCT GTTGATAGAT CCAGTAATGA CCTCAGAACT
 851  CCATCTGGAT TTGTTCAGAA CGCTCGGTTG CCGCCGGGCG TTTTTATTG
 901  GTGAGAATCC AAGCTAGCTT GGCGAGATTT TCAGGAGCTA AGGAAGCTAA
 951  AATGGAGAAA AAAATCACTG GATATACCAC CGTTGATATA TCCCAATGCC
1001  ATCGTAAAGA ACATTTTGAG GCATTTCAGT CAGTTGCTCA ATGTACCTAT
1051  AACCAGACCG TTCAGCTGGA TATTACGGCC TTTTTAAAGA CCGTAAAGAA
1101  AATAAGCAC  AGTTTTATC  CGGCCTTAT  TCACATTCTT GCCCGCCTGA
1151  TGAATGCTCA TCCGGAATTT CGTATGGCAA TGAAAGACGG TGAGCTGGTG
```

FIG. 6A

| | | | |
|---|---|---|---|
| 1201 | ATATGGGATA | GTGTTCACCC | TTGTTACACC | AGCAAACTGA |
| 1251 | AACGTTTTCA | TCGCCAAGAT | GTGAATACCA | CGGCAGTTTC |
| 1301 | TACACATATA | TTCGCAAGAT | GTGGCGTGTT | CTTGGCCTAT |
| 1351 | TTCCCTAAAG | GGTTTATTGA | GAATATGTTT | CCAATCCCTG |
| 1401 | GGTGAGTTTC | ACCAGTTTTG | ATTTAAACGT | GACAACTTCT |
| 1451 | TCGCCCCCGT | TTTCACCATG | GGCAAATATT | CGACAAGGTG |
| 1501 | CTGATGCCGC | TGGCGATTCA | GGTTCATCAT | ATGGCTTCCA |
| 1551 | TGTCGGCAGA | ATGCTTAATG | AATTACAACA | GAGTGGCAGG |
| 1601 | GCGGGGCGTA | ATTTTTTAA | GGCAGTTATT | AACGCTGGG |
| 1651 | GTAATGACTC | TCTAGCTTGA | GGCATCAAAT | GCTCAGTCGA |
| 1701 | AAGACTGGGC | CTTTCGTTT | ATCTGTTGTT | CGCTCTCCTG |
| 1751 | AGTAGGACAA | ATCCGCCCGCT | CTAGAGCTGC | TCGGTGATGA |
| 1801 | CGGTGAAAAC | CTCTGACACA | TGCAGCTCCC | ACAGCTTGTC |
| 1851 | TGTAAGCGGA | TGCCGGGAGC | AGACAAGCTC | GTCAGCGGGT |
| 1901 | GTTGGCGGGT | GTCGGGGCGC | AGCCATGACC | GCGATAGCGG |
| 1951 | AGTGTATACT | GGCTTAACTA | TGCGGCATCA | TACTGAGAGT |
| 2001 | GCACCATATG | CGGTGTGAAA | TACCGCACAG | AGAAATACC |
| 2051 | GCATCAGGCG | CTCTTCCGCT | TCCTCGCTCA | GCGCTCGGTC |
| 2101 | TGTCGGCTGC | GCCGAGCGGT | ATCAGCTCAC | TAATACGGT |
| 2151 | ATCCACAGAA | TCAGGGGATA | ACGCAGGAAA | GAACATGTGA |
| 2201 | AGCAAAAGGC | CAGGAACCGT | AAAAAGGCCG | CGTTGCTGGC |
| 2251 | AGGCTCCGCC | CCCCTGACGA | GCATCACAAA | GTTTTCCAT |
| 2301 | GTGGCGAAAC | CCACAGGACT | TATAAAGATA | CAAGTCAGAG |
| 2351 | GCTCCCTCGT | GCGCTCTCCT | GTTCCGACCC | CCCCTGAA |
| 2401 | TCCGCCTTTC | TCCCTTCGGG | AAGCGTGGCG | CGGATACCTG |
| 2451 | TAGGTATCTC | AGTTCGGTGT | AGGTCGTTCG | GCTCACGCTG |
| 2501 | ACGAACCCCC | CGTTCAGCCC | GACCGCTGCG | GGCTGTGTGC |
| | | | TAACTATCGT |

FIG. 6B

| | | | | |
|---|---|---|---|---|
|2551|CTGAAGTCCA|ACCCGGTAAG|ACACGACTTA|TCGCCACTGG|CAGCAGCCAC|
|2601|TGGTAACAGG|ATTAGCAGAG|CGAGGTATGT|AGGCGGTGCT|ACAGAGTTCT|
|2651|TGAAGTGGTG|GCCTAACTAC|GGCTACACTA|GAAGGACAGT|ATTTGGTATC|
|2701|TGCGCTCTGC|TGAAGCCAGT|TACCTTCGGA|AAAAGAGTTG|GTAGCTCTTG|
|2751|ATCCGGCAAA|CAAACCACCG|CTGGTAGCGG|TGGTTTTTTT|GTTTGCAAGC|
|2801|AGCAGATTAC|GCGCAGAAAA|AAAGGATCTC|AAGAAGATCC|TTTGATCTTT|
|2851|TCTACGGGGT|CTGACGCTCA|GTGGAACGAA|AACTCACGTT|AAGGGATTTT|
|2901|GGTCATGAGA|TTATCAAAA|GGATCTTCAC|CTAGATCCTT|TAAATTAAA|
|2951|AATGAAGTTT|TAAATCAATC|TAAAGTATAT|ATGAGTAAAC|TTGGTCTGAC|
|3001|AGTTACCAAT|GCTTAATCAG|TGAGGCACCT|ATCTCAGCGA|TCTGTCTATT|
|3051|TCGTTCATCC|ATAGTTGCCT|GACTCCCCGT|CGTGTAGATA|ACTACGATAC|
|3101|GGGAGGGCTT|ACCATCTGGC|CCCAGTGCTG|CAATGATACC|GCGAGACCCA|
|3151|CGCTCACCGG|CTCCAGATTT|ATCAGCAATA|AACCAGCCAG|CCGGAAGGGC|
|3201|CGAGCGCAGA|AGTGGTCCTG|CAACTTTATC|CGCCTCCATC|CAGTCTATTA|
|3251|ATTGTTGCCG|GGAAGCTAGA|GTAAGTAGTT|CGCCAGTTAA|TAGTTTGCGC|
|3301|AACGTTGTTG|CCATTGCTAC|AGGCATCGTG|GTGTCACGCT|CGTCGTTTGG|
|3351|TATGGCTTCA|TTCAGCTCCG|GTTCCCAACG|ATCAAGGCGA|GTTACATGAT|
|3401|CCCCCATGTT|GTGCAAAAA|GCGGTTAGCT|CCTTCGGTCC|TCCGATCGTT|
|3451|GTCAGAAGTA|AGTTGGCCGC|AGTGTTATCA|CTCATGGTTA|TGGCAGCACT|
|3501|GCATAATTCT|CTTACTGTCA|TGCCATCCGT|AAGATGCTTT|TCTGTGACTG|
|3551|GTGAGTACTC|AACCAAGTCA|TTCTGAGAAT|AGTGTATGCG|GCGACCGAGT|
|3601|TGCTCTTGCC|CGGCGTCAAT|ACGGGATAAT|ACCGCGCCAC|ATAGCAGAAC|
|3651|TTTAAAAGTG|CTCATCATTG|GAAAACGTTC|TTCGGGGCGA|AAACTCTCAA|
|3701|GGATCTTACC|GCTGTTGAGA|TCCAGTTCGA|TGTAACCCAC|TCGTGCACCC|
|3751|AACTGATCTT|CAGCATCTTT|TACTTTCACC|AGCGTTTCTG|GGTGAGCAAA|
|3801|AACAGGAAGG|CAAAATGCCG|CAAAAAAGGG|AATAAGGGCG|ACACGGAAAT|
|3851|GTTGAATACT|CATACTCTTC|CTTTTTCAAT|ATTATTGAAG|CATTATCAG|
|3901|GGTTATTGTC|TCATGAGCGG|ATACATATTT|GAATGTATT|AGAAAAATAA|

FIG. 6C

```
3951  ACAAATAGGG  GTTCCGCGCA  CATTTCCCCG  AAAGTGCCA   CCTGACGTCT
4001  AAGAAACCAT  TATTATCATG  ACATTAACCT  ATAAAAATAG  GCGTATCACG
4051  AGGCCCTTTC  GTCTTCAC
```

FIG. 6D

|  | 10 | 20 | 30 | 40 | 50 |
|---|---|---|---|---|---|
| 1 | CTCGAGAAAT | CTTAAAAAT | TTATTGCTT | TGTGAGCGGA | TAACAATTAT |
| 51 | AATAGATTCA | ATTGTGAGCG | GATAACAATT | TCACACAGAA | TTCATTAAAG |
| 101 | AGGAGAAATT | AACTATGAGA | GGATCCGTCG | ACCTGCAGCC | AAGCTTAATT |
| 151 | AGCTGAGCTT | GGACTCCTGT | TGATAGATCC | AGTAATGACC | TCAGAACTCC |
| 201 | ATCTGGATTT | GTTCAGAACG | CTCGGTTGCC | GCCGGGCGTT | TTTTATTGGT |
| 251 | GAGAATCCAA | GCTAGCTTGG | CGAGATTTTC | AGGAGCTAAG | GAAGCTAAAA |
| 301 | TGGAGAAAAA | AATCACTGGA | TATACCACCG | TTGATATATC | CCAATGGCAT |
| 351 | CGTAAAGAAC | ATTTGAGGC | ATTTCAGTCA | GTTGCTCAAT | GTACCTATAA |
| 401 | CCAGACCGTT | CAGCTGGATA | TTACGGCCTT | TTTAAAGACC | GTAAAGAAAA |
| 451 | ATAAGCACCA | GTTTATCCG | GCCTTTATTC | ACATTCTTGC | CCGCCTGATG |
| 501 | AATGCTCATC | CGGAATTTCG | TATGCCAATG | AAAGACGGTG | AGCTGGTGAT |
| 551 | ATGGGATAGT | GTTCACCCTT | GTTACACCGT | TTTCCATGAG | CAAACTGAAA |
| 601 | CGTTTTCATC | GCTCTGGAGT | GAATACCACG | ACGATTTCCG | GCAGTTTCTA |
| 651 | CACATATATT | CGCAAGATGT | GGCGTGTTAC | GGTGAAAACC | TGGCCTATTT |
| 701 | CCCTAAAGGG | TTTATTGAGA | ATATGTTTT | CGTCTCAGCC | AATCCCTGGG |
| 751 | TGAGTTTCAC | CAGTTTTGAT | TTAAACGTGG | CCAATATGGA | CAACTTCTTC |
| 801 | GCCCCCGTT | TCACCATGGG | CAAATATTAT | ACGCAAGGCG | ACAAGGTGCT |
| 851 | GATGCCGCTC | GCGATTCAGG | TTCATCATGC | CGTCTGTGAT | GGCTTCCATG |
| 901 | TCGGCAGAAT | GCTTAATGAA | TTACAACAGT | ACTGCGATGA | GTGGCAGGGC |
| 951 | GGGGCGTAAT | TTTTTAAGG | CAGTTATTGG | TGCCCTTAAA | CGCCTGGGGT |
| 1001 | AATGACTCTC | TAGCTTGAGG | CATCAAATAA | AACGAAAGGC | TCAGTCGAAA |
| 1051 | GACTGGGCCT | TTCGTTTTAT | CTGTTGTTTG | TCGGTGAACG | CTCTCCTGAG |
| 1101 | TAGGACAAAT | CCGCCGCTCT | AGAGCTGCCT | CGCGCGTTTC | GGTGATGACG |
| 1151 | GTGAAAACCT | CTGACACATG | CAGCTCCCGG | AGACGGTCAC | AGCTTGTCTG |

FIG. 8A

| | | | |
|---|---|---|---|
| 1201 | TAAGCGGATG | CCGGAGCAG | ACAAGCCCGT | CAGGCGCGT | CAGCGGGTGT |
| 1251 | TGGCGGGTGT | CGGGCGCAG | CCATGACCCA | GTCACGTAGC | GATAGCGGAG |
| 1301 | TGTATACTGG | CTTAACTATG | CGGCATCAGA | GCAGATTGTA | CTGAGAGTGC |
| 1351 | ACCATATGCG | GTGTGAAATA | CCGCACAGAT | GCGTAAGGAG | AAATACCGC |
| 1401 | ATCAGGCGCT | CTTCCGCTTC | CTCGCTCACT | GACTCGCTGC | GCTCGGTCTG |
| 1451 | TCGGCTGCGG | CGAGCGGTAT | CAGCTCACTC | AAAGGCGGTA | ATACGGTTAT |
| 1501 | CCACAGAATC | AGGGGATAAC | GCAGGAAAGA | ACATGTGAGC | AAAAGGCCAG |
| 1551 | CAAAAGGCCA | GGAACCGTAA | AAAGGCCGCG | TTGCTGGCGT | TTTCCATAG |
| 1601 | GCTCCGCCCC | CCTGACGAGC | ATCACAAAA | TCGACGCTCA | AGTCAGAGGT |
| 1651 | GGCGAAACCC | GACAGGACTA | TAAAGATACC | AGGCGTTTCC | CCCTGGAAGC |
| 1701 | TCCCTCGTGC | GCTCTCCTGT | TCCGACCCTG | CCGCTTACCG | GATACCTGTC |
| 1751 | CGCCTTTCTC | CCTTCGGGAA | GCGTGGCGCT | TTCTCAATGC | TCACGCTGTA |
| 1801 | GGTATCTCAG | TTCGGTGTAG | GTCGTTCGCT | CCAAGCTGGG | CTGTGTGCAC |
| 1851 | GAACCCCCCG | TTCAGCCCGA | CCGCTGCGCC | TTATCCGGTA | ACTATCGTCT |
| 1901 | TGAGTCCAAC | CCGGTAAGAC | ACGACTTATC | GCCACTGGCA | GCAGCCACTG |
| 1951 | GTAACAGGAT | TAGCAGAGCG | AGGTATGTAG | GCGGTGCTAC | AGAGTTCTTG |
| 2001 | AAGTGGTGGC | CTAACTACGG | CTACACTAGA | AGGACAGTAT | TTGGTATCTG |
| 2051 | CGCTCTGCTG | AAGCCAGTTA | CCTTCGGAAA | AGAGTTGGT | AGCTCTTGAT |
| 2101 | CCGGCAAACA | AACCACCGCT | GGTAGCGGTG | GTTTTTTTGT | TTGCAAGCAG |
| 2151 | CAGATTACGC | GCAGAAAAAA | AGGATCTCAA | GAAGATCCTT | TGATCTTTTC |
| 2201 | TACGGGGTCT | GACGCTCAGT | GGAACGAAAA | CTCACGTTAA | GGGATTTTGG |
| 2251 | TCATGAGATT | ATCAAAAAGG | ATCTTCACCT | AGATCCTTTT | AAATTAAAAA |
| 2301 | TGAAGTTTTA | AATCAATCTA | AAGTATATAT | GAGTAAACTT | GGTCTGACAG |
| 2351 | TTACCCATGC | TTAATCAGTG | AGGCACCTAT | CTCAGCGATC | TGTCTATTTC |
| 2401 | GTTCATCCAT | AGCTGCCTGA | CTCCCCGTCG | TGTAGATAAC | TACGATACGG |
| 2451 | GAGGGCTTAC | CATCTGGCCC | CAGTGCTGCA | ATGATACCGC | GAGACCCACG |
| 2501 | CTCACCGGCT | CCAGATTTAT | CAGCAATAAA | CCAGCCAGCC | GGAAGGGCCG |

FIG. 8B

```
2551 AGCGCAGAAG TGGTCCTGCA ACTTTATCCG CCTCCATCCA GTCTATTAAT
2601 TGTTGCCGGG AAGCTAGAGT AAGTAGTTCG CCAGTTAATA GTTTGCGCAA
2651 CGTTGTTGCC ATGCTACAG GTCACGCTCG GTCACGCTCG TCGTTTGGTA
2701 TGGCTTCATT CAGCTCCGGT TCCCAACGAT CAAGGCGAGT TACATGATCC
2751 CCCATGTTGT GCAAAAAGC GGTTAGCTCC TTCGGTCCTC CGATCGTTGT
2801 CAGAAGTAAG TGGCCGCAG TGTTATCACT CATGGTTATG GCAGCACTGC
2851 ATAATTCTCT TACTGTCATG CCATCCGTAA GATGCTTTTC TGTGACTGGT
2901 GAGTACTCAA CCAAGTCATT CTGAGAATAG TGTATGCGGC GACCGAGTTG
2951 CTCTTGCCCG GCGTCAATAC GGGATAATAC CGCGCCACAT AGCAGAACTT
3001 TAAAAGTGCT CATCATTGGA AAACGTTCTT CGGGGCGAAA ACTCTCAAGG
3051 ATCTTACCGC TGTTGAGATC CAGTTCGATG TAACCCACTC GTGCACCCAA
3101 CTGATCTTCA GCATCTTTA CTTTCACCAG CGTTTCTGGG TGAGCAAAAA
3151 CAGGAAGGCA AAATGCCGCA AAAAAGGGAA TAAGGGCGAC ACGGAAATGT
3201 TGAATACTCA TACTCTTCCT TTTTCAATAT TATTGAAGCA TTTATCAGGG
3251 TTATTGTCTC ATGAGCGGAT ACATATTTGA ATGTATTTAG AAAAATAAAC
3301 AAATAGGGGT TCCGCGCACA TTTCCCCGAA AAGTGCCACC TGACGTCTAA
3351 GAAACCATTA TTATCATGAC ATTAACCTAT AAAAATAGGC GTATCACGAG
3401 GCCCTTTCGT CTTCAC
```

FIG. 8C

|      | 10         | 20         | 30         | 40         | 50         |
|------|------------|------------|------------|------------|------------|
| 0    | AAGCTTCACG | CTGCCCCAAG | CACTCAGGGC | GCAAGGGCTG | CTAAGGAAG  |
| 50   | CGGAACACGT | AGAAAGCCAG | TCCGCAGAAA | CGGTGCTGAC | CCCGGATGAA |
| 100  | TGTCAGCTAC | TGGGCTATCT | GGACAAGGGA | AAACGCAAGC | GCAAAGAGAA |
| 150  | AGCAGGTAGC | TGCAGTGGG  | CTTACATGGC | GATAGCTAGA | CTGGGCGGTT |
| 200  | TATGGACAG  | CAAGCGAACC | GGAATTGCCA | GCTGGGGCGC | CCTCTGGTAA |
| 250  | GGTTGGGAAG | CCCTGCAAAG | TAAACTGGAT | GGCTTTCTTG | CCGCCAAGGA |
| 300  | TCTGATGGGG | CAGGGGATCA | AGATCTGATC | AAGACACAGG | ATGAGGATCG |
| 350  | TTCGGCATGA | TTGAACAAGA | TGGATTGCAC | GCAGGTTCTC | CGGCCGCTTG |
| 400  | GGTGGAGAGG | CTATTCGGCT | ATGACTGGGG | ACAACAGACA | ATCGGCTGCT |
| 450  | CTGATGCCGC | CGTGTTCCGG | CTGTCAGCGC | AGGGGCGCC  | GGTTCTTTT  |
| 500  | GTCAAGACCG | ACCTGTCCGG | TGCCCTGAAT | GAACTGCAGG | ACGAGGCAGC |
| 550  | GCGGCTATCG | TGGCTGGCCA | CGACGGGCGT | TCCTTGCGCA | GCTGTGCTCG |
| 600  | ACGTTGTCAC | TGAAGCGGGA | AGGGACTGGC | TGCTATTGGG | CGAAGTGCCG |
| 650  | GGGCAGGATC | TCCTGTCATC | TCACCTTGCT | CCTGCCGAGA | AAGTATCCAT |
| 700  | CATGGCTGAT | GCAATGCGGC | GGCTGCATAC | GCTTGATCCG | GCTACCTGCC |
| 750  | CATTCGACCA | CCAAGCGAAA | CATCGCATCG | AGCGAGCACG | TACTCGGATG |
| 800  | GAAGCCGGTC | TTGTCGATCA | GGATGATCTG | GACGAAGAGC | ATCAGGGGCT |
| 850  | CGCGCCAGCC | GAACTGTTCG | CCAGGCTCAA | GGCGCGCATG | CCCGACGGCG |
| 900  | AGGATCTCGT | CGTGACCCAT | GGCGATGCCT | GCTTGCCGAA | TATCATGGTG |
| 950  | GAAAATGGCC | GCTTTTCTGG | ATTCATCGAC | CGTTGGCTAC | TGTGGGCCGGC |
| 1000 | GGACCGCTAT | CAGGACATAG | CGTTGGCTAC | CCGTGATATT | GCTGAAGAGC |
| 1050 | TTGGCGGCGA | ATGGGCTGAC | CGCTTCCTCG | TGCTTTACGG | TATCGCCGCT |
| 1100 | CCCGATTCGC | AGCGCATCGC | CTTCTATCGC | CTTCTTGACG | AGTTCTTCTG |
| 1150 | AGCGGGACTC | TGGGGTTCGA | AATGACCGAC | CAAGCGACGC | CCAACCTGCC |

FIG. 10A

| | 10 | 20 | 30 | 40 | 50 |
|---|---|---|---|---|---|
| 1200 | ATCACGAGAT | TTCGATTCCA | CCGCCCGCCTT | CTCTGAAAGG | TTGGGCTTCG |
| 1250 | GAATCGTTTT | CCGGGACGCC | GGCTGGATGA | TCCTCCAGCC | CGGGATCTC |
| 1300 | ATGCTGGAGT | TCTTCGCCCA | CCCCGGGCTC | GATCCCCTCG | CGAGTTGGTT |
| 1350 | CAGCTGCTGC | CTGAGGCTGG | ACGACCTCGC | GGAGTTCTAC | CGGCAGTGCA |
| 1400 | AATCCGTCGG | CATCCAGGAA | ACCAGCAGCG | GCTATCCGCG | CATCCATGCC |
| 1450 | CCCGAACTGC | AGGAGTGGGG | AGGCACGATG | GCCGCTTTGG | TCGACAATTC |
| 1500 | GCCTAACTT | ACATTAATTG | CGTTGCGCTC | ACTGCCCGCT | TTCCAGTCGG |
| 1550 | GAAACCTGTC | GTGCCAGCTG | CATTAATGAA | TCGGCCAACG | CGCGGGGAGA |
| 1600 | GCCGGTTTGC | GTATTGGGGG | CCAGGGTGGT | TTTCTTTTC | ACCAGTGAGA |
| 1650 | CGGGCAACAG | CTGATTGCCC | TTCACCGCCT | GGCCCTGAGA | GAGTTACAGC |
| 1700 | AAGCGGTCCA | CGCTGGTTTG | CCCCAGCAGG | CGAAAATCCT | GTTTGATGGT |
| 1750 | GGTTAACGGC | GGGATATAAC | CCCCAGCAGG | TTCGTATCG | TCGTATCCCA |
| 1800 | CTACCGAGAT | ATCCGCACCA | ATGAGCTGTC | CGGACTCGGT | AATGCCGCGC |
| 1850 | ATGCGCCCA | GCGCCATCTG | ACGCGCAGCC | CGGACTCGGT | CAGTGGGAAC |
| 1900 | GATGCCCTCA | TTCAGCATT | GCATGGTTTG | ACCAGCATCG | GACATGGCAC |
| 1950 | TCCAGTCGCC | TTCCCGTTCC | GCTATCGGCT | TTGAAAACCG | GCGAGTGAGA |
| 2000 | TATTTATGCC | AGCCAGGCAG | ACGCAGACGC | GAATTTGAT | GCCGAGACAG |
| 2050 | GCCGCTAAC | AGCGCGATTT | GCTGGTGACC | GCCGAGACAG | AACTTAATGG |
| 2100 | CGCCCAGTCG | CGTACCGTCT | TCATGGGAGA | CAATGCGACC | AGATGCTCCA |
| 2150 | CGTCGGTCAG | AGACATCAAG | AAATAAGCC | AAATAATACT | GTTGATGGGT |
| 2200 | TCCACAGCA | ATGGCATCCT | GGTCATCCAG | GGAACATTAG | TGCAGGCAGC |
| 2250 | CACTGACGCG | TTGGCGCGGA | AGATTGTGCA | CGGATAGTTA | ATGATCAGCC |
| 2300 | ACGCGGCTTC | GTTCTACCAT | CGACACCACC | CCGCCCTTT | ACAGGCTTCG |
| 2350 | GGCGCGAGAT | TTAATCGCCG | CGACAATTTG | ACGTGGCAC | CCAGTTGATC |
| 2400 | GACTGGAGGT | GGCAACGCCA | ATCAGCAACG | CGACGCGCG | TGCAGGCCA |
| 2450 | TGTGCCACGC | GGTTGGGAAT | GTAATTCAGC | ACTGTTTGCC | CGCCAGTTGT |
| 2500 | TTTTCCCGC | GTTTTCGCAG | AAACGTGGCT | TCCGCCATCG | CCGCTTCCAC |
| 2550 | AACGGTCTG | ATAAGAGACA | CCGGCATACT | GGCCTGGTTC | ACCAGCGGG |
| 2550 | | | | CTGCCACATC | GTATAACGTT |

FIG. 10B

|  | 10 | 20 | 30 | 40 | 50 |
|---|---|---|---|---|---|
| 2600 | ACTGGTTTCA | CATTCACCAC | CCTGAATTGA | CTCTCTTCCG | GGCGTATCA |
| 2650 | TGCCATACCG | CGAAAGGTTT | TGCACCATTC | GATGGTGTCA | ACGTAAATGC |
| 2700 | ATGCCCGCTTC | GCCTTCGCGC | GCGAATTGTC | GACCCTGTCC | CTCCTGTTCA |
| 2750 | GCTACTGAGG | GGGTGGTGCG | TAACGGCAAA | AGCACCGCCG | GACATCAGCG |
| 2800 | CTAGCGGAGT | GTATACTGGC | TTACTATGTT | GGCACTGATG | AGGGTGTCAG |
| 2850 | TGAAGTGCTT | CATGTGGCAG | GAGAAAAAG | GCTGCACCGG | TGCGTCAGCA |
| 2900 | GAATATGTGA | TACAGGATAT | ATTCCGCTTC | CTCGCTCACT | GACTCGCTAC |
| 2950 | GCTCGGTCGT | TCGACTGCGG | CGAGCGGAAA | TGGCTTACGA | ACGGGGCGGA |
| 3000 | GATTTCCTGG | AAGATGCCAG | GAAGATACTT | AACAGGAAG | TGAGAGGGCC |
| 3050 | GCGGCAAAGC | CGTTTTTCCA | TAGGCTCCGC | CCCCCTGACA | AGCATCACGA |
| 3100 | AATCTGACGC | TCAAATCACT | GGTGGCGAAA | CCCGACAGGA | CTATAAAGAT |
| 3150 | ACCAGGCGTT | TCCCCCTGGCC | GCTCCCTCGT | GCGCTCTCCT | GTTCCTGCCT |
| 3200 | TTCGGTTTAC | CGGTGTCATT | CCGCTGTTAT | GCCGCGCGTT | GTCTCATTCC |
| 3250 | ACGCCTGACA | CTCAGTTCCG | GGTAGGCAGT | TCGCTCCAAG | CTGGACTGTA |
| 3300 | TGCACGAACC | CCCCGTTCAG | TCCGACCGCT | GCGCTTATC | CGGTAACTAT |
| 3350 | CGTCTTGAGT | CCAACCCGGA | AAGACATGCA | AAGCACCAC | TGGCAGCAGC |
| 3400 | CACTGGTAAT | TGATTTAGAG | GAGTTAGTCT | TGAAGTCATG | CGCCGGTTAA |
| 3450 | GGCTAAACTG | AAAGGACAAG | TTTTGGTGAC | TGCGCTCCTC | CAAGCCAGTT |
| 3500 | ACCTCGGTTC | AAGAGTTGG | TAGCTCAGAG | AACCTTCGAA | AAACCGCCCT |
| 3550 | GCAAGGCGGT | TTTTTCGTT | TCAGAGCAAG | AGATTACGCG | CAGACCAAAA |
| 3600 | CGATCTCAAG | AAGATCATCT | TATTAATCAG | ATAAAATATT | TCTAGATTTC |
| 3650 | AGTGCAATTT | ATCTCTTCAA | ATGTAGCACC | TGAAGTCAGC | CCCATACGAT |
| 3700 | ATAAGTTGTT | AATTCTCATG | TTTGACAGCT | TATCATCGAT |  |

FIG. 10C

```
              (SphI)         (NdeI)
              CAGGACCCA
ADAPTER 1:
              GTACGTCCTGGGTAT (HinfI)         (HindIII)
              AGTCAGATGCTGTAGTTAACA
ADAPTER 2:
                  GTCTACGACATCAATTGTTCGA (SphI)         Nael         NarI      (BamHI)
              CATCACGCCGGCATCGAAGGGCGCCTTG
ADAPTER 3:
              GTACGTAGTGCGGCCGTAGCTTCCCGCGGAACCTAG (NarI)        (NdeI)
              CGCCAAGATCCA
ADAPTER 4:
                  GGTTCTAGGTAT (NarI)                          (NdeI)
              GGCGATGACGATGACAAACAAGATCCA
ADAPTER 5:
              CCGCTACTGCTACTACTGTTTGTTCTAGGTAT (NarI)         (NdeI)
              CGCCAAAACCCA
ADAPTER 6:
                  GGTTTTGGGTAT
```

FIG. 11A

ADAPTER 7:
```
                              (BamHI)
         GATCGCATCACCATCACCATCACG
             CGTAGTGGTAGTGGTAGTGCCTAG
```

ADAPTER 8:
```
                    (BamHI)
         AGTCAGATGCTGTAGTTAACA
                CGTAGTGGTAGTGCCTAG
```

ADAPTER 9:
```
         (BamHI)  BglII                    (HindIII)
         GATCCAGATCTCATCACCATCACCATCACTA
             GTCTAGAGTAGTGGTAGTGGTAGTGATTCGA
```

ADAPTER 10:
```
         (BamHI)  BglII                    (HindIII)
         GATCCAGATCTCATCACCATCACTA
             GTCTAGAGTAGTGGTAGTGATTCGA
```

ADAPTER 11:
```
         (BamHI)  BglII                    (HindIII)
         GATCCAGATCTCATCACTA
             GTCTAGAGTAGTGATTCGA
```

FIG. 11B

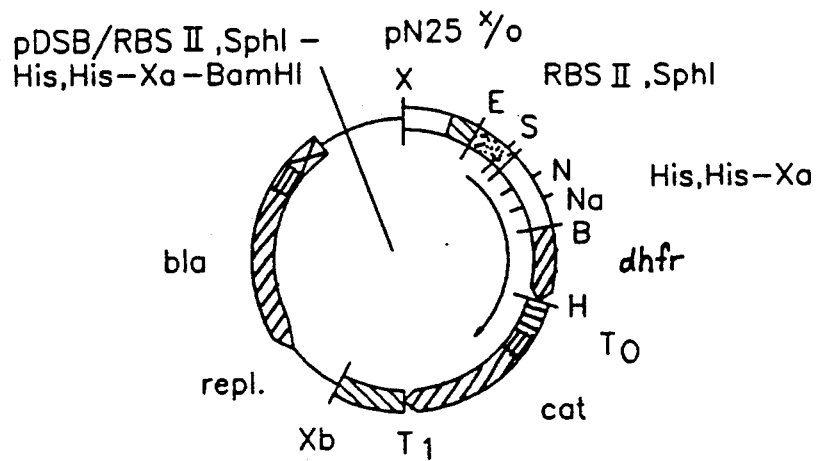
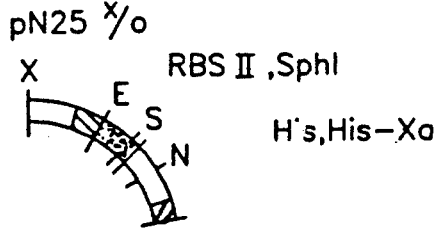
FIG. 22

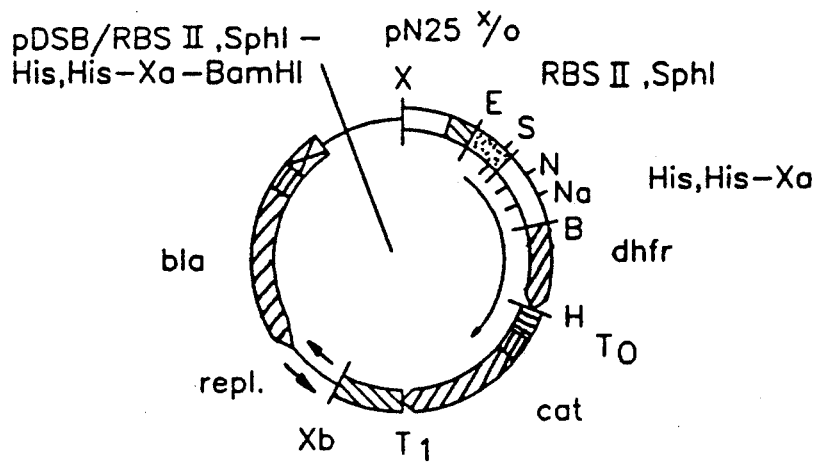
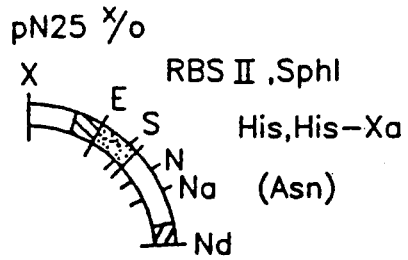
FIG. 25

FIG. 40A

| | | | | | | | | | | | | |
|---|---|---|---|---|---|---|---|---|---|---|---|---|
| ATG | CAG | GAC | CCA | TAT | GTA | AAA | GAA | GCA | AAC | CTT | AAG | TAT |
| MET | Gln | ASP | Pro | Tyr | Val | Lys | Glu | Ala | Asn | Leu | Lys | Tyr |
| | | | 10 | | | 20 | | | 30 | | 40 | |
| TTT | AAT | GCA | GGT | CAT | TCA | GAT | GTA | GCG | GAT | AAT | ACT | CTT | TTC |
| Phe | Asn | Ala | Gly | His | Ser | Asp | Val | Ala | Asp | Asn | Thr | Leu | Phe |
| 50 | | | | 60 | | | 70 | | | | 80 | | 90 |
| TTA | GGC | ATT | TTG | AGG | AAT | TGG | AAA | GAG | GAG | AGT | GAC | AGA | ATA |
| LeU | Gly | Ile | Leu | Lys | Asn | Trp | Lys | Glu | Glu | Ser | Asp | Arg | Ile |
| | 100 | | | | 110 | | | | 120 | | | 130 | 140 |
| ATG | CAG | AGC | CAA | ATT | GTC | AGC | CAG | TAC | TTC | AAA | CTT | AAC |
| MET | Gln | Ser | Gln | Ile | Val | Ser | Gln | Tyr | Phe | Lys | Leu | Asn |
| | | | 150 | | | | 160 | | | | 170 | 180 |
| TTT | AAA | GAT | CAG | AGC | ATC | CAA | AAG | AGT | GAG | ACC | ATC | AAG |
| Phe | Lys | Asp | Gln | Ser | Ile | Gln | Lys | Ser | Glu | Thr | Ile | Lys |
| | 190 | | | | 200 | | | 210 | | | 220 | |
| GAA | GAC | ATG | ATT | GTC | AAG | TTT | TTC | AAT | TAT | AGC | AAC | AAG | AAA |
| Glu | Asp | MET | Ile | Val | Lys | Phe | Phe | Asn | Tyr | Ser | Asn | Lys | Lys |
| | | 230 | | 240 | | | 250 | | | | | 260 | 270 |
| GAT | GAC | TTC | GAA | AAG | CTG | ACT | AAT | TAT | TCG | GTA | ACT | GAC | TTG | AAT |
| Asp | Asp | Phe | Glu | GLU | Leu | Thr | Asn | Tyr | Ser | Val | Thr | Asp | Leu | Asn |
| | | 280 | 290 | | | 300 | | | | | | 350 | | 360 |
| GTC | CAA | CGC | AAA | GCA | ATA | CAT | GAA | CTC | ATC | CAA | ATG | GTG | GCT | GAA |
| Val | Gln | Arg | Lys | Ala | Ile | His | Glu | Leu | Ile | Gln | MET | Val | Ala | Glu |

```
CTG TCG CAA GCA GCT AAA  ACA GGG AAG  CGA AAA AGG AGT CAG ATG
Leu Ser Pro Ala Ala Lys  Thr Gly Lys  Arg Lys Arg Ser Gln MET
    410         370      380      430      390      400
CTG TTT CGA GGT CGA AGA  CGA TCC CAG
Leu Phe Arg Gly Arg Arg  Arg Ser Gln
        420
```

FIG. 40B

| | | | | | | | | | |
|---|---|---|---|---|---|---|---|---|---|
| ATG | CAT | CAC | GGC | ATC | | | | | |
| MET | His | His | Gly | Ile | | | | | |
| | | | | 10 | | | | | |
| GAA | GCA | GAT | AAC | AAG | CTT | AAG | GGG | CGC | CAA |
| Glu | Ala | Asp | Asn | Lys | Leu | Lys | Gly | Arg | Gln |
| 50 | | | | | | | 20 | | |
| | | | | | | | | | |
| GAT | CCA | TAT | GTA | AAA | | | | | |
| Asp | Pro | Tyr | Val | Lys | | | | | |
| 30 | | | 40 | | | | | | |
| | | | | | | | | | |
| GTA | GCG | GAT | AAC | AAG | CTT | TAT | TTT | AAT | GCA |
| Val | Ala | Asp | Asn | Lys | Leu | Tyr | Phe | Asn | Ala |
| | 140 | | 100 | | | | | | |
| | | | | | | | 70 | | |
| CAT | TCA | GAT | | | | | | | |
| His | Ser | Asp | | | | | | | |
| | 130 | | | | | | | | |

FIG. 41A (OCR of this rotated sequence figure is approximate; the figure lists codons with their amino acid translations numbered 10–360.)

```
           370       380       390       400
GAA CTC ATC GTG ATG GCT GAA CTG TCG CAA GCT AAA ACA
Glu Leu Ile Gln Val MET Ala Glu Leu Ser Pro Ala Lys Thr
         410                 430           440           450
GGG AAG CGA AAA AGG CAG ATG CTG TTT CGA GGT CGA AGA GCA
Gly Lys Arg Lys Arg Ser Gln MET Leu Phe Arg Gly Arg Arg Ala

TCC CAG
Ser Gln
```

```
ATG CAT CAC GCC GGC GAT GAC GAT GAC AAA CAA GAT CCA TAT GTA
MET His His Ala Gly Asp Asp Asp Asp Lys Gln Asp Pro Tyr Val
                    10          20          30          40

AAA GAA GCA AAC CTT AAG ACT TAT AAA TTT AAT GCA GGT CAT TCA
Lys Glu Ala Asn Leu Lys Thr Tyr Lys Phe Asn Ala Gly His Ser
 50         100         110         70          120         130

GAT GTA GCG GAT AAT GAC AGA TTT CTT TTA ATG CAG TTT ATT TTG AAT
Asp Val Ala Asp Asn Asp Arg Phe Leu Leu MET Gln Phe Ile Leu Asn
        140         150         160         170         180

TGG GAG GAG GAC AGT AAA AAA ATA AAC ATG TTT AAA GAC AGC CAA ATT AGC
Trp Glu Glu Asp Ser Lys Lys Ile Asn MET Phe Lys Asp Ser Gln Ile Ser
         190         200         210         220

TCC TAC TTC AAG CTT TTT GAG AAC AAG GAA GAT ATG TTC CAG GTC AGC
Ser Tyr Phe Lys Leu Phe Glu Asn Lys Glu Asp MET Phe Gln Val Ser
230         240         250         260         270

ATC CAA AAG AGT GTG GAG ACC AAA GAC AAT GTC AAG
Ile Gln Lys Ser Val Glu Thr Lys Asp Asn Val Lys
        280         290         300         310

TTT TTC AAT AGC AAC AAA CGA AAG GAC TTC GAA CTG
Phe Phe Asn Ser Asn Lys Arg Lys Asp Phe Glu Leu
```

```
       320          330          340          350          360
ACT AAT TAT TCG GTA ACT GAC TTG AAT GTC CAA CGC AAA GCA ATA
MET Asn Tyr Ser Val Thr Asp Leu Asn Val Gln Arg Lys Ala Ile
            370          380          390          400
CAT GAA CTC ATC CAA GTG ATG GCT GAA CTG TCG CAA GCA GCT AAA
His Glu Leu Ile Gln Val MET Ala Glu Leu Ser Ala Gly His Lys
        410          420          430
ACA GGG AAG CGA AAA AGG AGT CAG ATG CTG
Thr Gly Lys Arg Lys Arg Ser Gln MET Leu
```

```
ATG CAT CAC GCC GGC ATC GAA GGG CGC GAA AAC CCA TAT GTA AAA
MET His His Ala Gly Ile Glu Gly Arg Gln Asn Pro Tyr Val Lys
            10        20        30        40        90

GAA GCA GAA AAC CTT AAG TAT TTT AAT GCA CCA GGT CAT TCA GAT
Glu Ala Glu Asn Leu Lys Tyr Phe Asn Ala Pro Gly His Ser Asp
50            60        70        80       100       130

GAT GCG GAT AAT GGA ACT TTC TTA TTA ATA GGC ATT CAG AGC TGG
Val Ala Asp Asn Gly Thr Phe Leu Leu Ile Gly Ile Gln Ser Trp
140       150       160                  170       180

AAA GAG GAG AGT AGA GAC CTT AAA ATG AAC TTT CAA CAG AGC TCC
Trp Glu Glu Ser Asp Arg Leu Lys MET Asn Phe Gln Gln Ser Ser
    190                        200       210       220

TTT TAC TTC AAA CTT GAG ACC ATC AAG AAC GAT GAT ATG AAG ATC
Phe Tyr Phe Lys Leu Glu Thr Ile Lys Asn Asp Asp MET Lys Ile
230       240       250            260                270

CAA AAG AGT GTG GAG ATC AAG AAG GAA GAC ATG GTC AAG TTT
Gln Lys Ser Val Glu Thr Lys Lys Glu Asp MET Val Lys Phe
    280       290       300                      310

TTC AAT AGC AAC AAG AAA CGA GAT GAC TTC GAA AAG CTG ACT
Phe Asn Ser Asn Lys Lys Arg Asp Asp Phe Glu Lys Leu Thr
```

```
       320             330             340             350             360
AAT TAT TCG GTA ACT GAC TTG AAT GTC CAA CGC AAA GCA ATA CAT
Asn Tyr Ser Val Thr Asp Leu Asn Val Gln Arg Lys aLA iLE hIS
           370             380             390             400
GAA CTC ATC CAA GTG ATG GCT GAA CTG TCG CCA GCA GCT AAA ACA
Glu Ile Gln Val MET Ala Glu Leu Ser Pro Ala Ala Lys Thr
           410             420             430
GGG AAG CGA AAA AGG AGT CAG ATG CTG
Gly Lys Arg Lys Arg Ser Gln MET Leu

FIG. 43B
```

AFFINITY PEPTIDES

This is a division of application Ser. No. 07/158,962 filed Feb. 22, 1988, now allowed.

TECHNICAL FIELD

This invention relates to fusion proteins containing affinity peptides, genes coding for such proteins, expression vectors and transformed microorganisms containing such genes, and methods for the purification of the fusion proteins.

BACKGROUND OF THE INVENTION

The possibility of preparing hybrid genes by gene technology has opened up new routes for the workup of recombinant proteins. By linking the coding gene sequence of a desired protein to the coding gene sequence of a protein fragment having a high affinity for a ligand (affinity peptide), it is possible to purify desired recombinant proteins in the form of fusion proteins in one step using the affinity peptide.

By site-directed mutagenesis it is also possible to introduce specific chemical or enzymatic cleavage sites at the point of linkage of the affinity peptide and the desired recombinant protein, so that after the purification of the fusion protein by means of a suitable affinity resin, the desired recombinant protein can be recovered by chemical or enzymatic cleavage. Such purification methods have been described, for example, in Science 198, 1056–1063 (1977) (Itakura et al.); Proc. Natl. Acad. Sci. U.S.A. 80, 6848–6852 (1983) (Germino et al.); Nucleic Acids Res. 13, 1151–1162 (1985) (Nilsson et al.): Gene 32, 321–327 (1984) (Smith et al.). and European Patent Applications publication Nos. 150 126 and 184 355.

SUMMARY OF THE INVENTION

This invention provides affinity peptides having at least two neighbouring histidine residues which are especially suitable for the purification of recombinant proteins by means of metal chelate affinity chromatography in nitrilotriacetic acid (NTA) resins. These affinity peptides can be distinguished from the previously known peptides primarily in that they permit the problem-free purification of native and denatured proteins by means of NTA resins.

More particularly, this invention provides fusion proteins which contain one or two affinity peptides, which peptides contain neighbouring histidine residues, and a biologically active polypeptide or protein linked directly or indirectly to this/these affinity peptide(s); a process for their preparation by means of recombinant DNA technology and a process for their purification by means of metal chelate affinity chromatography in NTA resins. The present invention also provides genes which code for these fusion proteins, expression vectors which contain these genes, microorganisms transformed with these expression vectors and processes for the preparation of said genes, expression vectors and transformed microorganisms.

The affinity peptides of the fusion proteins of the invention are defined by the general formula $$R^1-(His)_{2-6}-R^2$$

wherein $R^1$ represents hydrogen or from 1 to about 30 amino acids; and $R^2$ represents Q, Q-Ile-Glu-Gly-Arg- or Q-Asp-Asp-Asp-Asp-Lys-, where Q is a peptide bond or from 1 to about 30 amino acids. Especially preferred affinity peptides have the following amino acid sequences:

Met-His-His,
Met-His-His-His,
Met-His-His-His-His,
Met-His-His-His-His-His,
Met-His-His-His-His-His-His,
Met-His-His-Ala-Gly-Ile-Glu-Gly-Arg and
Met-His-His-Ala-Gly-Asp-Asp-Asp-Asp-Lys.

BRIEF DESCRIPTION OF THE FIGURES

This invention can be more readily understood by reference to the following Description of the Invention and Examples, and to the accompanying Figures. The following abbreviations and symbols appear in these Figures:

B, Bg, E, H, N, Na, Nd, P, S, Sa, Sc, X and Xb denote cleavage sites for the restriction enzymes BamHI, BglII, EcoRI, HindIII, NaeI, NarI, NdeI, PstI, SphI, SAlI, ScaI, XhoI and XbaI, respectively.

▭▭▭ represents the promoters of the genes bla, lacI and neo; ▬▬▬ represents the ribosomal binding sites of the genes bla, cat, neo and lacI; ⬚⬚⬚⬚⬚ represents the terminators $t_o$ and T1; ▭▬ represents the regulatable promoter/operator element $P_{N25X/O}$ or N25OPSN25OP29; ⋯⋯⋯ represents the ribosomal binding sites RBSII,SphI and RBSII,3A+5A;→ represents the coding regions under control of these ribosomal binding sites; ▭▭ represents the regions which code for the affinity peptides in accordance with the invention as well as the selective cleavage sites; ▧▧▧ represents the regions which code for 2.4 or 6 histidine residues;⇌ represents the region required for replication (repl.); ▬▬▶ represents coding regions for dihydrofolate reductase (dhfr), chloramphenicol acetyltransferase, lac-repressor (lacI), β-lactamase (bla), neomycin phosphotransferase (neo) and the various derivatives of γ-interferon.

FIG. 1

Schematic representation of plasmid pDS8/RBSII, SphI.

FIGS. 2A-B

Figure 1:
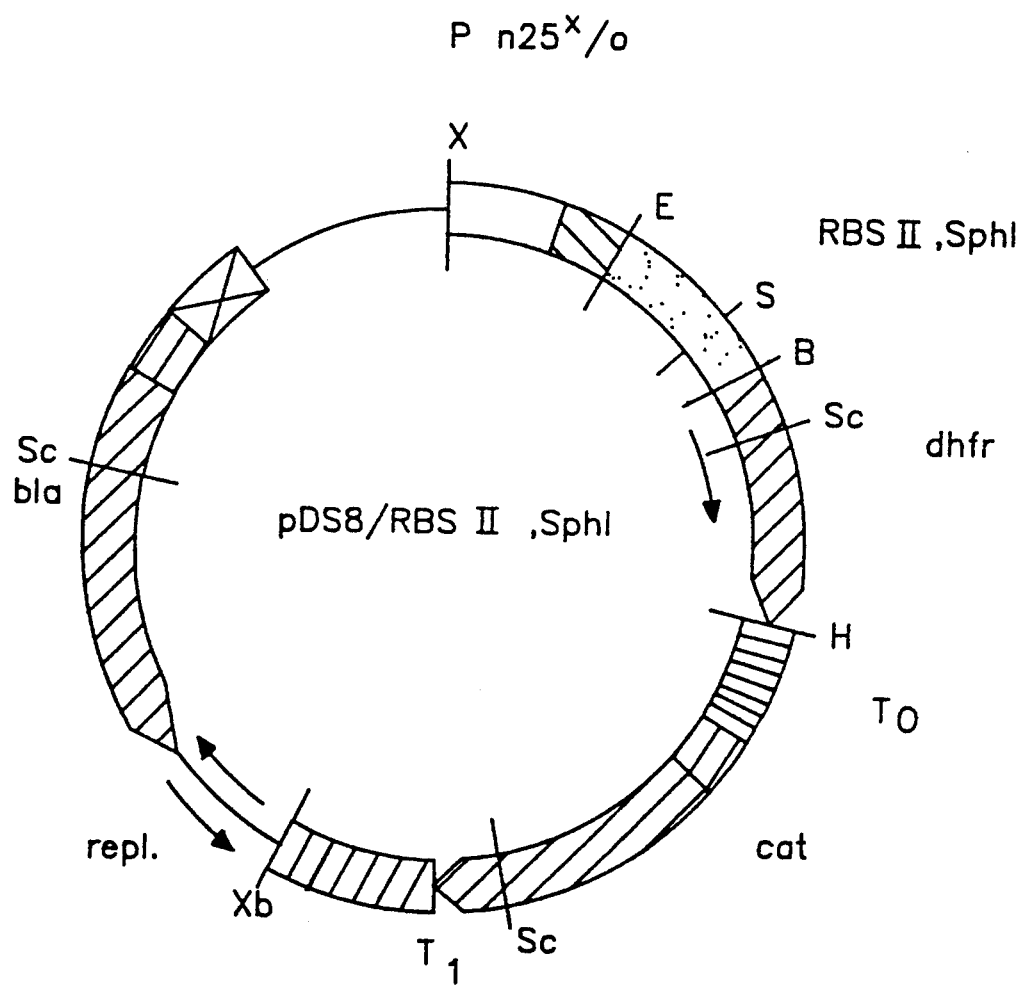

Nucleotide sequence of the XhoI/XbaI fragment of plasmid pDS8/RBSII,SphI. This fragment contains the regulatable promoter/operator element $P_{N25X/O}$, the ribosomal binding site RBSII,SphI, the dhfr gene, the terminator $t_o$, the cat gene and the terminator T1. The cleavage sites for restriction enzymes given in FIG. 1 are overlined, while the region being under control of RBSII,SphI, which codes for a variant of dihydrofolate reductase, is underlined. In addition, the part of the plasmid pDS8/RBSII,SphI originating from plasmid pRB322 is shown schematically, with the given numbers referring to the sequence of pBR322 (J.G. Sutcliffe, Cold Spring Harbor Symp. Quant. Biol. 43, pp. 77–90 (1979]).

FIG. 3

Schematic representation of plasmid pDS5/RBSII, 3A+5a.

FIGS. 4A–C

Figure 3:
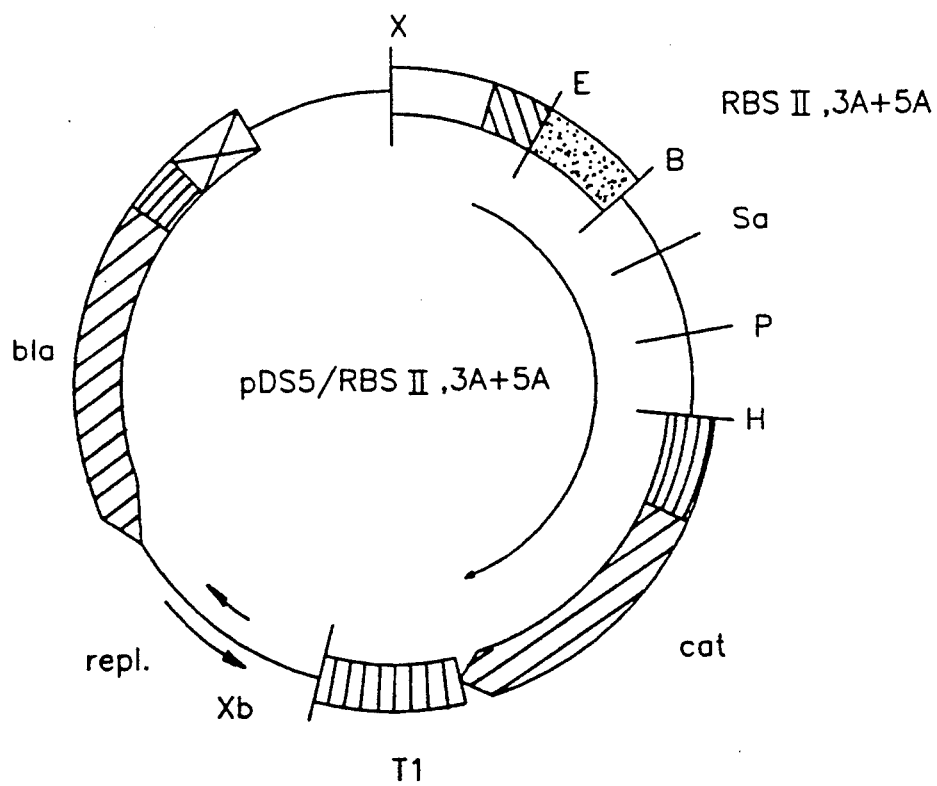

Nucleotide sequence of plasmid pDS5/RBSII,-3A+5A. The cleavage sites for restriction enzymes given in FIG. 3 are overlined, while the region under the control of RBSII,3A+5A. which codes for a variant of chloramphenicol transferase, is underlined.

FIG. 5

Schematic representation of plasmid pDS78/RBSII.

FIGS. 6A–D

Figure 5:
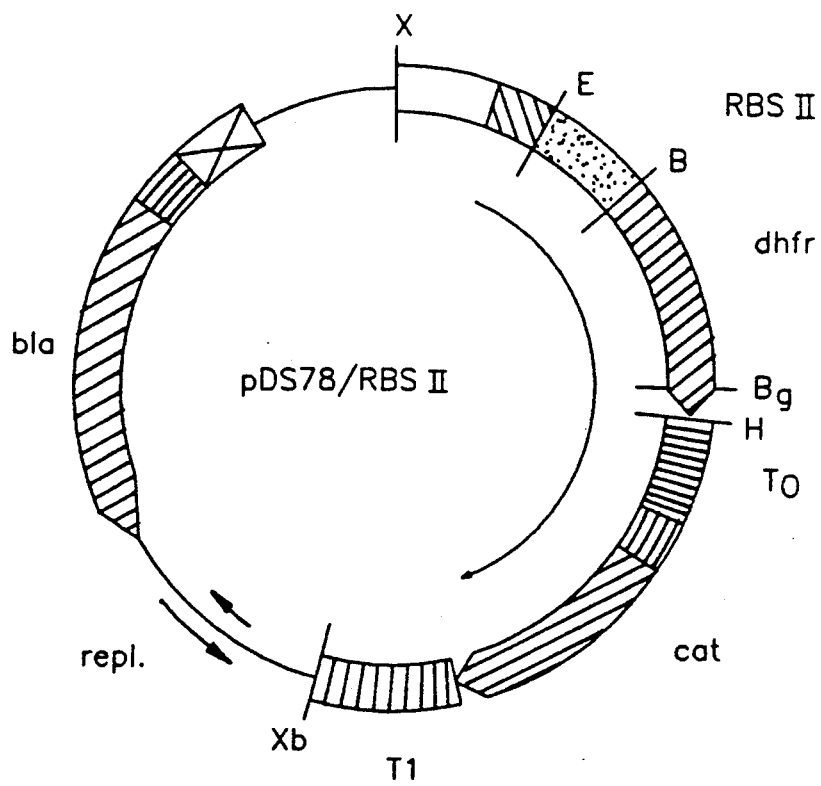

Nucleotide sequence of plasmid pDS78/RBSII. The cleavage sites for restriction enzymes given in FIG. 5 are overlined, while the region under the control of RBSII, which codes for a variant of dihydrofolate reductase, is underlined.

FIG. 7

Schematic representation of plasmid pDS56/RBSII.

FIGS. 8A–C

Figure 7:
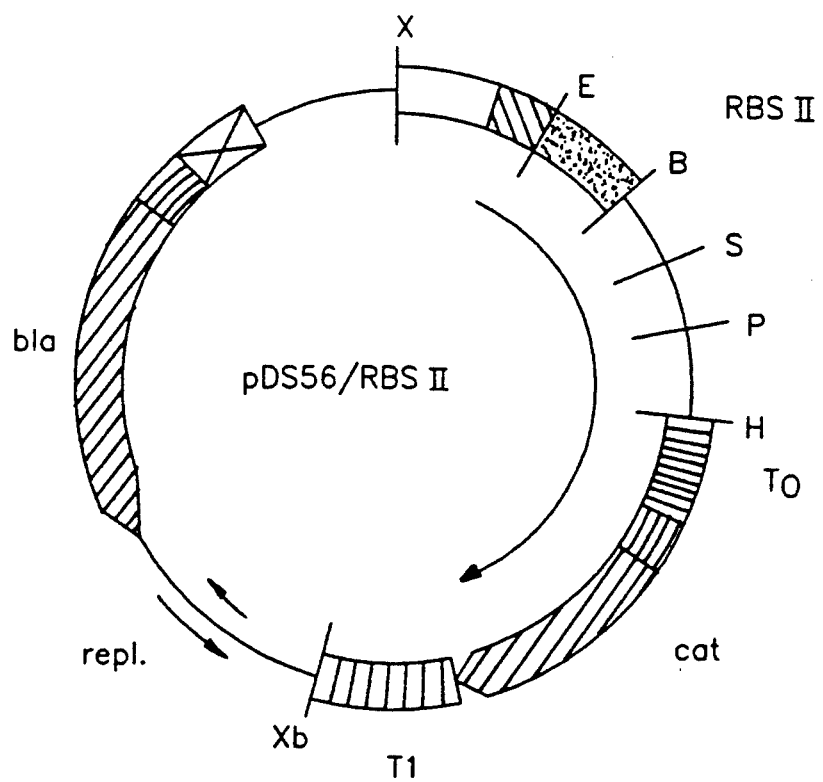

Nucleotide sequence of plasmid pDS56/RBSII. The cleavage sites for restriction enzymes given in FIG. 7 are overlined, while the region under the control of RBSII is underlined.

FIG. 9

Schematic representation of plasmid pDMI,l.

FIGS. 10A–C

Figure 9:
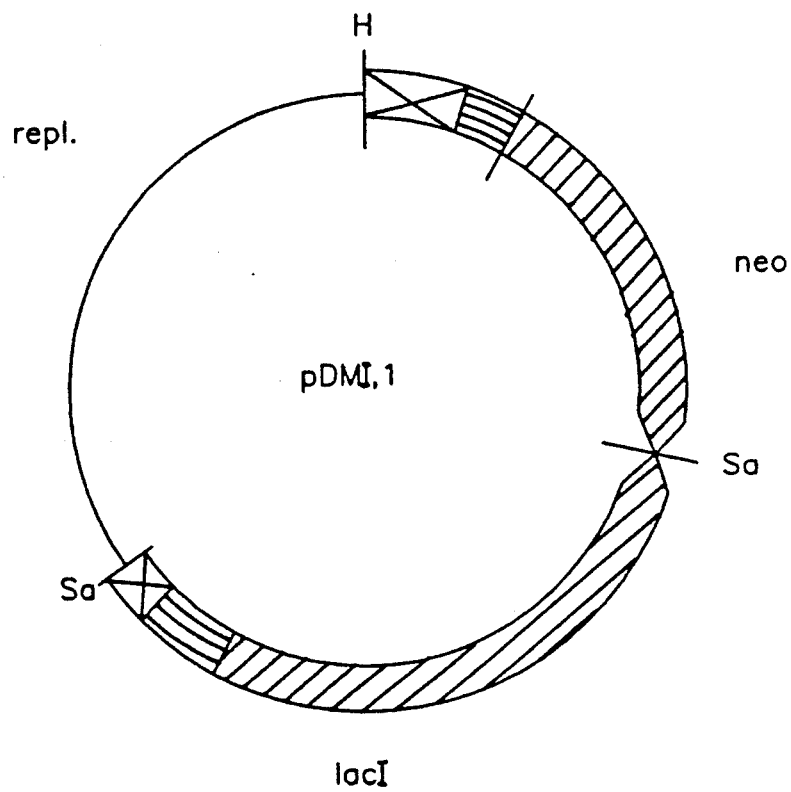

Nucleotide sequence of plasmid pDMI,l. The cleavage sites for restriction enzymes given in FIG. 9 are overlined, while the regions coding for neomycin phosphotransferase (neo) and lac-repressor (lacI) are underlined.

FIGS. 11A–B

Nucleotide sequences of the oligonucleotides which are employed for the construction of the plasmids used in the Examples. In each case two such oligonucleotides were combined and referred to as the adaptor. The cleavage sites for the restriction enzymes NaeI, NarI and BglII are overlined.

FIG. 12

Schematic representation of the construction and isolation of fragment 1. This fragment was isolated from the plasmid pRC23/IFI-900 and contains the gene for the recombinant human interferon having Cys-Tyr-Cys as the N-terminal amino acids.

FIG. 13

Schematic representation of the construction of the plasmid pGLS by incorporating fragment 1 into plasmid pDS8/RBSII,SphI. In the schematic representation of pGLS, (Sc) denotes the position at which fragment 1 has been linked with plasmid pDS8/RBSII,SphI via the cleavage site for the restriction enzyme ScaI.

FIG. 14

Schematic representation of the construction and isolation of fragment 2. This fragment codes for a human interferon which is shortened at the C-terminus by 8 amino acids and which is referred to as IFN-$\gamma$(-8). In the given nucleotide sequences the corresponding termination codon is underlined.

FIG. 15

Schematic representation of the construction of plasmid pIFN-$\gamma$(-8) by incorporating fragment 2 into plasmid pDS8/RBSII,SphI via the cleavage sites for restriction enzymes EcoRI and HindIII.

FIG. 16

Schematic representation of the construction and isolation of fragment 3. This fragment carries the regulatable promoter/operator element $P_{N25x/O}$, the ribosomal binding site RBSII,SphI and the adator 3 which codes for the amino acid sequence Met-His-His-Ala-Gly-Ile-Clu-Gly-Arg-Leu-Gly-Ser.

FIG. 17

Schematic representation of the construction of plasmid pDS8/RBSII,SphI-His,His-Xa-BamHI by incorporating fragment 3 into plasmid pDS8/RBSII,SphI via the cleavage sites for the restriction enzymes XhoI and BamHI.

FIG. 18

Schematic representation of the construction and isolation of fragment 4 which was used in the construction of plasmid pHis,His-Xa-IFN-$\gamma$.

FIG. 19

Schematic representation of the isolation of fragment 5 which was used in the construction of plasmids pHis,-His-Xa-IFN-$\gamma$, pHis,His-Ek-IFN-$\gamma$(-8) and phis, His-Xa-IFN-$\gamma$(-8)(Asn).

FIG. 20

Schematic representation of the isolation of fragment 6 which was used in the construction of plasmid pHis,-His-Xa-IFN-$\gamma$.

FIG. 21

Schematic representation of the construction of plasmid pHis,His-Xa-IFN-$\gamma$ by linking fragments 4. 5 and 6. Plasmid pHis,His-Xa-IFN-$\gamma$]codes for an IFN-$\gamma$ fusion protein having Met-His-His-Ala-Gly-Ile-Glu-Gly-Arg as an additional N-terminal amino acid sequence (His,-His-Xa-IFN-$\gamma$).

FIG. 22

Schematic representation of the construction and isolation of fragment 7 which was used in the construction of plasmid pHis,His-Ek-IFN-$\gamma$(-8).

FIG. 23

Schematic representation of the isolation of fragment 8 which was used in the construction of plasmids pHis,-His-Ek-IFN-$\gamma$(-8) and pHis,His-Xa-IFN-$\gamma$(-8)(Asn).

FIG. 24

Schematic representation of the construction of plasmid pHis-His-Ek-IFN-$\gamma$(-8) by linking fragments 5, 7 and 8. Plasmid pHis,His-Ek-IFN-$\gamma$(-8) codes for a IFN-$\gamma$ fusion protein which is shortened by 8 amino acids and which has Met-His-His-Ala-Gly-Asp-Asp-Asp-Asp-Lys as an additional N-terminal amino acid sequence (His,His-Ek- -IFN-$\gamma$(-8)).

FIG. 25

Schematic representation of the construction and isolation of fragment 9 which was used in the construction of plasmid pHis,His-Xa-IFN-γ(-8)(Asn).

FIG. 26

Schematic representation of the construction of plasmid pHis,His-Xa-IFN-γ(-B)(Asn) by linking fragments 5, 8 and 9. This plasmid codes for a IFN-γ fusion protein which is shortened at the C-terminus by 8 amino acids, which is lengthened at the N-terminus by the amino acid sequence Met-His-His-Ala-Gly-Ile-Glu-Gly-Arg and in which additionally at position 2 the amino acid Asp is replaced by the amino acid Asn (His,-His-Xa-IFN-γ(-8)- (Asn)).

FIG. 27

Schematic representation of the construction and isolation of fragment 10 which was used in the construction of plasmid p6xHis-DHFR.

FIG. 28

Schematic representation of the construction of plasmid p6xHis-DHFR by linking fragment 10 with the XhoI/BamHI fragment of plasmid pDS78/RBSII containing the replication region. Plasmid p6xHis-DHFR codes for a DHFR fusion protein having 6 histidines at the N-terminus [(His)$_6$-mDHFR].

FIG. 29

Schematic representation of the construction and isolation of fragment 11 which was used in the construction of plasmid p4xHis-DHFR.

FIG. 30

Schematic representation of the construction of plasmid p4xHis-DHFR by linking fragment 11 with the XhoI/BamHI fragment of plasmid pDS78/RBSII containing the replication region. Plasmid p4xHis-DHFR codes for a DHFR fusion protein having 4 histidines at the N-terminus [(His)$_4$- MDHFR].

FIG. 31

Schematic representation of the construction and isolation of fragment 12 which was used in the construction of plasmid pRBSII-6xHis.

FIG. 32

Schematic representation of the construction of plasmid pRBSII-6xHis by linking fragment 12 with the XbaI/BamHI fragment of plasmid pDS56/RBSII containing the replication region.

FIG. 33

Schematic representation of the construction and isolation of fragment 13 which was used in the construction of plasmid pRBSII-4xHis.

FIG. 34

Schematic representation of the construction of plasmid pRBSII-4xHis by linking fragment 13 with the XbaI/BamHI fragment of plasmid pDS56/RBSII containing the replication region.

FIG. 35

Schematic representation of the construction and isolation of fragment 14 which was used in the construction of plasmid pRBSII-2xHis.

FIG. 36

Schematic representation of the construction of plasmid pRBSII-2xHis by linking fragment 14 with the XbaI/BamHI fragment of plasmid pDS56/RBSII containing the replication region.

FIG. 37

Schematic representation of the construction of plasmid pDHFR-6xHis by linking the XbaI/BglII fragment of plasmid pDS78/RBSII containing the replication region with the BglII/XbaI fragment of plasmid pRBSII/6xHis containing the cat gene. Plasmid pDHFR-6xHis codes for a DHFR fusion protein having 6 histidines at the C-terminus [Met-mDHFR-(His)$_6$].

FIG. 38

Schematic representation of the construction of plasmid pDHFR-2xHis by linking the XbaI/BglII fragment of plasmid pDS78/RBSII containing the replication region with the BglII/XbaI fragment of plasmid pRBSII-2xHis containing the cat gene. Plasmid pDHFR-2xHis codes for a DHFR fusion protein having 2 histidines at the C-terminus [Met-MDHFR-(His)$_2$].

FIG. 39

Schematic representation of the construction of plasmid p4xHis-DHFR-4xHis by linking the XbaI/BglII fragment of plasmid p4xHis-DHFR containing the replication region with the BglII/XbaI fragment of plasmid pRBSII-4xHis containing the cat gene. Plasmid p4xHis-DHFR-4xHis codes for a DHFR fusion protein having in each case 4 histidines at the N- and at the C-terminus [(His)$_4$- mDHFR-(His)$_4$].

FIGS. 40A-B

Nucleotide sequence of the IFN-γ gene coded from plasmid pGLS and the amino acid sequence derived therefrom.

FIGS. 41A-B

Nucleotide sequence of the IFN-γ fusion gene coded from plasmid pHis,His-Xa-IFN-γ and the amino acid sequence derived therefrom.

FIGS. 42A-B

Nucleotide sequence of the IFN-γ fusion gene coded from plasmid pHis,His-Ek-IFN-γ(-8) and the amino acid sequence derived therefrom.

FIGS. 43A-B

Nucleotide sequence of the IFN-γ fusion gene coded from plasmid pHis,His-Xa-IFN-γ(-8)(Asn) and the amino acid sequence derived therefrom.

DESCRIPTION OF THE INVENTION

The affinity peptides can be linked directly or indirectly to the biologically active Polypeptide or protein. When a single affinity peptide is used, it can be linked either to the amino-terminal amino acid or to the carboxy-terminal amino acid of the biologically active Polypeptide or protein. When two affinity peptides are used, one of them is linked to the amino-terminal amino acid of the biologically active polypeptide or protein and the other is linked to the carboxy-terminal amino acid.

In the case of indirect linking, the affinity peptides contain a suitable selective cleavage site via which they are linked to the desired biologically active polypeptide or protein. Preferred selective cleavage sites have the amino acid sequence -(Asp)$_n$- Lys-, wherein n signifies 2, 3 or 4. or -Ile-Glu-Gly-Arg-, which are specifically recognized by the proteases enterokinase and coagulation factor X$_a$, respectively. Such affinity peptides can then be cleaved enzymatically, using methods known in the art.

In the case of direct linking, the affinity peptides remain linked with the desired biologically active polypeptide or protein and cannot be chemically or enzymatically cleaved. This type of linking is advantageous when the activity of the desired polypeptide or protein is not impaired by the presence of the affinity peptide. Such fusion proteins can be used for a number of immunological procedures. They can be used, for example, as reagents for detecting infectious diseases. Because they can be admixed with a physiologically compatible carrier material, they can also be used as vaccines for the prevention of diseases.

The term "biologically-active polypeptide or protein" as used herein means polypeptides or proteins which themselves are biologically active, or polypeptides or proteins which can be used for the preparation of biologically active polypeptides or proteins.

Biologically active polypeptides or proteins which can be used in this invention include, for example, malaria surface antigens, especially the 5.1 surface antigen, the CS protein and the p190 protein of *Plasmodium falciparum*, lymphokines, interferons, insulin and insulin precursors, HIV-1 and HIV-2 envelope and structural proteins, growth hormones and growth hormone releasing factors. Especially preferred biologically active polypeptides or proteins are those having the amino acid sequence of human immune interferon and partial sequences of human immune interferon, especially those having the amino acid sequences of the formulae:

Gln-Asp-Pro-Tyr-Val-Lys-Glu-Ala-Glu-Asn-Leu-Lys-Lys-Tyr-Phe-As n-Ala-Gly-His-Ser-Asp-Val-Ala-Asp-Asn-Gly-Thr-Leu-Phe-Leu-Gly-Ile-Leu-Lys-Asn-Trp-Lys-Glu-Glu-Ser-Asp-Arg-Lys-Ile-Met-Gln-Se r-Gln-Ile-Val-Ser-Phe-Tyr-Phe-Lys-Leu-Phe-Lys-Asn-Phe-Lys-Asp-Asp-Gln-Ser-Ile-Gln-Lys-Ser-Val-Glu-Thr-Ile-LYS-Glu-Asp-Met-As n-Val-Lys-Phe-Phe-Asn-Ser-Asn-Lys-Lys-Lys-Arg-Asp-Asp-Phe-Glu-Lys-Leu-Thr-Asn-Tyr-Ser-Val-Thr-Asp-Leu-Asn-Val-Gln-Arg-Lys-Al a-Ile-His-Glu-Leu-Ile-Gln-Val-Met-Ala-Glu-Leu-Ser-Pro-Ala-Ala-Lys-Thr-Gly-Lys-Arg-Lys-Arg-Ser-Gln-Met-Leu-Phe-Arg-Gly-Arg-Ar g-Ala-Ser-Gln.

Gln-Asp-Pro-Tyr-Val-Lys-Glu-Ala-Glu-Asn-Leu-Lys-Lys-Tyr-Phe-As n-Ala-Gly-His-Ser-Asp-Val-Ala-Asp-Asn-Gly-Thr-Leu-Phe-Leu-Gly-Ile-Leu-Lys-Asn-Trp-Lys-Glu-Glu-Ser-Asp-Arg-Lys-Ile-Met-Gln-Se r-Gln-Ile-Val-Ser-Phe-Tyr-Phe-Lys-Leu-Phe-Lys-Asn-Phe-Lys-Asp-Asp-Gln-Ser-Ile-Gln-Lys-Ser-Val-Glu-Thr-Ile-Lys-Glu-Asp-Met-As n-Val-Lys-Phe-Phe-Asn-Ser-Asn-Lys-Lys-Lys-Arg-Asp-Asp-Phe-Glu-Lys-Leu-Thr-Asn-Tyr-Ser-Val-Thr-Asp-Leu-Asn-Val-Gln-Arg-Lys-Al a-Ile-His-Glu-Leu-Ile-Gln-Val-Met-Ala-Glu-Leu-Ser-Pro-Ala-Ala-Lys-Thr-Gly-Lys-Arg-Lys-Arg-Ser-Gln-Met-Leu and Gln-Asn-Pro-Tyr-Val-Lys-Glu-Ala-Glu-Asn-Leu-Lys-Lys-Tyr-Phe-As n-Ala-Gly-His-Ser-Asp-Val-Ala-Asp-Asn-Gly-Thr-Leu-Phe-Leu-Gly-Ile-Leu-Lys-Asn-Trp-Lys-Glu-Glu-Ser-Asp-Arg-Lys-Ile-Met-Gln-Se r-Gln-Ile-Val-Ser-Phe-Tyr-Phe-Lys-Leu-Phe-Lys-Asn-Phe-Lys-Asp-Asp-Gln-Ser-Ile-Gln-Lys-Ser-Val-Glu-Thr-Ile-Lys-Glu-Asp-Met-As n-Val-Lys-Phe-Phe-Asn-Ser-Asn-Lys-Lys-Lys-Arg-Asp-Asp-Phe-Glu-Lys-Leu-Thr-Asn-Tyr-Ser-Val-Thr-Asp-Leu-Asn-Val-Gln-Arg-Lys-Al a-Ile-His-Glu-Leu-Ile-Gln-Val-Met-Ala-Glu-Leu-Ser-Pro-Ala-Ala-Lys-Thr-Gly-Lys-Arg-Lys-Arg-Ser-Gln-Met-Leu, and those having the amino acid sequence of mouse dihydrofolate reductase.

The preparation of the fusion proteins of this invention can be carried out using standard recombinant DNA methods. Preferably, a nucleotide sequence coding for the desired affinity peptide is first synthesized and then linked to a nucleotide sequence coding for the desired biologically active polypeptide or protein.

The thus-obtained hybrid gene can be incorporated into expression vectors such as plasmid pDS8/RBSII, SphI; pDS5/RBSII,3A+5A; pDS78/RBSII; pDS56/RBSII or other commercial or generally accessible plasmids, using standard methods. Most of the requisite methodology can be found in Maniatis et al., "Molecular Cloning", Cold Spring Harbor Laboratory, 1982, which is hereby incorporated by reference to illustrate the state of the art.

Methods for the expression of the fusion proteins of this invention are also described by Maniatis et al., supra. They embrace the following procedures:

(a) Transformation of a suitable host organism, preferably *E. coli*, with an expression vector in which the hybrid gene is operatively linked to an expression control sequence;

(b) Cultivation of the transformed host organism under suitable growth conditions; and (c) Extraction and isolation of the desired fusion protein from the host organism.

Host organisms that can be used include but are not limited to gram-negative and gram-positive bacteria such as *E. coli* and *B. subtilis* strains. *E. coli* strain M15 is especially preferred. Other *E. coli* strains that can be used include, e.g., *E. coli* 294 (ATCC No. 3144), *E. coli* RR1 (ATCC No. 31343) and *E. coli* W3110 (ATCC No. 27325).

Ideal metal chelate resins for the purification of the fusion proteins of the invention are nitrilotriacetic acid (NTA) resins of the general formula:

Carrier matrix-spacer—NH—$(CH_2)_x$—CH(COOH)——$N(CH_2COO^-)_2 Ni^{2+}$, wherein x signifies 2. 3 or 4.

Carrier matrices that can be used include, e.g.. materials used in affinity and gel chromatography such as cross-linked dextrans, agarose (especially in the form known under the trademark Sepharose®) or polyacrylamides.

Suitable spacer groups include these known in the field of affinity chromatography, with the groups —O—$CH_2$—CH(OH)—$CH_2$— and —O—CO— being preferred.

An especially preferred NTA resin for the purification of the hybrid proteins of this invention has the formula:

[Sepharose ®CL 6B]-O—CH$_2$—CH(OH)—CH$_2$—NH—(CH$_2$)$_4$—CH(COOH)—N(CH$_2$COO$^-$)$_2$Ni$^{2+}$.

The NTA resin can be used batch-wise or in continuously operating columns to purify the fusion proteins. Prior to loading with the fusion protein, the NTA resin is equilibrated with an aqueous buffer which itself does not form chelates with nickel, preferably a Tris.HCl buffer. pH 7.5. The equilibration buffer (and the elution buffer) can contain a denaturing agent or a detergent such as guanidine.HCl, urea or Triton. The addition of such a denaturing agent or detergent permits problem-free operations even with fusion proteins which are poorly soluble in aqueous solution.

The elution of the fusion proteins from the column can be carried out at a constant pH or with linear or discontinuously falling pH gradients. The optimal elution conditions depend on the amount and type of impurities which are present, the amount of material to be purified, the column dimensions etc. and are easily determined by routine experimentation on a case-by-case basis.

EXAMPLES

The following Examples illustrate the preparation of fusion proteins of the invention, their purification by means of metal chelate chromatography and the preparation of biologically active polypeptides or proteins by enzymatic cleavage of the purified fusion proteins in accordance with the invention.

Example 1

Description of Plasmids Used In the Construction of Plasmids pGLS, pHis,His-Xa-IFN-γ, P-His,His-Ek-IFN-γ(-8), pHis,His-Xa-IFN-γ(-8)(Asn), p6xHis-DHFR, p4xHis-DHFR-4xHis, pDHFR-2xHis and pDHFR-6xHis

A. Principles

Plasmids pDS8/RBSII,SphI (FIGS. 1 and 2). pDS5/RBSII,3A+5A (FIGS. 3 and 4A-C), pDS78/RBSII (FIGS. 5 and 6A-D) and pDS56/RBSII (FIGS. 7 and 8A-C) were used for the construction of the specified plasmids. E. coli cells transformed with these plasmids were deposited at the Deutsche Sammlung von Microorganism in Grisebachstrasse 8, D-3400 West Germany Göttingen (on Nov. 21, 1987 in Braunschweig) on Oct. 3. 1985 [E. coli M15 (pDS5/RBSII,3A+SA; pDMI,1), DSM No.: 3517], on Aug. 6, 1986 (E. coli M15 (pDS8/ RBSII,SphI; pDMI,1), DSM No.: 3809], on Sep. 3, 1987 (E. coli M15 (pDS78/RBSII; pDMI,1). DSM No.: 4232). and on Dec. 23, 1987 (E. coli M15 (pDS56/RBSII; pDMI,1), DSM No.: 4330]. in accordance with the Budapest Treaty.

The above-mentioned vectors contain the regulatable promoter/operator element P$_{N25x/O}$ (Stüber et al., EMBO J. 3. 3143-3148 (1984)) or N25OPSN25OP29 and the ribosomal binding sites RBSII,SphI, RBSII,-3A+5A or RBSII. These ribosomal binding sites were derived from the ribosomal binding site of the promoter PG25 of the E. coli phage T5 (R. Gentz, Dissertation, Universität Heidelberg, BRD [1984]) and were obtained via DNA synthesis.

The high efficiency of expression of the above-mentioned plasmids can be maintained in E. coli cells only if the promoter/operator element is repressed by the binding of a lac repressor to the operator. The lac repressor is coded in the lacI gene. P$_{N25X/O}$ and N25OPSN-25OP29 can be repressed efficiently only when a sufficient number of repressor molecules is present in the cells. Therefore, the lacI$^q$ allel, which contains a promoter mutant which leads to an increased expression of the repressor gene, was used. This lacI$^q$ allel is present in the plasmid pDMI,l (FIGS. 9 and 10A-C).

This plasmid carries, in addition to the lac-I gene, the neo gene, which confers kanamycin resistance to the bacteria and which is used as the selection marker. pDMI,l is compatible with the aforementioned plasmids. E. coli cells which are transformed with such expression vectors must contain pDMI,l to guarantee that the expression vector is held stable in the cells. An induction of this system is achieved by adding IPTG to the medium at the desired cell density.

B. Plasmid pDS8/RBSII,SDhI

The part of pDS8/RBSII,SphI (FIGS. 1 and 2A-B) which lies between the restriction cleavage sites for XbaI and XhoI and which contains the replication region and the gene for βlactamase (which confers ampicillin resistance to the cells) was derived from the plasmid pBR322 (Bolivar et al., Gene 2, 95-113 [1977]); Sutcliffe, Cold Spring Harbor Symp. Quant. Biol. 43, 77-90 [1979]). The remaining part of the plasmid carries the regulatable promoter/operator element P$_{N25X/O}$ (Stüber et al., supra) followed by the ribosomal binding site RBSII, SphI, which is part of a EcoRI/BamHI fragment; the dihydrofolate reductase (DHFR) gene of mouse cell line AT-3000 (Chang et al., Nature 275, 617-624 (1978); Masters et al., Gene 21, 59-63 [1983]); the terminator t$_o$ of E. coli phage lambda (Schwarz et al., Nature 272, 410-414 [1978]); the promoter-free gene of chloramphenicol acetyl-transferase (Marcoli et al., FEBS Letters, 110, 11-14 [1980]) and the terminator T1 of the E. coli rrnB operon (Brosius et al., J. Mol. Biol., 148, 107-127 (19811).

C. Plasmid pDS5/RBSII,3A+5A

The part of pDS5/RBSII,3A+5A (FIGS. 3 and 5A-C) which lies between the cleavage sites for the restriction enzymes XbaI and XhoI and which contains the replication region and the gene for β-lactamase (which confers ampicillin resistance to the cells) was derived originally from the plasmid pBR322 (Bolivar et al., supra; Sutcliffe, supra). However, the gene for β-lactamase is modified by elimination of the cleavage sites for the restriction enzymes HincII and PstI. These alterations in the DNA sequence have no effect on the amino acid sequence of the β-lactamase. The remaining part of the plasmid carries the regulatable promoter/operator element P$_{N25X/O}$ (Stüber et al., supra) followed by the ribosomal binding site RBSII,3A+5A, which is part of a EcoRI/BamHI fragment; cleavage sites for the restriction enzymes SalI,PstI and HindIII; the promoter-free gene for chloramphenicol acetyltransferase (Marcoli et al., supra) and the terminator T1 of the E. coli rrnB operon (Brosius et al., supra).

D. Plasmid pDS78/RBSII

The part of pDS78/RBSII (FIGS. 5 and 6A-D) which lies between the restriction cleavage sites for XbaI and XhoI and which contains the replication region and the gene for β-lactamase (which confers ampicillin resistance to the cells) was derived originally from the plasmid pBR322 (Bolivar et al., supra; Sutcliffe, supra). However, the gene for β-lactamase is modified in the manner described for the plasmid pDS5/RBSII,-3A+5A. The remaining part of the plasmid carries the regulatable promoter/operator element N25OPSN-25OP29 followed by the ribosomal binding site RBSII, which is part of a EcoRI/BamHI fragment; the gene for dihydrofolate reductase of the mouse cell line AT-3000 (Chang et al., supra; Masters et al., supra), which has been altered by introducing a cleavage site for the restriction enzyme BglII immediately prior to the end of the structural gene; the terminator $t_o$ (Schwarz et al., supra); the promoter-free gene for chloramphenicol acetyltransferase (Marcoli et al., supra) and the terminator T1 (Brosius et al., supra).

E. Plasmid pDS56/RBSII

Plasmid pDS56/RBSII (FIGS. 7 and 8A-C) is very similar to plasmid pDS5/RBSII,3A+5A but contains the regulatable promoter/operator element N25OPSN-25OP29 and the ribosomal binding site RBSII as expression signals. In addition, pDS56/RBSII contains the terminator $t_o$ of the E. coli phage lambda (Schwarz et al., supra).

F. Plasmid pDMI,1

Plasmid pDMI,1 (FIGS. 9 and 10A-C) carries the gene for neomycin phosphotransferase from the transposon Tn5 (Beck et al., Gene 19, 327-336 [1382]), which confers kanamycin resistance to the E. coli cells, and the lacI gene (Farabough, Nature 274, 765-769 [1978]) with the promoter mutation $I^1$ (Calos, Nature 274, 762-765 [1978]), which codes for the lac repressor. Moreover, plasmid pDMI,1 contains a region of the plasmid pACYC184 (Chang and Cohen, J. Bacteriol. 134, 1141-1156 [1978]), which contains all information required for the replication and stable transmission to the daughter cells.

Example 2

Description of DNA Adapters Used In the Construction of the Various Plasmids

A. Principles

To adapt the ribosomal binding site RBSII, SphI on the gene for immune interferon (IFN-γ), to shorten this gene, to link IFN-γ and IFN-γ fragments such as, e.g., IFN-γ(-8) with an affinity peptide and to express DHFR fusion proteins having at least two neighbouring histidine residues, oligonucleotides were chemically synthesized and, after workup, phosphorylated. The nucleotide sequences of the adaptors used are shown as double-stranded DNA sequences in FIGS. 11A-B.

B. Synthesis and Workup of the Oligonucleotides

The oligonucleotides were prepared simultaneously on a multisynthesis apparatus (described in European Patent Application No. 181, published May 21, 1985), with glass of defined pore size (CPG) used as the carrier material (Kiefer et al., Immuno. Meth. 3, 69-83 [1985]; Sproat et al., Tetrahedr. Lett. 24 5771-5774 [1983]; Adams et al., J. Amer. Chem. Soc.. 105, 661-663 [1985]. The lyophilized oligonucleotides were taken up in water and dissolved at 4° C. for 1 hour. The DNA concentration was 100 nmoles/ml.

C. Phosphorylation of the Oligonucleotides

In each case, 150 pmol of the oligonucleotides were incubated in separate batches at 37° C. for 20 minutes in 20 μl of 50 mM Tris HCl, pH 8.5, and 10 mM MgCl$_2$ with 2 pmol of γ[$^{32}$P]-ATP (Amersham, Braunschweig; 5000 Ci/mmol) and 1 unit (U) of T$_4$polynucleotide kinase (Gibco-BRL, Basle). Subsequently, 5 nmol of ATP were added, and after a further 20 minutes at 37° C., the reaction was terminated by heating to 65° C. The phosphorylated oligonucleotides produced were used without any further workup.

Example 3

Construction of Plasmid pGLS

A. Principles

Figure 12:
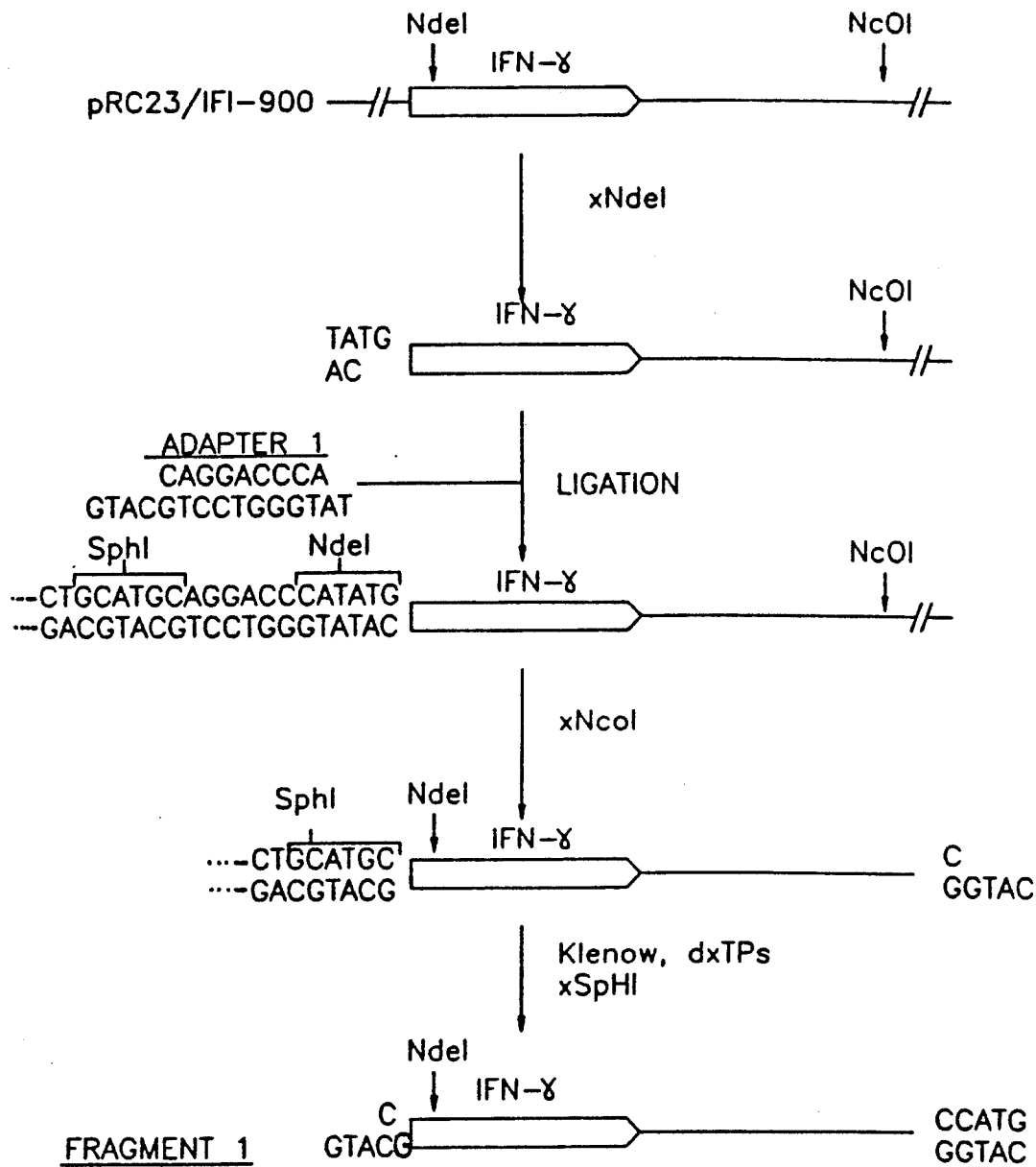
Figure 13:
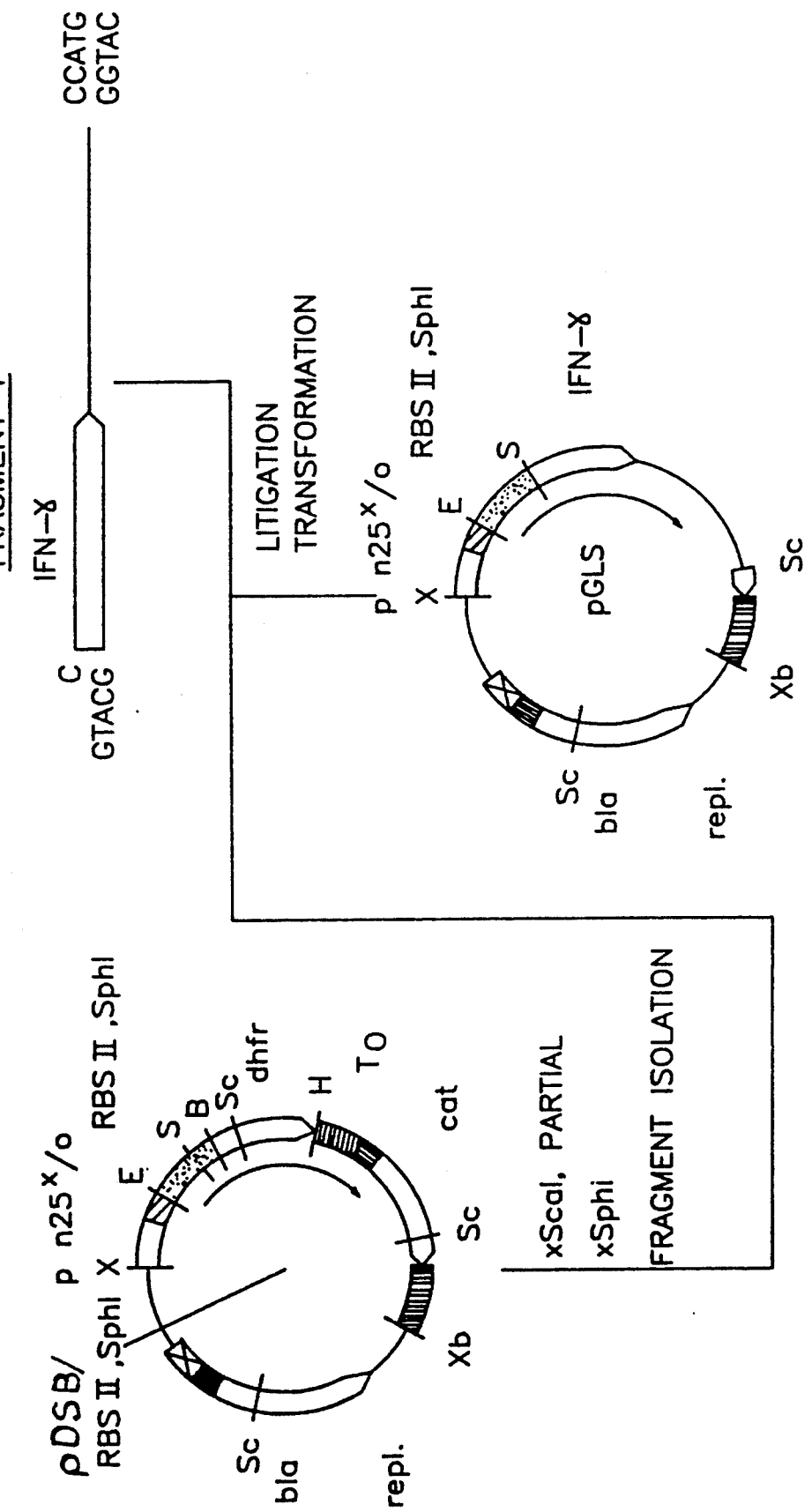

For the construction of plasmid pGLS, the IFN-γ gene was first bonded (FIG. 12) to adaptor 1 (FIGS. 11A-B) and isolated. Subsequently, the resulting fragment 1 was integrated into plasmid pDS8/RBSII,SphI (FIG. 13).

B. Preparation of Fragment 1

4 μg of plasmid pRC23/IFI-900 (European Patent Application publication No. 99084, published Jan. 25, 1984) having a DNA concentration of 400 μg/ml were digested with 10 units of the restriction endonuclease NdeI in core buffer (50 mM Tris HCl, pH 8, 10 MM MgCl$_2$, 50 mM NaCl) for 1 hour at 37° C. (volume 20 μl). The sample was subsequently extracted once with phenol, the remainder of the phenol was removed with ether and the DNA was finally precipitated with 66% alcohol and 0.3M potassium acetate. The sediment was dried for 2 minutes in a Speed-vac concentrator and dissolved in T4 ligase buffer (50 mM Tris HCl, pH 7.8, 10 mM MgCl$_2$, 10 mM DTT, 500 μm ATP).

25 pmol of the phosphorylated adaptor 1 (FIGS. 11A-B) were dissolved in 1x ligase buffer and added to this reaction mixture so that a total volume of 25 μl was achieved. The ligation was carried out for 3 hours at 22° C., with 1 μl of DNA ligase (1 White unit, Boehringer Mannheim) being used. The ligation was terminated by heating the sample to 65° C. for 7 minutes.

The DNA was precipitated with alcohol, dried as described above and then dissolved in 50 μl of NcoI digestion buffer (50 mM Tris HCl, pH 8, 10 mM MgCl$_2$, 50 mM NaCl. 50 mM KCl). 10 units of NcoI were added thereto and the sample was incubated for 1 hour at 37° C. The enzyme was subsequently inactivated by heating the sample to 650° C. for 7 minutes.

After a phenol extraction the DNA was precipitated as described above and the sediment was dried. The DNA was dissolved in Klenow buffer (50 mM Tris HCl, pH 7.2, 10 mM MgSO$_4$, 100 μM DTT), dATP, dGTP, dCTP and dTTP (final concentration in each case 100 μM) and 1 unit of Klenow enzyme (Boehringer, Mannheim) were added thereto and the sample was held for 1 hour at 22° C. The reaction was terminated by the addition of 2 μl of 0.25 M EDTA, the sample was extracted with phenol, the DNA was precipitated with alcohol as described and dissolved in SphI digestion buffer (50 mM Tris HCl, pH 7.5, 6 mM MgCl$_2$, 50 mM NaCl, 6 mM 2-mercaptoethanol).

After the addition of 10 units of SphI the sample was incubated for 1 hour at 37° C. the digestion was terminated by heating as described, a phenol extraction was carried out and the DNA was precipitated with alcohol and dried.

The DNA sediment was dissolved in 10 µl of sample buffer and the DNA fragments were separated in a 6% polyacrylamide gel (elution buffer; 40 mm Tris HCl, 20 mM Na acetate, 2 mM EDTA, pH 7.8). DNA of phage φX (Gibco-BRL, Basle) digested with HaeIII was used as the molecular weight standard. The DNA was stained with ethidium bromide (0.5 µg/ml), made visible with UV light (300 nm wavelength), and the IFN-γ coding band was cut out from the gel with a scalpel.

The piece of gel was transferred into a pocket of size 4×4 mm in an agarose gel (0.7% agarose gel, running buffer: 90 mM Tris borate, 90 mM boric acid, 3 mM EDTA, pH 8.3). The pocket was closed with 0.7% liquid agarose in 1xTBE in order to achieve a homogeneous electrical field. A portion of a NA45 membrane (Schleicher and Schüll, Dassel, BRD) was placed in front of the sample and the DNA was electrophoretized onto the membrane (5 minutes, 15 V/cm).

After washing with distilled water, the membrane was transferred into an Eppendorf test tube which contained 250 µl of 1.5M lithium acetate, 50 mM Tris HCl, pH 8, and 10 mM EDTA. The DNA was eluted for 20 minutes at 65° C. The membrane strip was removed from the test tube and the sample was extracted once with 200 µl of phenol (pH 8). The DNA was precipitated after the addition of 20 µl of 5M lithium acetate and 440 µl of isopropanol, and the sediment was washed with 80% ethanol and dried. Subsequently, the sediment was dissolved in 10 µl of TE buffer (10 mM Tris HCl, pH 7.6, 1 mM EDTA). The DNA fragment produced was designated fragment 1 (FIG. 12).

C. Preparation of Plasmid pDS8/RBSII,SphI 2 pmol of plasmid pDS8/RBSII,SphI were cleaved with the restriction enzyme SphI. Thereafter, the resulting linear plasmid DNA was incubated with a limited amount of the restriction enzyme ScaI, whereby the DNA was cleaved only at approximately 50% of the ScaI cleavage sites present. The sample was extracted with phenol and then with ether, and the DNA was precipitated as described above. The sediment was dried and dissolved in 20 µl of buffer (5 mM Tris HCl, pH 8), and 1 U of CIP (calf intestinal phosphatase, Boehringer Mannheim) was added.

The sample was incubated for 1 hour at 37° C., the enzyme was removed by a phenol extraction and the DNA was precipitated. After dissolving the DNA, the ScaI/SphI fragment, which contained part of the cat gene, the terminator T1, the replication region, the bla gene, the promoter N25x/o and the ribosomal binding site RBSII,SphI, was isolated from a 1% agarose gel and transferred electrophoretically to a NA45 membrane as described above. Elution of the DNA, alcohol precipitation and dissolution in 10 µl of TE buffer were also carried out as described above. Approximately 1 pmol of the desired vector fragment was obtained.

D. Assembly of Plasmid pGLS 0.05 pmol of the pDS8/RBSII, SphI vector fragment were ligated as described above with 0.05 pmol of insert DNA (fragment 1) in ligase buffer. A control ligation without insert DNA was carried out in parallel. E. coli M15 cells containing plasmid pDMI,1 were prepared for the transformation according to the method of Morrison (Methods Enzymol. 68, 326-331 [1979]). After heating for 7 minutes at 65° C., the ligation mixtures were added to 200 µl of these competent cells. The samples were maintained for 30 minutes on ice, incubated for 2 minutes at 420° C. and, after the addition of 0.5 ml of LB medium. incubated for 90 minutes at 370° C.

The cells were then plated-out on LB agar plates which contained 100 µg/ml ampicillin and 25 µg/ml kanamycin and incubated overnight at 37° C. The transformation of the control ligation gave no transformants. The ligation with fragment 1 on the other hand gave about 200 colonies.

Individual colonies were picked with a sterile toothpick, transferred into a test tube which contained 10 ml of LB medium with 100 µg/ml ampicillin and 25 µg/ml kanamycin and maintained for 12 hours in a shaking incubator. Thereafter, the cells were sedimented and the plasmid DNA was isolated according to the method of Birnboim and Doly (Nucleic Acids Res. 7. 1515-1523 (1979]).

In each case, 1 µg of the isolated plasmids was digested with SphI and XbaI to determine whether a fragment which contained the IFN-γ gene and the terminator T1 was present in these plasmids. All analyzed DNA samples contained the mentioned DNA fragment of about 1 kb. These plasmids were designated pGLS (FIG. 13).

E. Sequence Analysis of the IFN-γ Gene Integrated Into pGLS

To determine whether the correct IFN-γ sequence is present in plasmid pGLS, the double-stranded circular plasmid DNA was sequenced, with a starter sequence (primer) labelled with [γ-$^{32}$P]-ATP being used. This starter sequence contains the nucleotides of position 199-218 of the plasmid pDS8/RBSII,SphI and ends 6 nucleotides before the ATG of the SphI cleavage site.

0.3 pmol of the isolated plasmid DNA was precipitated with alcohol, the sediment was washed once with 80% ethanol, dried and finally dissolved in 8 µl of ¼ TE buffer. After the addition of 2 pmol of the starter sequence, the sample was incubated for 5 minutes at 42° C. The DNA was then sequenced according to the method of Sanger et al. (Proc. Natl. Acad. Sci. USA 74, 5463-6567 1977]). As a radioactively labelled "primer" was used, all reactions were carried out with unlabelled deoxynucleotide triphosphates. The DNA sequence analysis indicated that the correct IFN-γ sequence had been integrated into plasmid pGLS (for amino acid sequence, see FIG. 40).

Example 4

Construction of Plasmid pIFN-γ(-8)

A. Principles

Figure 14:
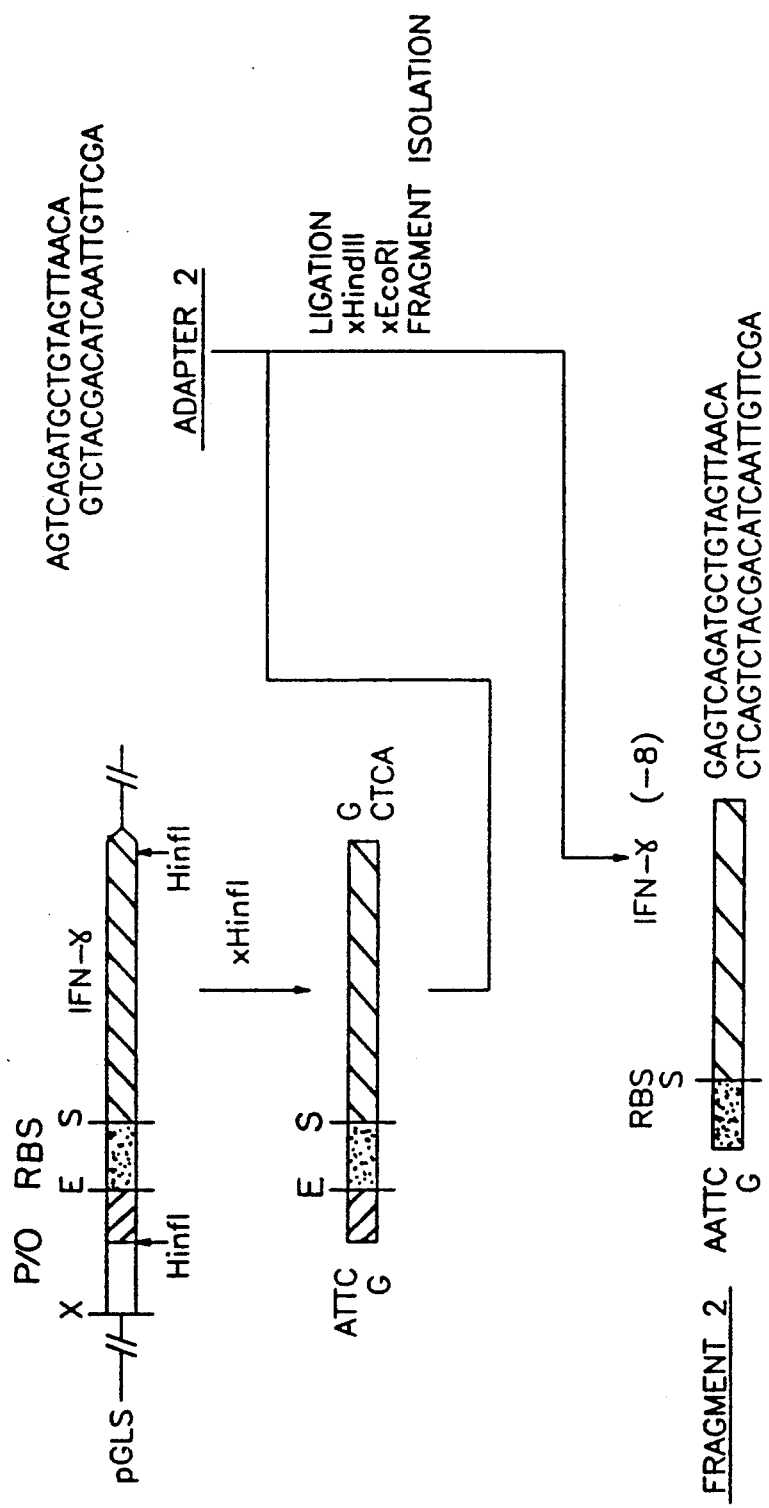
Figure 15:
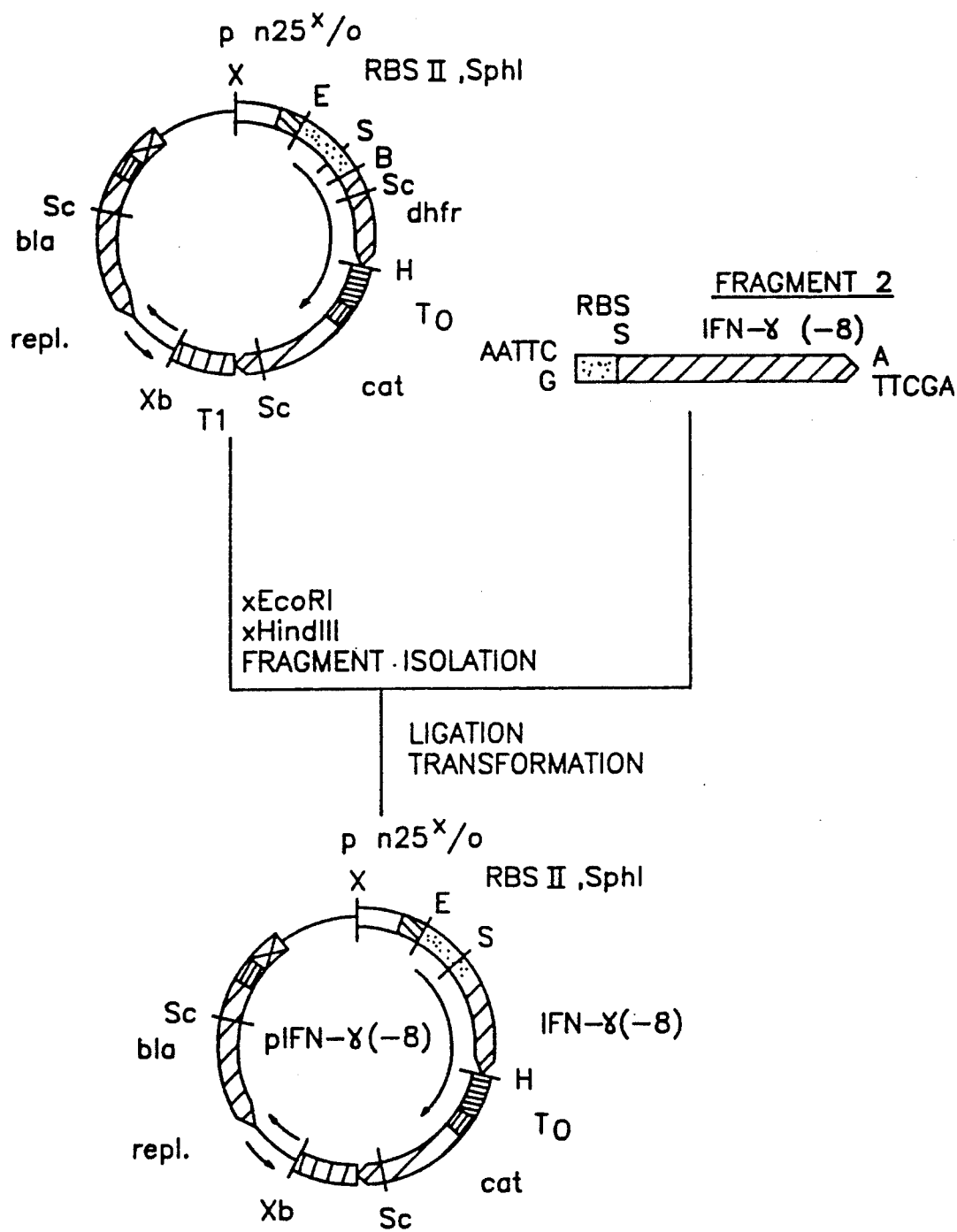

For the construction of plasmid pIFN-γ(-8), adaptor 2 (FIGS. 11A-B) was first linked to the individual HinfI cleavage site in the IFN-γ gene. Because of a translation stop codon in this adaptor, the C-terminal region of the IFN-γ protein is shortened by 8 amino acids (FIG. 14). The resulting fragment 2 was subsequently integrated into plasmid pDS8/RBSII,SphI (FIG. 15).

B. Preparation of Fragment 2

3 pmol of plasmid pGLS were digested with 15 U of HinfI (50 µl volume, 1 hour, 37° C.). The restriction enzyme was subsequently inactivated (7 min. at 65° C.), the sample was extracted with phenol, extracted with ether, precipitated with potassium acetate and alcohol and dried.

The sediment was dissolved in 50 μl of ligase buffer. 100 pmol of phosphorylated oligonucleotide (adaptor 2) were mixed with 10 μl of HinfI-cleaved plasmid pGLS and, after the addition of 25 μl of ligase buffer and 1 U of T4-DNA ligase, incubated for 12 hours at 22° C. As described above, the reaction was terminated by heating the sample and the DNA was precipitated.

A digestion with the restriction enzymes EcoRI (15U) and HindIII (20U) for 20 hours at 37° C. was then carried out. After heat inactivation, phenol extraction, extraction with ether and alcohol precipitation, the sample was dissolved in 10 μl of sample buffer and the DNA fragments were separated in a 6% polyacrylamide gel. After staining with ethidium bromide the DNA bands were made visible under UV light (300 nm). The band which contained the IFN-γ gene was cut out from the gel with a sterile scalpel and electrophoresed as described above onto a NA45 membrane. The DNA was eluted and designated fragment 2 (FIG. 14).

C. Preparation of Plasmid DDS8/RBSII,SphI 2 pmol of plasmid pDS8/RBSII,SphI were digested with 10 U of EcoRI and 10 U of HindIII for 1 hour at 37° C., in a volume of 50 μl. After heat inactivation of the enzyme and acohol precipitation the DNA sediment was dissolved in 10 μl of sample buffer. After electrophoreses in a 1% agarose gel the EcoRI/HindIII fragment which contained the terminator $t_o$, the cat gene, the terminator T1, the replication region, the bla gene and the promoter $P_{N25x/O}$ was cut out from the gel and eluted as described above.

D. Assembly of Plasmid pIFN-γ(-8)

10 μl of the isolated EcoRI/Hind III vector fragment and half of the isolated fragment 2 were incubated (20° C. 3 hours) with 1 U of T4 ligase. A control ligation without the addition of fragment 2 was carried out in parallel. The ligations were terminated by heating the samples as previously described.

The transformations were carried out according to the method of Morrison (supra), with *E. coli* strain M15, which contained the plasmid pDMI.1, being used. The cells were plated-out on LB agar plates which contained 100 μg/ml ampicillin and 25 μg/ml kanamycin. The plates were held for 15 hours at 370° C. in an incubator.

No transformants were found on the control plates, but the ligation in which the vector DNA and fragment 2 were used gave about 500 colcnies. Individual colonies were picked with a sterile toothpick, transferred into 100 ml of LB medium and left to grow as described. The plasmid DNA was isolated according to the method of Birnboim and Doly (supra). In each case 4 μl of the plasmid DNA, is isolated and dissolved in TE buffer, were cleaved as described above with 2 U of EcoRI and HindIII. A fragment with the desired length of about 450 bp could be cut out from all tested plasmids. These plasmids were designated pIFN-γ(-8) (FIG. 15).

E. Sequence Analysis of Plasmid pIFNγ(-8)

Sequence analysis was carried out as described in Example 3. However, an oligonucleotide which contained the nucleotides of position 928-896 of the plasmid pDS8/RBSII,SphI and which therefore permitted the sequencing of DNA fragments which were integrated in front of the terminator $t_o$ was used as the starter sequence. The sequence analysis confirmed the desired sequence of IFN-γ gene which codes for a IFN-γ protein shortened by 8 amino acids (at the carboxyl end).

Example 5

Construction of Plasmid pDS8/RBSII,SphI-His,His-Xa-BamHI

A. Principles

Figure 16:
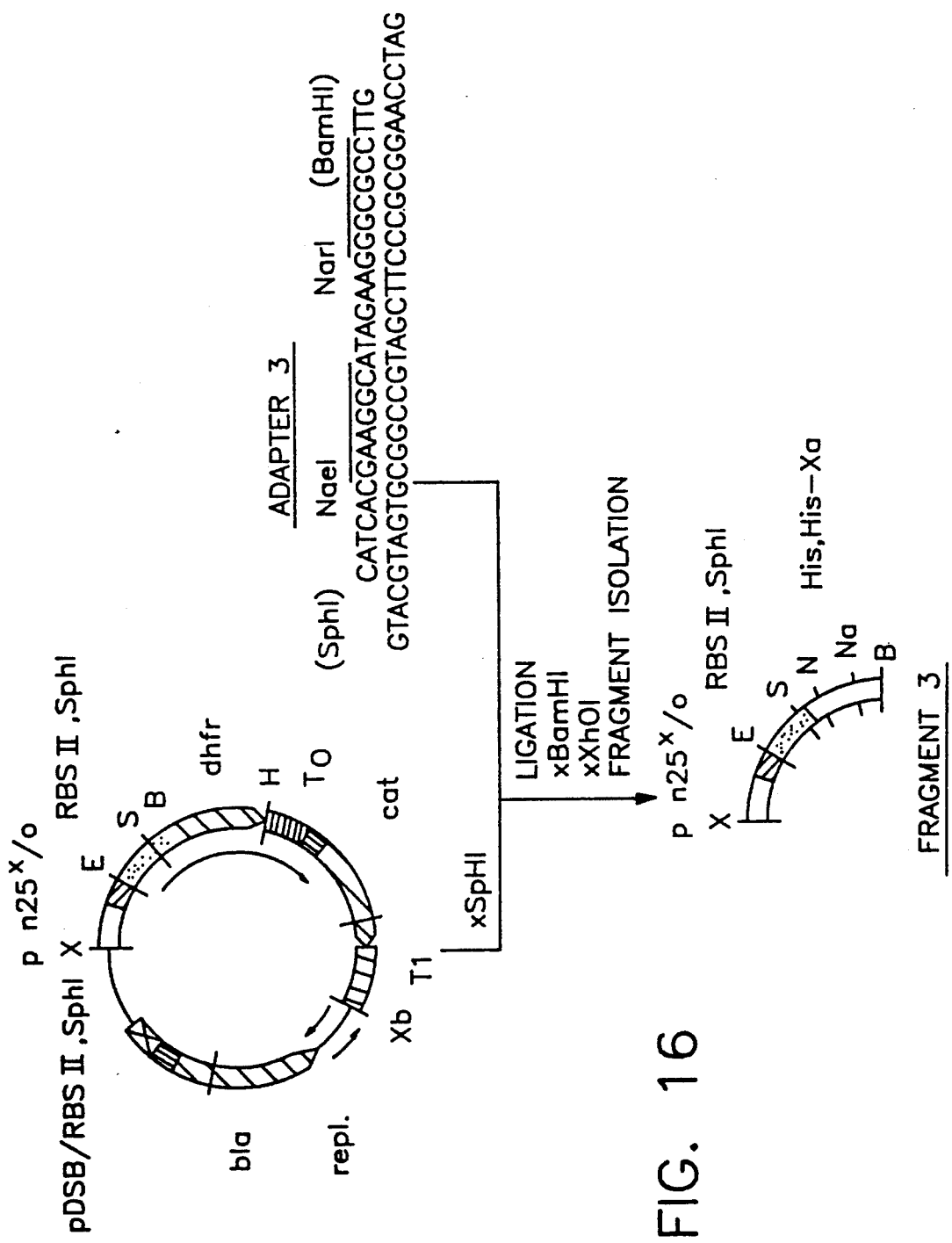
Figure 17:
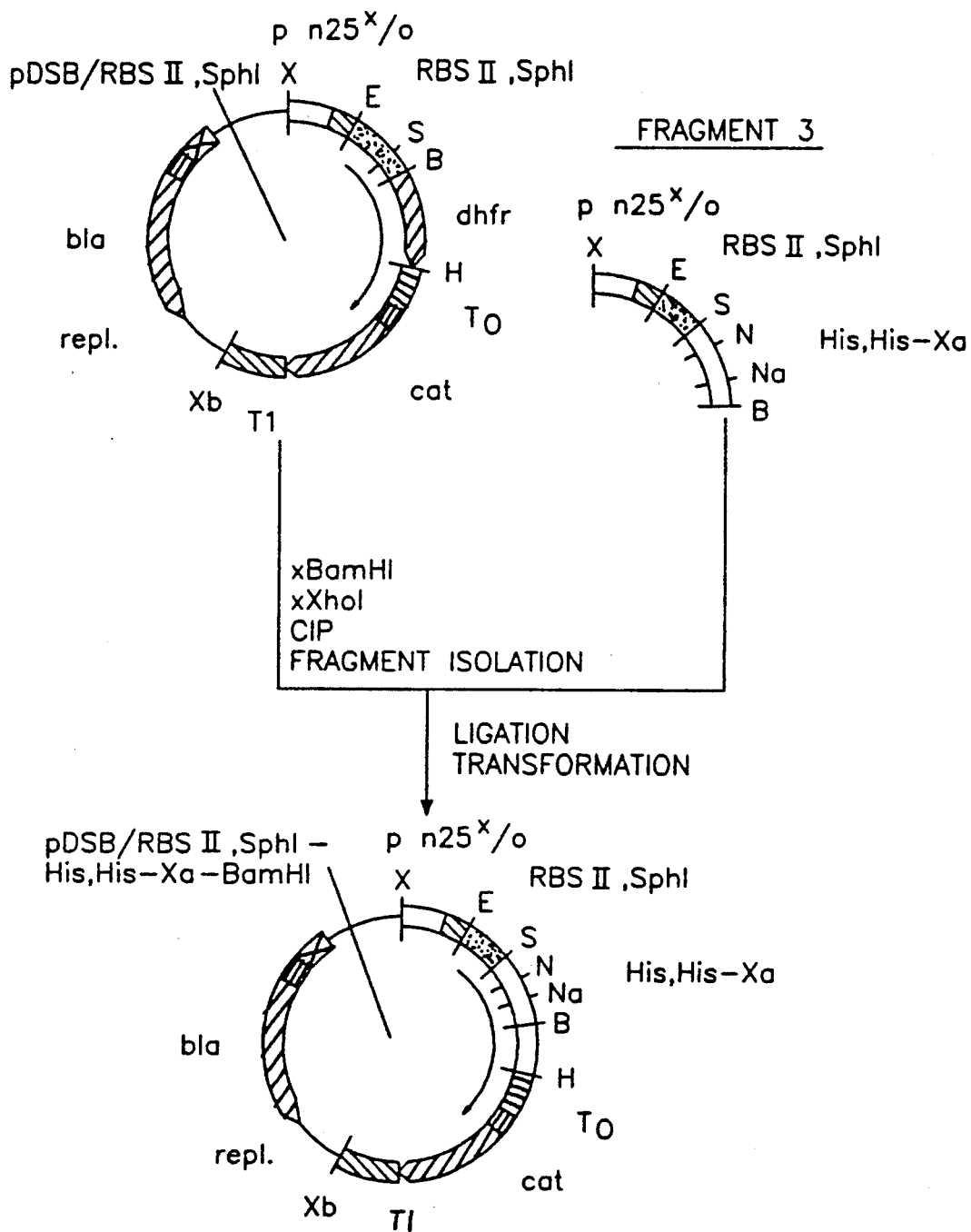

For the construction of plasmid pDS8/RBSII,SphI-His,His-xa-BamHI, adaptor 3 (FIGS. 11A-B), which codes for an affinity peptide which contains two neighbouring histidines and a cleavage site of factor Xa was linked with the ribosomal binding site RESII,SphI. Subsequently, fragment 3 (FIG. 16) containing the promoter $P_{N25X/O}$ and the said affinity peptide was isolated and integrated into plasmid pDS8/RBSII,SphI (FIG. 17).

B. Preparation of Fragment 3

2 pmol of plasmid pDS8/RBSII,SphI were cleaved with the restriction enzyme SphI. The reaction was terminated by incubation at 65° C. for 7 minutes, the sample was extracted with phenol, extracted with ether and the DNA was precipitated with alcohol and potassium acetate. The sediment was taken up in 10 μl of ligase buffer, 25 pmol of phosphorylated adaptor 3 (FIGS. 11A-B) dissolved in ligase buffer were added, and after the addition of 1 U of T4 DNA ligase, incubated for 3 hours at 22° C. The reaction was terminated by heating (7 minutes. 65° C.). and after a phenol extraction and subsequent treatment with ether, the DNA was precipitated with alcohol and potassium acetate. The sediment was dissolved in 30 μl of buffer, in each case 10 U of the restriction enzymes BamHI and XhoI were added and the mixture was incubated at 37° C. for 2 hours. Subsequently, 3.5 μl of 10-fold concentrated sample buffer for polyacrylamide gels-were added to the sample and the mixture was incubated for 7 minutes at 65° C. The DNA was separated in a 6% polyacrylamide gel, and the fragment liberated by XhoI and BamHI was cut out with a scalpel. The DNA was eluted as described and designated fragment 3 (FIG. 16).

C. Preparation of Plasmid pDS8/RBSII,SphI 2 pmol of plasmid pDS8/RBSII,SphI were cleaved with 10 U each of the restriction enzymes BamHI and XhoI. After heat inactivation of the enzyme, the sample was extracted with phenol, extracted with ether and the DNA was precipitated with alcohol and potassium acetate. The sediment was re-suspended in 50 μl of 50 mM Tris HCl, pH 8. 1 U of CIP (see above) was added, and the sample was o incubated at 37° C. for 30 minutes. After heat inactivation of the enzyme, the DNA was separated in a 6% polyacrylamide gel after the addition of sample buffer, and the plasmid body was eluted from the gel as described.

D. Assembly of Plasmid pDS8/RBSII,SphI-His,His-Xa-BaMHI

The above-described fragment 3 was ligated with the vector body (22° C., 2 U of T4 DNA ligase, 25 μl of ligase buffer). A control ligation without the addition of fragment 3 was carried out in parallel. The ligation batches were transformed as described above into *E.* coli strain M15 which contained the plasmid pDMI.1 and plated out on LB plates with 100 μg/ml ampicillin and 25 μg/ml kanamycin. The transformation of the control ligation gave no transformants but the transformation of the ligation batch with fragment 3 gave about 100 colonies.

Individual colonies were grown up in 100 ml of LB medium as described above and the plasmid DNA was isolated according to the method of Birnboim and Doly (supra). All plasmids contained the cleavage sites for NaeI and NarI (see FIG. 17) newly introduced by the adaptor. Sequence analysis of the plasmid DNA carried out as described above (Example 3, E) confirmed that adaptor 3 had been correctly integrated into the vector. These plasmids were designated pDS8/RBSII,SphI-His,His-Xa-BamHI (FIG. 17).

Example 6

Construction of Plasmid pHis,His-Xa-IFN-γ

A. Principles

Figure 18:
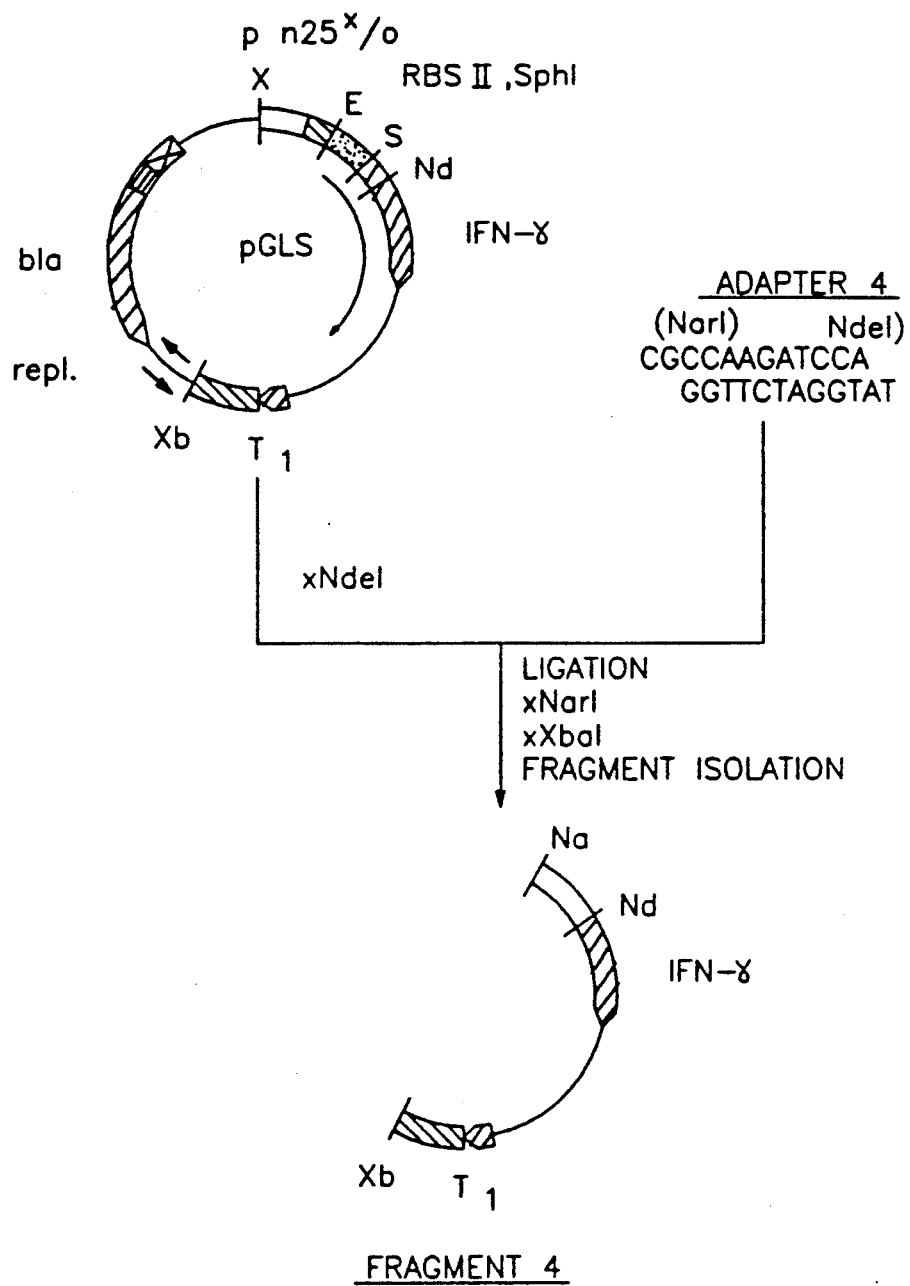
Figure 19:
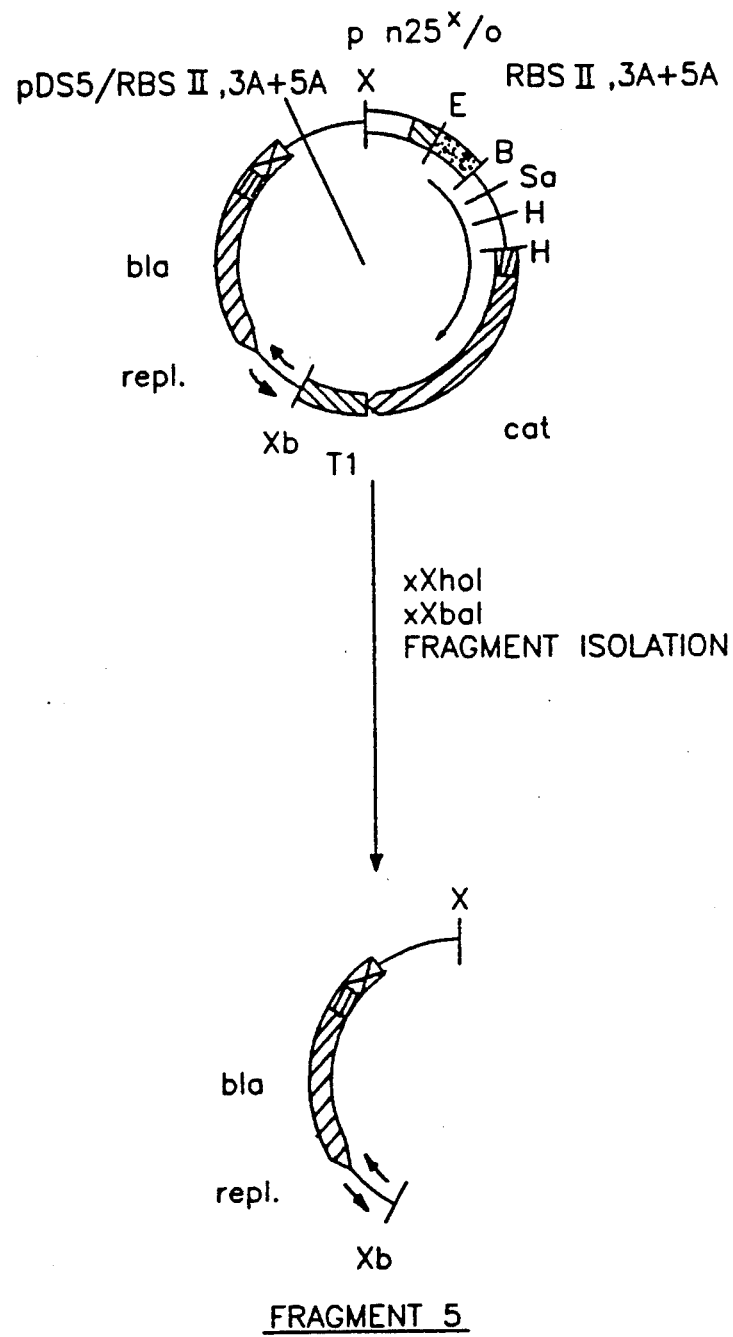
Figure 20:
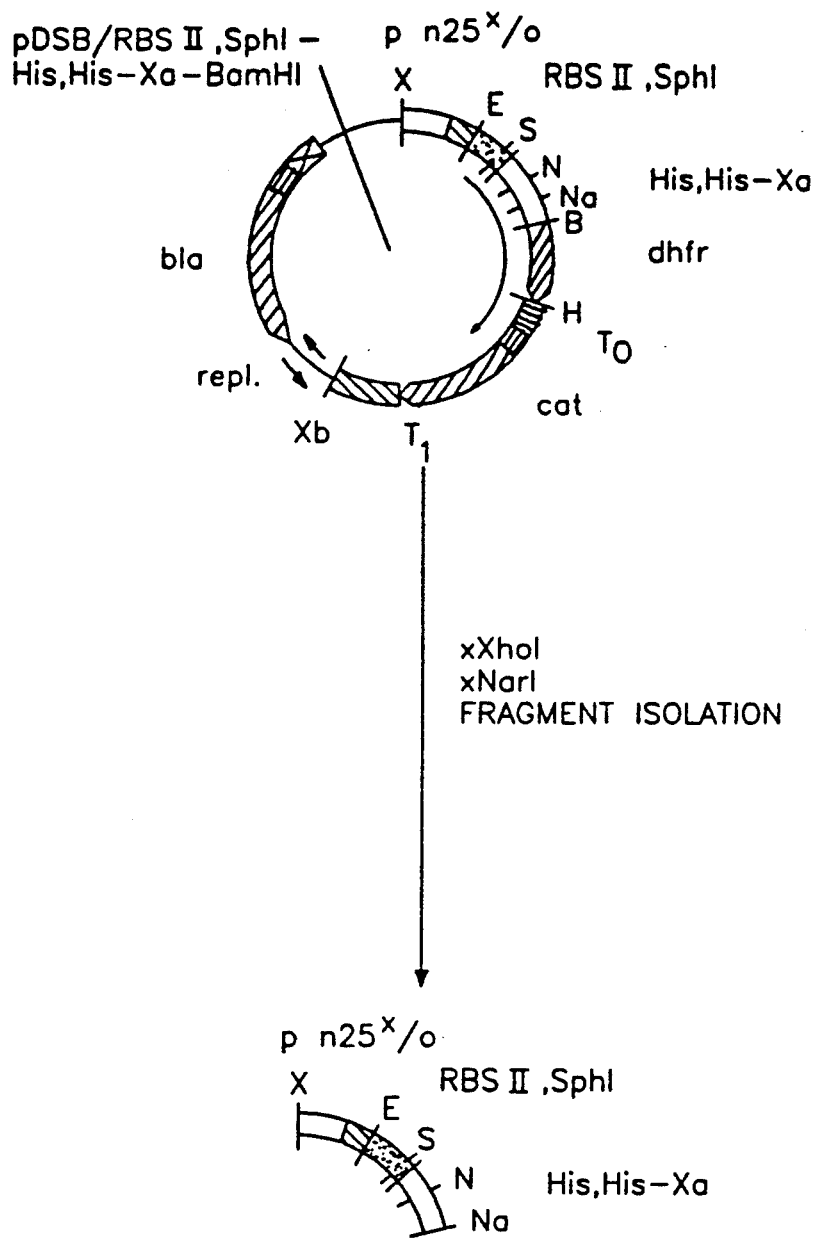

For the construction of plasmid pHis,His-Xa-IFN-γ, the following DNA fragments were isolated and linked with one another (FIG. 21): 1) the IFN-γ gene of plasmid pGLS (fragment 4, FIG. 18) linked with adaptor 4 (FIGS. 11A–B): 2) the signal unit of the plasmid pDS8/RBSII,SphI-His,His-Xa-BamHI, which contains the promoter $P_{N25X/O}$, the ribosomal binding site RBSII, SphI and the region coding for the neighbouring histidines and for the recognition site of factor Xa (fragment 6, FIG. 20); and 3) the replication region with the β-lactamase gene from plasmid pDSS/RBSII,-3A+5A (fragment 5, FIG. 19).

B. Preparation of Fragment 4

2 pmol of plasmid pGLS were cleaved with the restriction enzyme NdeI. After heat inactivation of the enzyme, the sample was extracted with phenol, extracted with ether and the DNA was precipitated as described. The sediment was dissolved in 10 μl of ligase buffer. 50 pmol of phosphorylated adaptor 4 (FIGS. 11A–B) dissolved in ligase buffer were added to the NdeI-cleaved plasmid pGLS, and the sample was incubated (22° C. 3 hours) with 2 U of ligase. After heat inactivation of the ligase, the sample was extracted with phenol, extracted with ether and the DNA was precipitated as described. The sediment was dissolved and the DNA was cleaved with the restriction enzymes NarI and XbaI. After the addition of sample buffer, heating the mixture at 65° C. for 7 minutes and separation of the DNA in a 6% polyacrylamide gel the NarI/XbaI fragment, which contained the IFN-γ gene, was isolated as described above. This fragment was designated fragment 4 (FIG. 18).

Preparation of Fragment 5

2 pmol of plasmid pDS5/RBSII,3A+5A were cleaved with the restriction enzymes XhoI and XbaI. The mixture was worked-up as described above, and the DNA was separated in a 6% polyacrylamide gel. The fragment which contained the bla gene and the replication region was isolated from the gel as described. This fragment was designated fragment 5 (FIG. 19).

D. Preparation of Fragment 6

2 pmol of plasmid pDS8/RBSII,SphI-His,His-Xa-BamHI were cleaved with the restriction enzymes XhoI and NarI. After working-up the sample and gel electrophoresis, fragment 6, which contains the promoter $P_{N25X/O}$, the ribosomal binding site RESII,SphI and the region which codes for the neighbouring histidines and the recognition site for factor Xa (FIG. 20) was isolated.

E. Assembly of Plasmid pHis,His-Xa-IFN-γ

0.5 pmol each of fragments 4,(FIG. 18). 5 (FIG. 19) and 6 (FIG. 20) were incubated (220° C. 5 hours) in ligase buffer with 2 U of T4 DNA ligase. After heat inactivation of the enzyme, the batch was transformed as described above into E. coli strain M15 which contained the plasmid pDMI.1, and the transformation mixture was plated-out on LB agar plates which contained 100 μg/ml ampicillin and 25 μg/ml kanamycin.

After incubation at 370° C. overnight, about 100 transformants were obtained. Individual colonies were grown up in 100 ml of LB medium as previously described, and the plasmids were isolated according to the method of Birnboim and Doly (supra). All plasmids were cleaved with the restriction enzymes XhoI, BamHI and XbaI and the fragments were analyzed in 6% poly-acrylamide gels.

Figure 21:
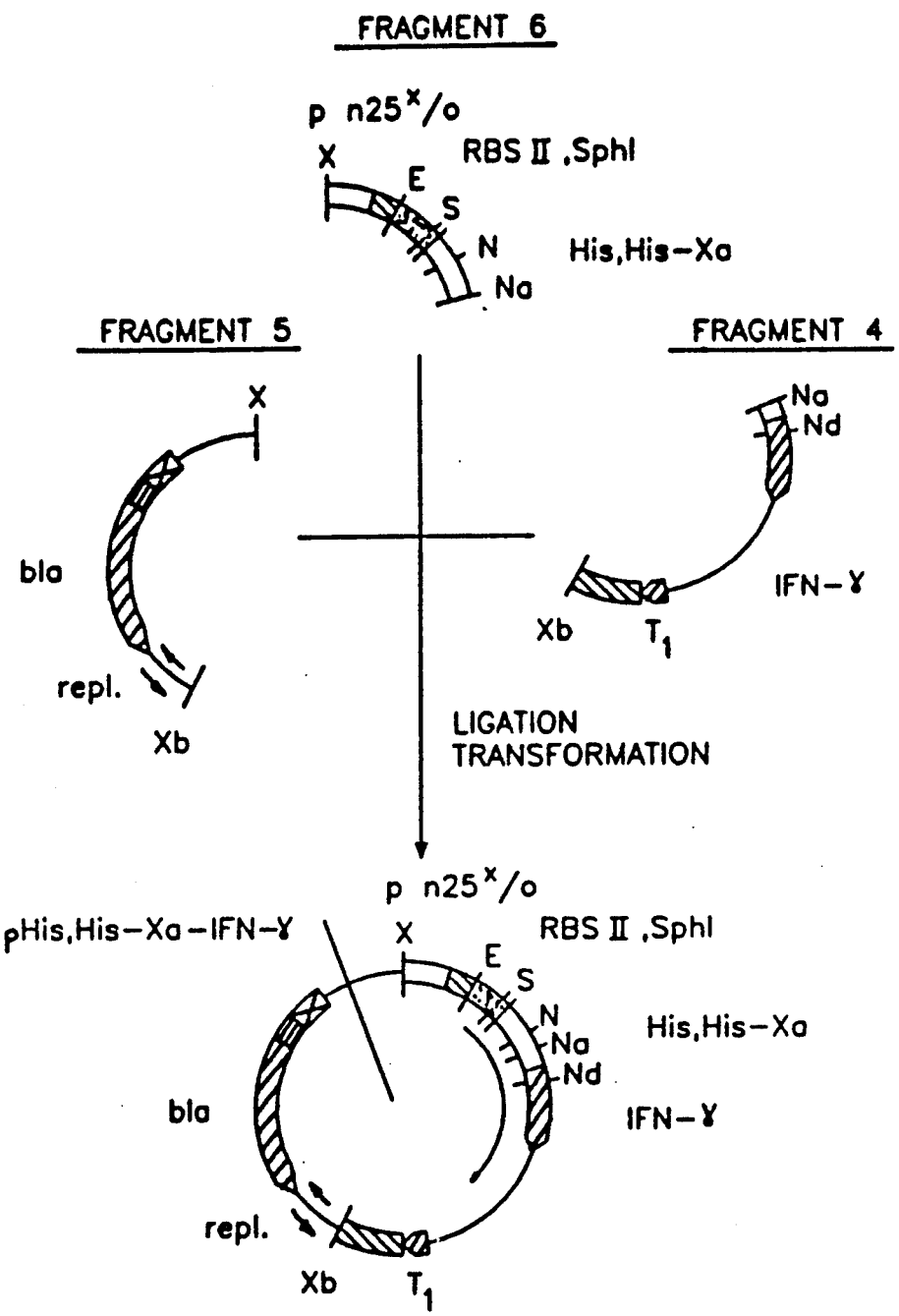

The restriction enzyme analysis indicated that the plasmids contained the 3 desired fragments. Sequence analyses carried out as described above (Example 3, E) showed that adaptor 4 was fused correctly to the IFN-γ gene. These plasmids were designated pHis,His-Xa-IFN-γ (FIG. 21). The IFN-γ fusion protein (for amino acid sequence, see FIG. 41) coded from these plasmids was designated His,His-Xa-IFN-γ.

Example 7

Construction of Plasmid pHis,His-Ek-IFN-γ(-8)

A. Principles

For the construction of the plasmid pHis,His-Ek-IFN-γ(-8), the following 3 DNA fragments were linked with one another (FIG. 24): 1) a fragment from plasmid pDS8/RBSII,SphI-His,His-Xa-BamHI containing the promoter $P_{N25X/O}$, the ribosomal binding site RBSII,SphI and the region coding for the adjacent histidines, which has been lengthened with the aid of adaptor 5 (FIGS. 11A–B) by a region coding for the recognition site of enterokinase (EK) (fragment 7, FIG. 22); 2) a fragment from the plasmid pIFN-γ(-8) which contains the gene for IFN-γ(-8) (fragment 8, FIG. 23): and 3) a fragment from the plasmid pDSS/RBSII,-3A+5A having the replication region and the β-lactamase gene (fragment 5, FIG. 19). The preparation of the last-named fragment has been described in Example 6.

B. Preparation of Fragment 7

4 pmol of plasmid pDS8/RBSII,SphI-His,His-Xa-BamHI were cleaved with the restriction enzyme NaeI. Subsequently, the enzyme was heat-inactivated, the sample was extracted with phenol, extracted with ether and the DNA was precipitated as described. The sediment was taken up in 50 μl of TE buffer. 1.5 pmol of the cleaved DNA were incubated in a volume of 200 μl with 30 pmol of the phosphorylated adaptor 5 (FIGS. 11A–B) and 7U of T4 DNA ligase for 14 hours in ligase buffer. After heat inactivation of the enzyme the DNA was cleaved with the restriction enzymes NdeI and XhoI.

Subsequently, the enzymes were heat-inactivated, the sample was extracted with phenol, extracted with ether and the DNA was precipitated as described above. The sediment was taken up in sample buffer, and the mixture was incubated for 7 minutes at 65° C. Thereafter, the DNA was separated in a 6% polyacrylamide gel. 0.2 pmol of the XhoI/NdeI fragment containing the promoter $P_{N25X/O}$, the ribosomal binding site RBSII,SphI and the region coding for the neighbouring histidines and for the recognition site of enterokinase, was isolated from the gel as previously described. This DNA fragment was designated fragment 7 (FIG. 22).

C. Preparation of Fragment 8

Figure 23:
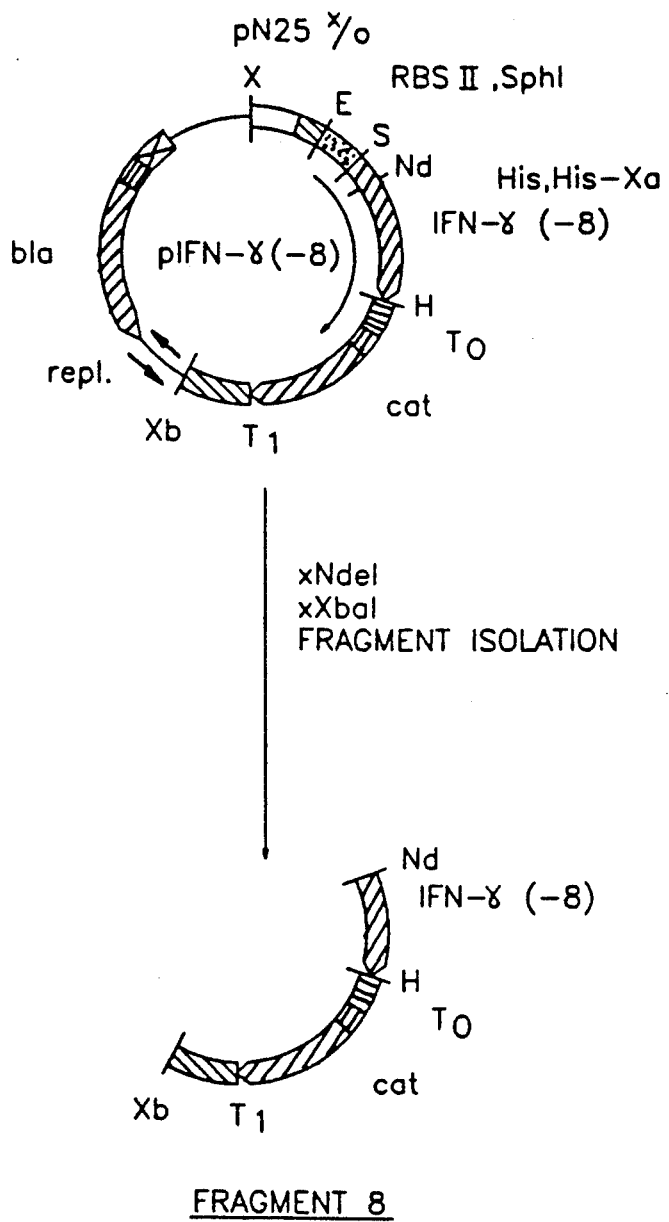

0.5 pmol of the plasmid pIFN-γ(-8) was cleaved with the restriction enzymes NdeI and XbaI. Subsequently, the enzyme was heat-inactivated, the sample was extracted with phenol, extracted with ether and the DNA was precipitated as described. The sediment was taken up in sample buffer and the mixture was incubated for 7 minutes at 65° C. The DNA was then separated in a 6% polyacrylamide gel. 0.05 pmol of the NdeI/XbaI fragment containing the IFN-γ(-8) gene, the terminator $t_o$, the cat gene and the terminator T1 was isolated from the gel as described. This DNA fragment was designated fragment 8 (FIG. 23).

D. Assembly of Plasmid pHis,His-Ek-IFN-γ(-8)

0.006 pmol of fragment 5 (FIG. 19). 0.02 pmol of fragment 7 (FIG. 22) and 0.005 pmol of fragment 8 (FIG. 23) were incubated in ligase buffer in a volume of 30 μl with 0.5 U of T4 DNA ligase for 3 hours at 150° C. After heat inactivation of the enzyme, the batch was transformed as described above into E. coli strain M15 which contained the plasmid pDMI,1, and the transformation mixture was plated-out on LB plates which contained 100 μg/ml ampicillin, 25 μg/ml kanamycin and 5 μg/ml chloramphenicol.

After incubation of the plates for 24 hours at 37° C., 2 of the transformants obtained were grown up in 10 ml of LB medium containing 100 μg/ml ampicillin, 25 μg/ml kanamycin and 5 μg/ml chloramphenicol, and the plasmids were isolated according to the method of Birnboim and Doly (supra).

Figure 24:
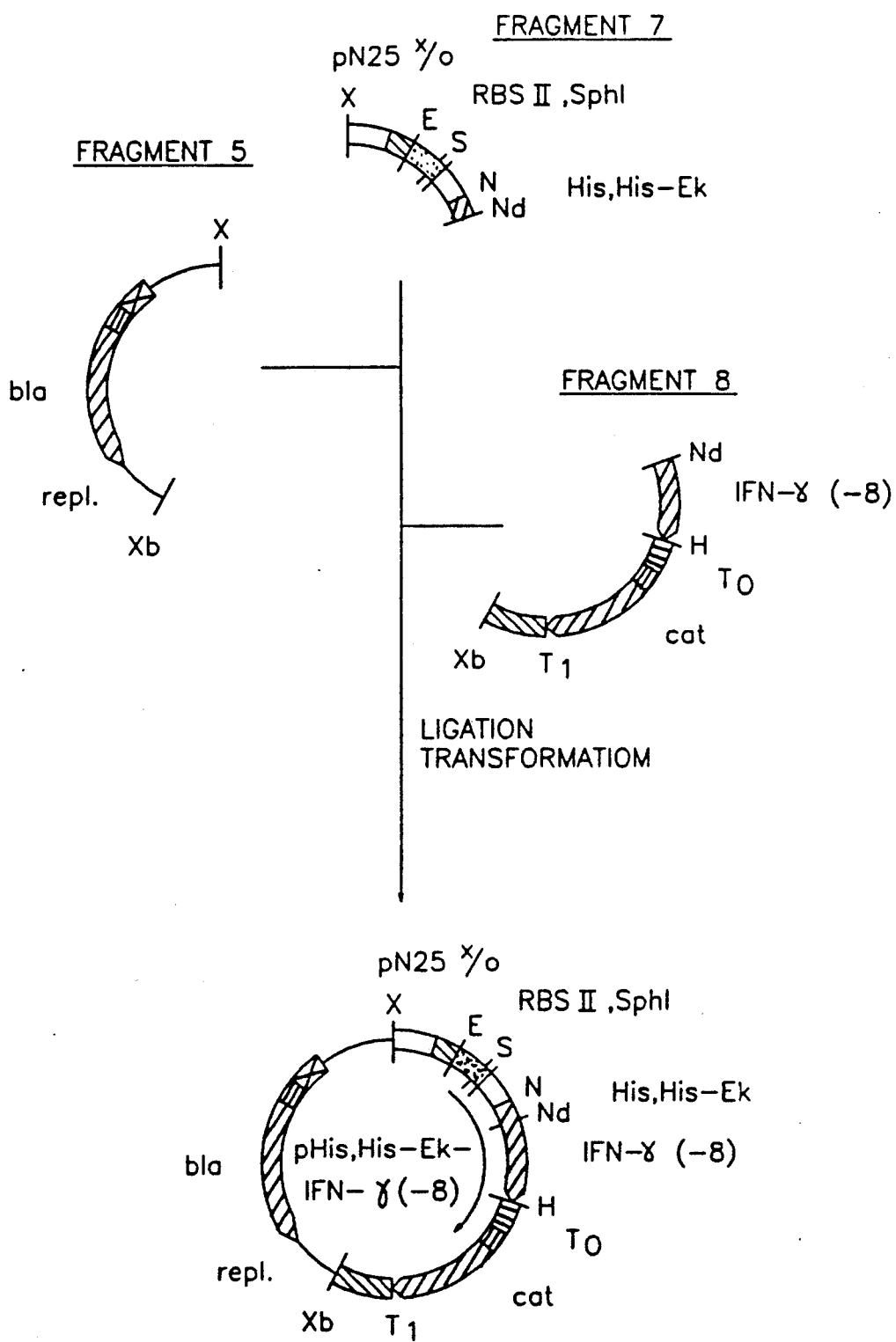

The plasmids were analyzed for size in 0.7% agarose gels and for composition with the aid of the restriction enzymes HindIII, HinfI, NdeI, SphI, XbaI and XhoI in 6% polyacrylamide gels. Both plasmids contained the 3 desired DNA fragments in the correct orientation to one another. The sequence analyses, which were carried out as previously described (Example 3. E), indicated that the ribosomal binding site RBSII,SphI with the subsequent elements had been linked correctly with the IFN-γ(-8) gene. These plasmids were designated pHis,His-Ek-IFN-γ(-8) (FIG. 24). The IFN-γ fusion protein (amino acid sequence, FIG. 42) coded from these plasmids was designated His,His-Ek-TFN-γ(-8).

Example 8

Construction of Plasmid pHis,His-Xa-IFN-γ(-8)(Asn)

A. Principles

For the construction of plasmid pHis,His-Xa-IFN-γ(-8)(Asn), the following 3 DNA fragments were linked with one another (FIG. 26): 1) a fragment from the plasmid pIFN-γ(-8) which contained the IFN-γ(-8) gene (fragment 8. FIG. 23, the preparation of which has been described in Example 7); 2) a fragment from the plasmid pDS8/RBSII,SphI-His,His-Xa-BamHI containing the promoter $p_{N25X/O}$, the ribosomal binding site RBSII,SphI and the region coding for the neighbouring histidines and for the recognition site of factor Xa, which has been lengthened with the aid of adaptor 6 (FIGS. 11A–B) so that, by linkage with the fragment described under 1), the IFN-γ(-8) derivative IFN-γ(-8)(Asn) is coded (fragment 9. FIG. 25); and 3) a fragment from the plasmid pDS5/RBSII, 3A+5A with the replication region and the gene for β-lactamase (fragment 5, FIG. 19, the preparation of which has been described in Example 6).

B. Preparation of Fragment 9

2 pmol of plasmid pDS8/RBSII,SphI-His,His-Xa-BamHI were cleaved with the restriction enzyme NarI. Subsequently, the enzyme was heat-inactivated, the sample was extracted with phenol, extracted with ether and the DNA was precipitated as described. The sediment was taken up in 50 μl of TE buffer. 1 pmol of the cleaved DNA was incubated in a volume of 150 μl with 30 pmol of phosphorylated adaptor 6 (FIGS. 11A–B) and 5U of T4 DNA ligase for 14 hours at 20° C. in ligase buffer. After heat inactivation of the enzyme the DNA was cleaved with the restriction enzymes NdeI and XhoI.

Subsequently, the enzymes were heat-inactivated, the sample was extracted with phenol, extracted with ether and the DNA was precipitated as described. The sediment was is taken up in sample buffer and the batch was incubated for 7 minutes at 65° C. The resulting DNA mixture was then separated in a 6% poly-acrylamide gel. 0.25 pmol of the. XhoI/NdeI fragment with the promoter $P_{N25X/O}$, the ribosomal binding site RBSII,SphI and the region which codes for the adjacent histidines, for the recognition site of factor Xa and for the amino acid Asn was isolated from the gel as described. This DNA fragment was designated fragment 9 (FIG. 25).

C. Assembly of Plasmid pHis,His-Xa-IFN-γ(-8)(Asn)

0.006 pmol of fragment 5 (FIG. 19). 0.005 pmol of fragment 8 (FIG. 23) and 0.02 pmol of fragment 9 (FIG. 25) were incubated in 30 μl of ligase buffer and 0.5 U of T4 DNA ligase for 3 hours at 15° C. After heat inactivation of the enzyme, the batch was transformed as described above into E. coli strain MIS which contained the plasmid pDMI,1, and the transformation mixture was plated-out on LB plates containing 100 μg/ml ampicillin and 25 μg/ml kanamycin. After incubation of the plates at 37° C. overnight 2 colonies were grown up as described in 10 ml of LB medium containing 100 μg/ml ampicillin and 25 μg/ml kanamycin, and the plasmids were isolated according to the method of Birnboim and Doly (supra).

The plasmids were analyzed with respect to their size in 0.7% agarose gels and with respect to their composition with the aid of the restriction enzymes HindIII, HinfI, NdeI, SphI, XbaI and XhoI in 6% polyacrylamide gels. One of the two plasmids contained the desired 3 DNA fragments in the correct orientation to one another.

Figure 26:
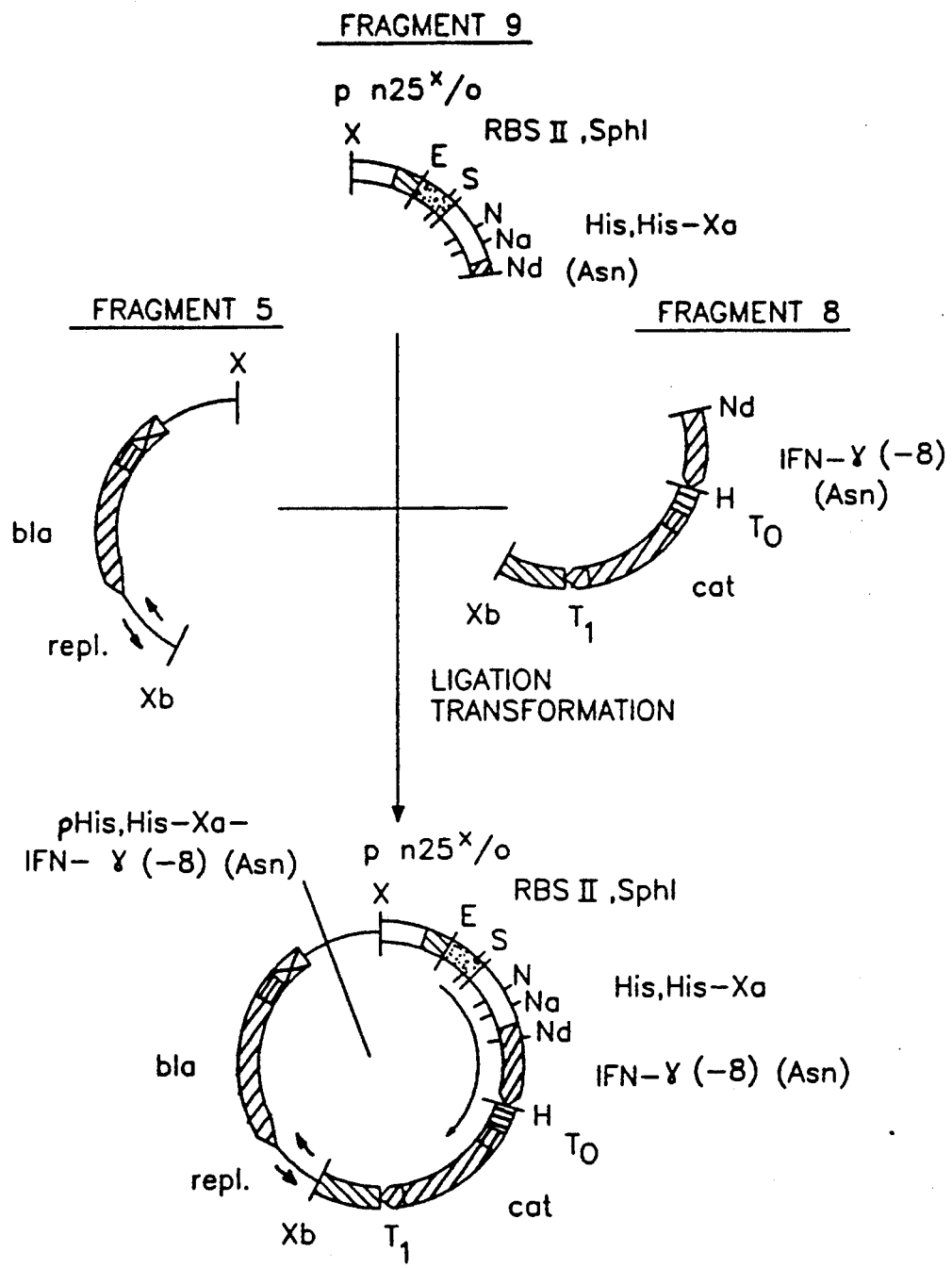

Sequence analysis of this plasmid carried out as described above (Example 3. E) indicated that the ribosomal binding site RBSII,SphI with the following elements had been correctly linked with the region which codes for IFN-γ(-8)(Asn). This plasmid was designated pHis,His-Xa-IFN-γ(-8)(Asn) (FIG. 26). The IFN-γ fusion protein (for amino acid sequence, see FIG. 43)

coded from this plasmid was designated His,His-Xa-IFN-γ(-8)(Asn).

Example 9

Construction of Plasmid p6xHis-DHFR

A. Principles

Figure 27:
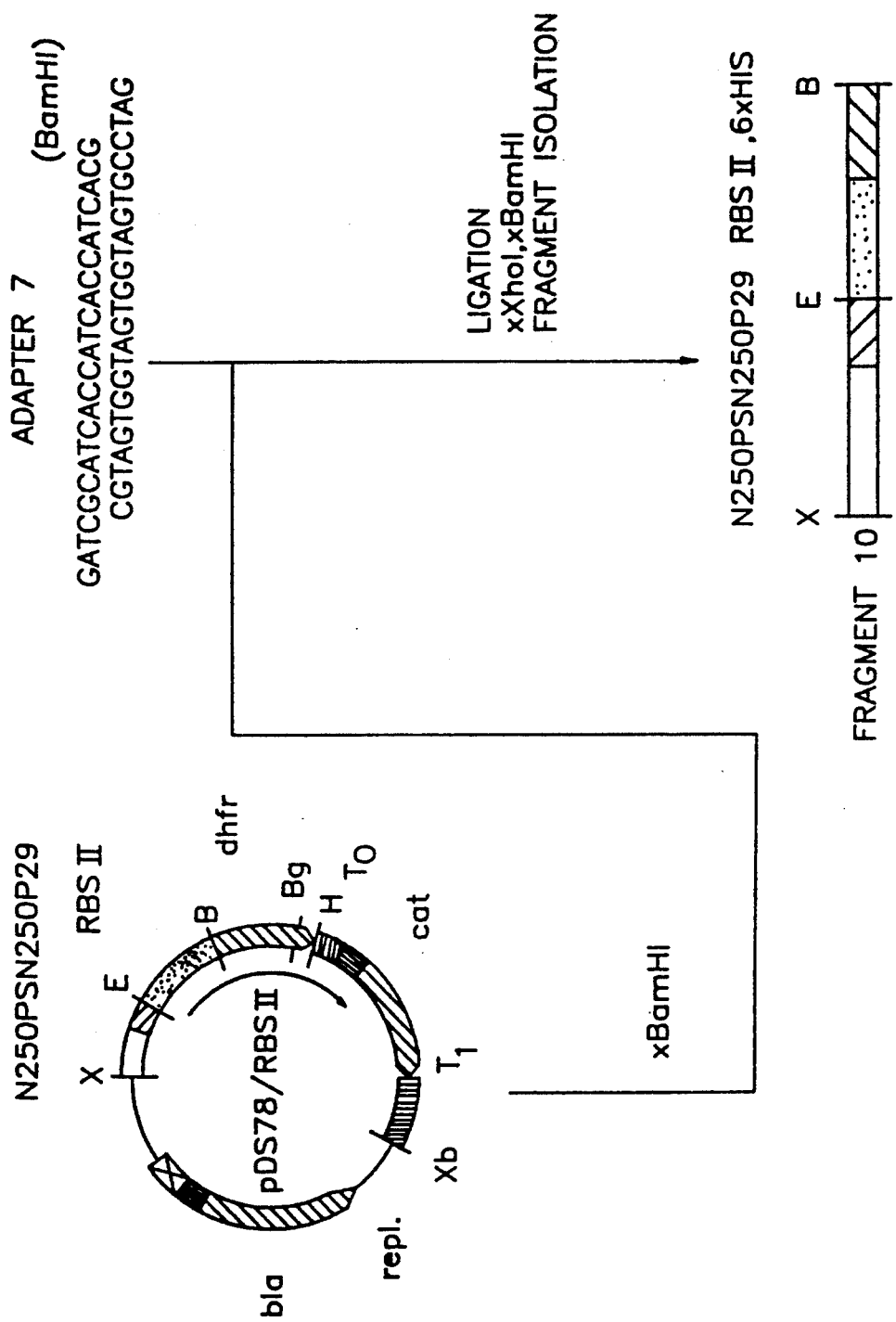
Figure 28:
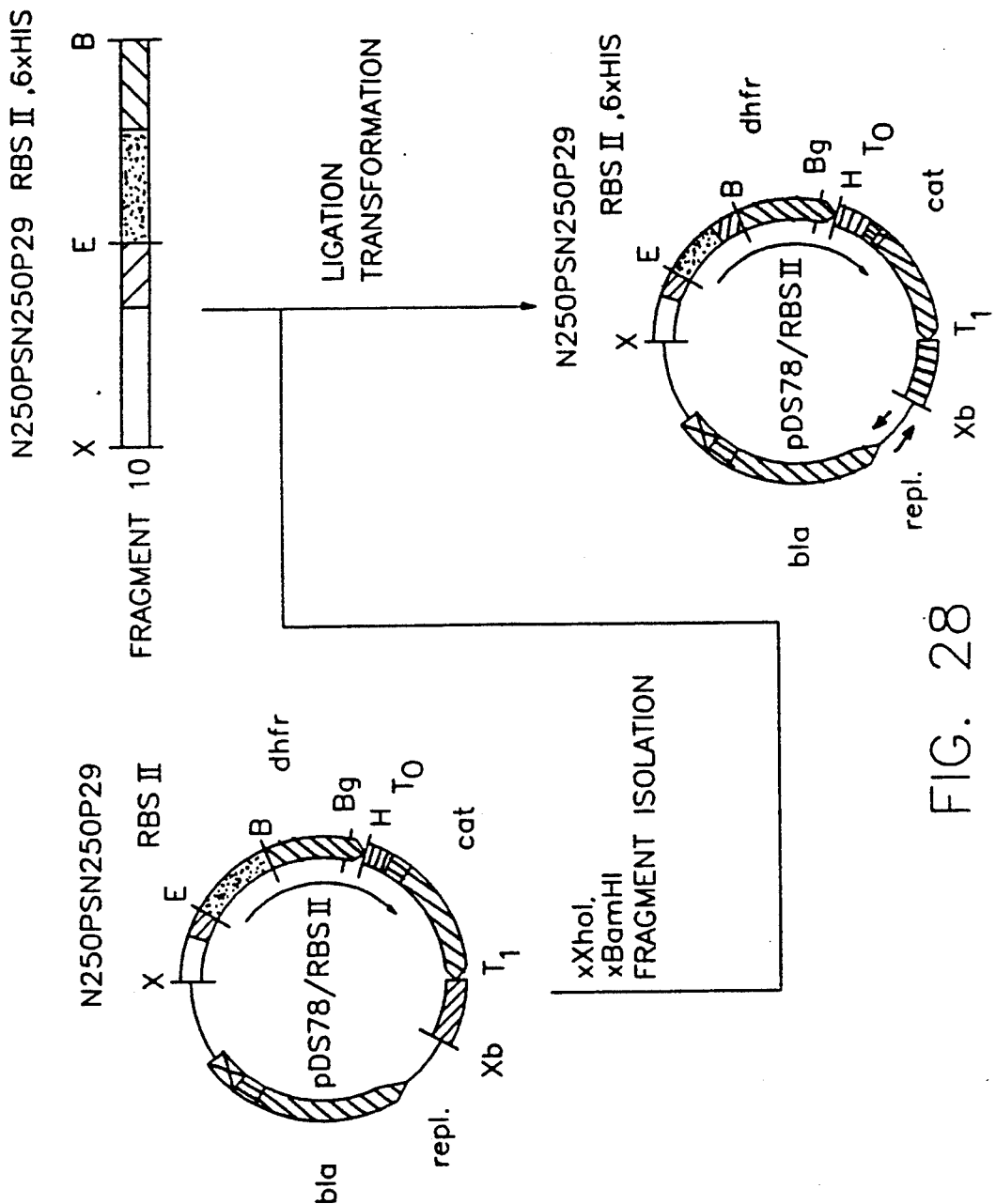

For the construction of plasmid p6xHis-DHFR, the following DNA fragments were isolated and linked with each other (FIG. 28): 1) the signal unit of the plasmid pDS78/RBSII having the promoter N25OPSN25OP29 and the ribosomal binding site RBSII, which has been linked with the adaptor 7 (FIGS. 11A-B), (fragment 10, FIG. 27) and 2) the larger of the two XhoI/BamHI fragments of the plasmid pDS78/RBSII (FIG. 28).

B. Preparation of Fragment 10

2 pmol of plasmid pDS78/RBSII were cleaved with the restriction enzyme BamHI. After heat inactivation of the enzyme, the sample was extracted with phenol, extracted with ether and the DNA was precipitated as described. The sediment was dissolved in 10 µl of ligase buffer. 50 pmol of the phosphorylated adaptor 7 (FIG. 27) dissolved in ligase buffer were added to the cleaved plasmid, and the sample was incubated with 2 U of ligase (22° C., hours).

After heat inactivation of the ligase, the sample was extracted with phenol, extracted with ether and the DNA was precipitated as described. The sediment was dissolved and the DNA was cleaved with the restriction enzymes XhoI and BamHI. After adding sample buffer, heating the mixture at 65° C. for 7 minutes and separating the DNA in a 6% polyacrylamide gel the XhoI/BamHI fragment having the promoter N25OPSN-25OP29, the ribosomal binding site RBSII and the region coding for 6 histidines was isolated as described. This fragment was designated fragment 10 (FIG. 27).

C. Preparation of the BamHI/XhoI Fragment of Plasmid pD78/RBSII 2 pmol of plasmid pDS78/RBSII were cleaved with the restriction enzymes XhoI and BamHI. After working-up the sample and gel electrophoresis, the fragment which contains the replication region (FIG. 28) was isolated.

D. Assembly of Plasmid p6xHis-DHFR

In each case 0.1 pmol of the specified fragments were incubated in ligase buffer with 2 U of T4 DNA ligase (22° C., 3 hours). After heat inactivation of the enzyme the mixture was transformed as described above into E. coli strain M15 which contained the plasmid pDMI,1. The transformation mixture was plated-out on LB agar plates which contained 100 µg/ml ampicillin and 25 µg/ml kanamycin, and the plates were incubated at 370° C. overnight.

Individual colonies were grown up in 10 ml of LB medium as described above, and the plasmids were isolated according to the method of Birnboim and Doly (supra). A restriction analysis with the enzymes XhoI and BamHI indicated that the plasmids contained the 2 desired fragments. Sequence analysis carried out as described above (Example 3. E) confirmed that adaptor 7 had been linked correctly with the ribosomal binding site. These plasmids, which code for the DHFR fusion protein (His)$_6$-mDHFR, were designated p6xHis-DHFR (FIG. 28).

EXAMPLE 10

Construction of Plasmid p4xHis-DHFR

Figure 29:
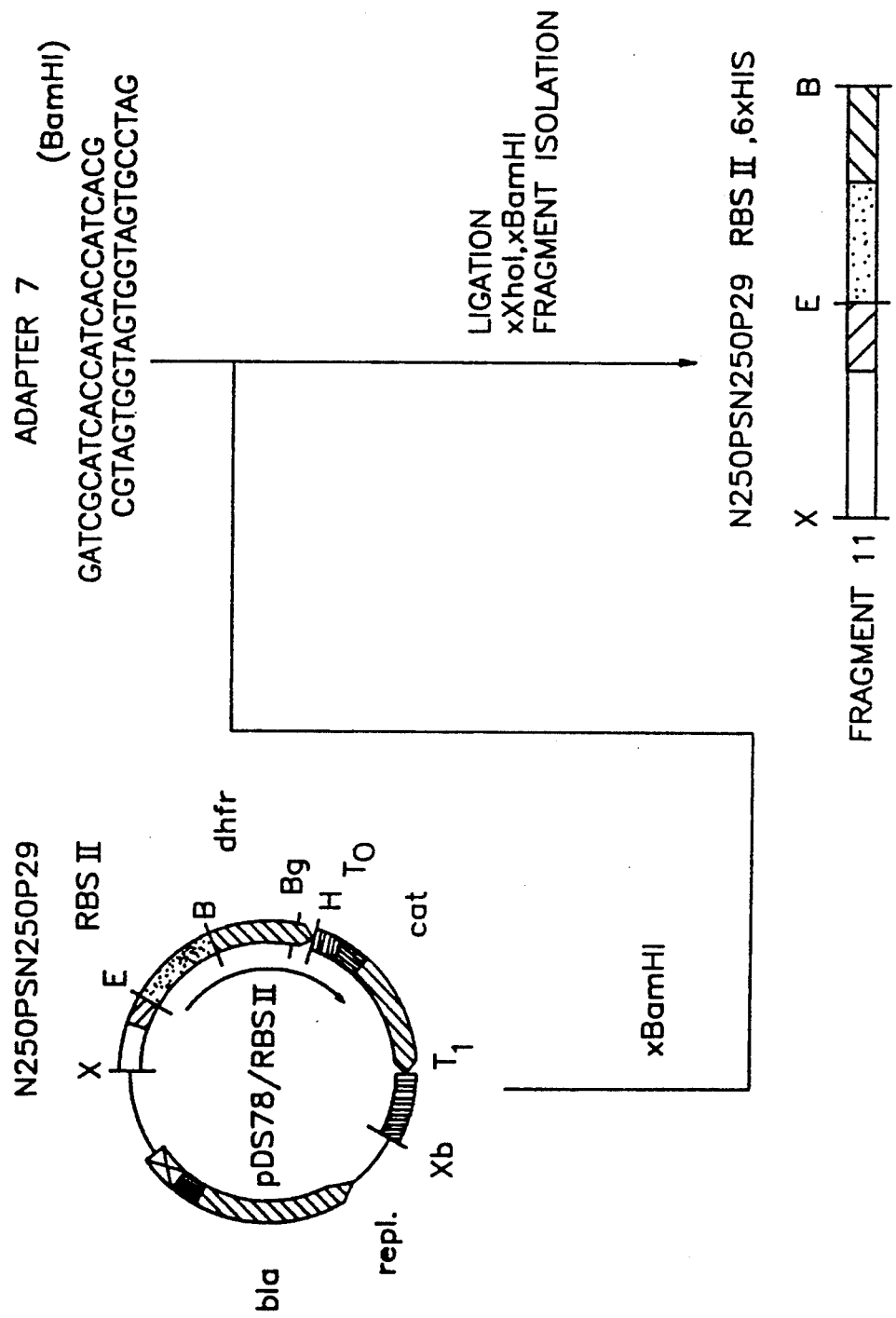
Figure 30:
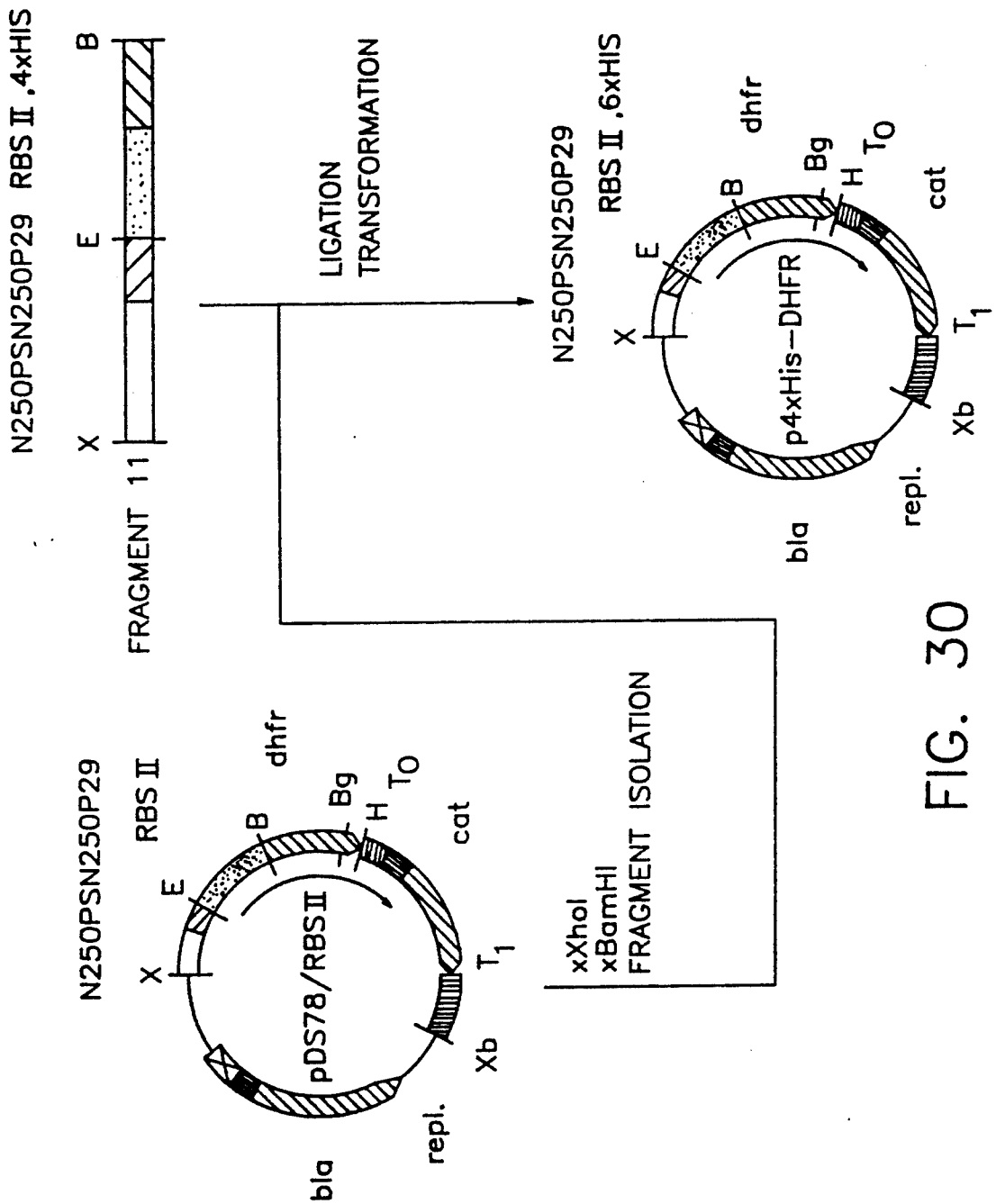

The construction of the plasmid p4xHis-DHFR was carried out analogously to the construction of plasmid p6xHis-DHFR (Example 9), with the following DNA fragments being isolated and linked with each other (FIG. 30): 1) the signal unit of plasmid pDS78/RBSII having the promoter N25OPSN25OP29 and the ribosomal binding site RBSII, which has been linked with the adaptor 8 (FIGS. 11A-B), (fragment 11, FIG. 29) and 2) the larger of the two XhoI/BamHI fragments of plasmid pDS78/RBSII (FIG. 30). The resulting plasmid p4xHis-DHFR codes for the DHFR fusion protein (His)$_4$-mDHFR.

Example 11

Construction of Plasmid pRBSII-6xHis

A. Principles

Figure 31:
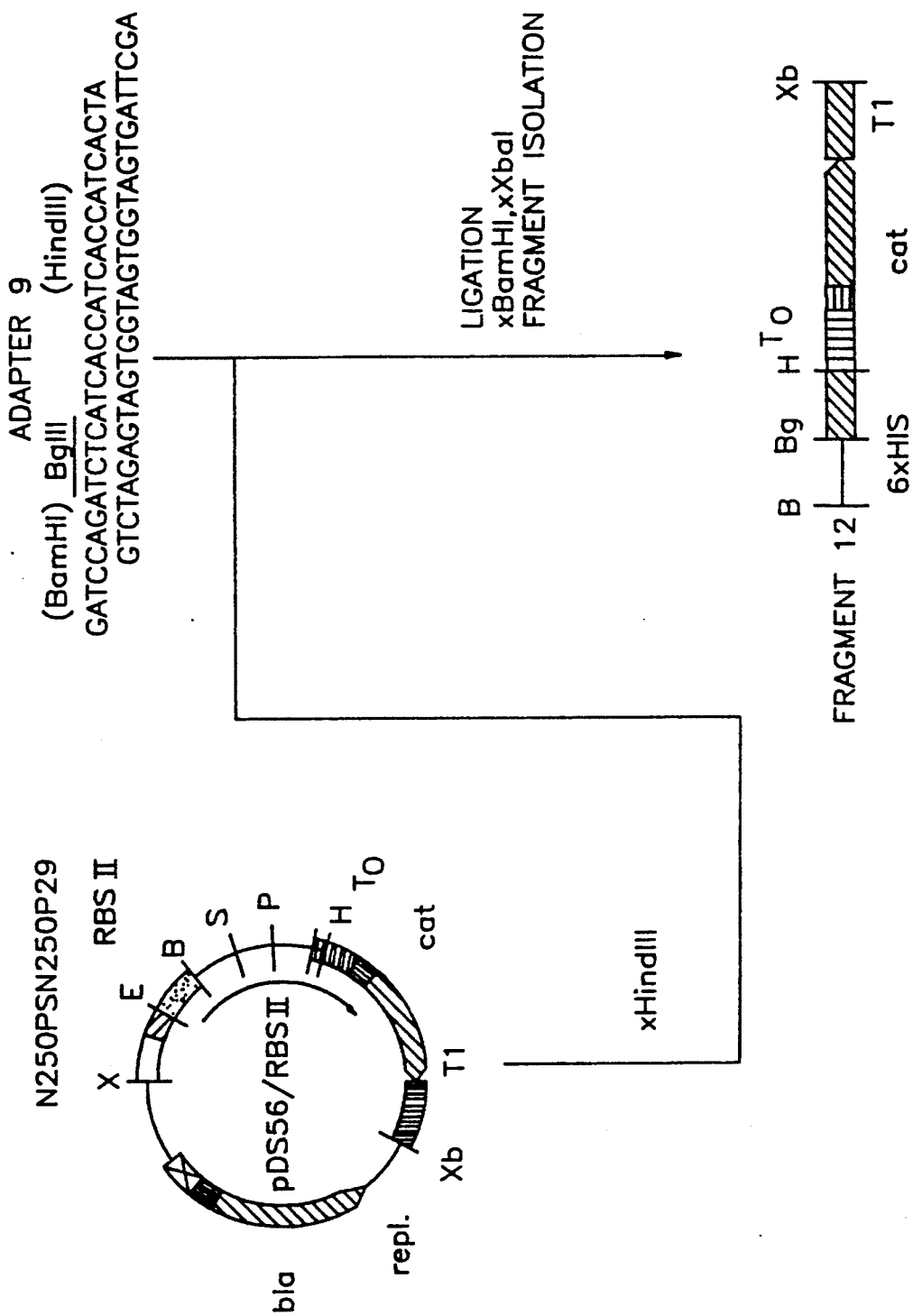
Figure 32:
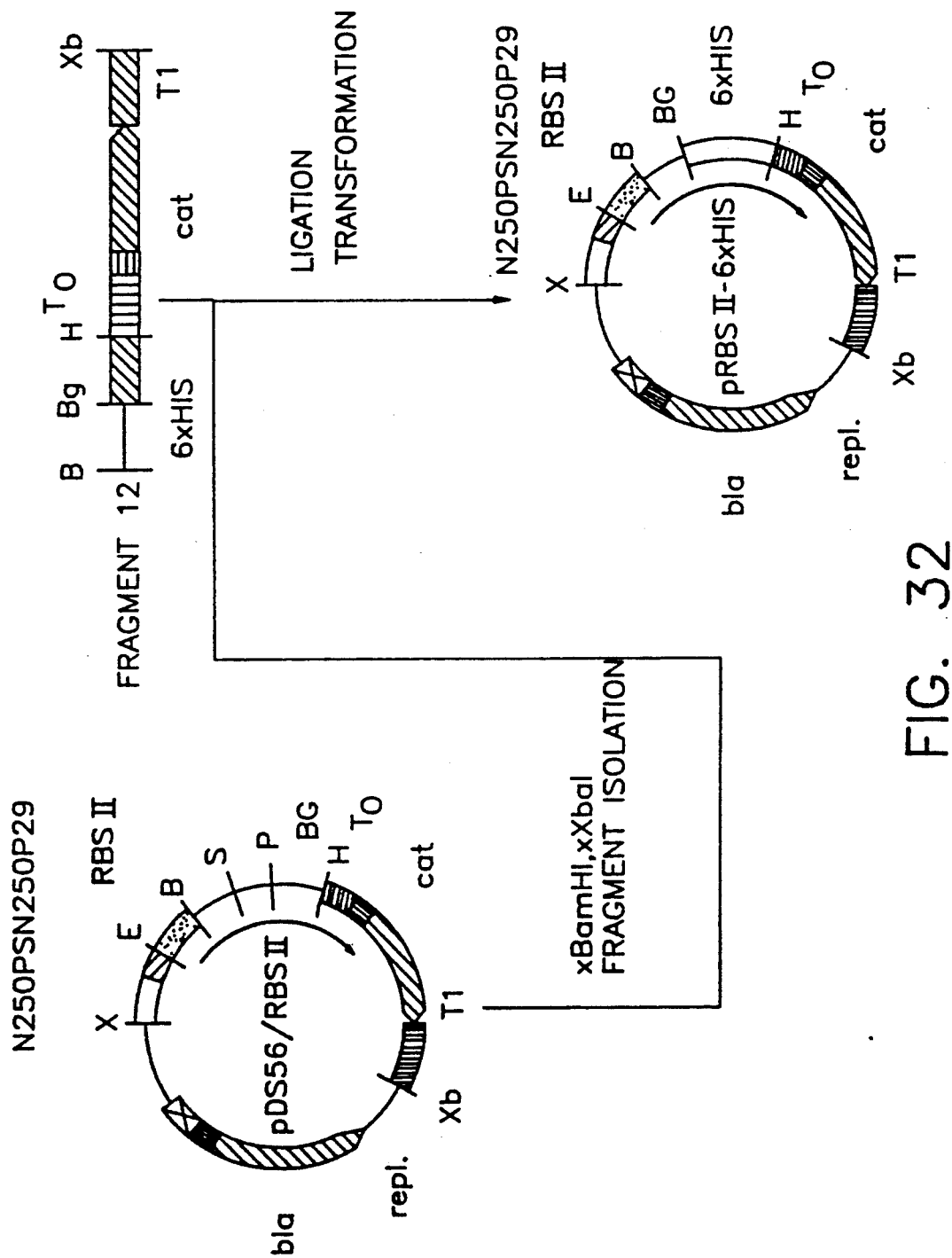

For the construction of plasmid pRBSII-6xHis, the following DNA fragments were isolated and linked with each other (FIG. 32): 1) the region from plasmid pDS56/ RBSII having the terminator $t_o$, the cat gene and the terminator T1, which has been lengthened by the adaptor 9 (which codes for 6 histidines), (fragment 12, FIG. 31) and 2) the XbaI/BamHI fragment from plasmid pDS56/RBSII having the replication region, the bla gene, the promoter N25OPSN25OP29 and the ribosomal binding site RBSII (FIG. 32).

B. Preparation of Fragment 12

2 pmol of plasmid pDS56/RBSII were cleaved with the restriction enzyme HindIII. After working-up the sample, 50 pmol of phosphorylated adaptor 9 were added to the cleaved plasmid, and the sample was incubated with T4 DNA ligase as previously described. After working-up the ligation batch, the DNA was cleaved with the restriction enzymes BamHI and XbaI, and the BamHI/XbaI fragment having the region coding for 6 histidines, the terminator $t_o$, the cat gene and the terminator T1 was isolated as described. This fragment was designated fragment 12 (FIG. 31).

C. Preparation of the XbaI/BamHI Fragment of Plasmid pDS56/RBSII 2 pmol of plasmid pDS56/RBSII were cleaved with the restriction enzymes XbaI and BamHI, and the fragment having the replication region, the bla gene, the promoter N25OPSN25OP29 and the ribosomal binding site RBSII was isolated as described (FIG. 32).

D. Assembly of Plasmid pRBSII-6xHis

In each case 0.1 pmol of the isolated fragments were, as described (Example 9,D), ligated and subsequently transformed into the E. coli strain M15 (pDMI,1). After plating and incubation (Example 9, D), individual colonies were grown up in 10 ml of medium as described and the plasmids were isolated according to the method of Birnboim and Doly (supra). A restriction analysis with the enzymes BamHI and XbaI indicated that the plasmids contained the 2 desired fragments. The sequence analysis (Example 3, E) confirmed that adaptor 9 had been introduced correctly, into the plasmid DNA. These plasmids were designated pRBSII-6xHis.

Example 12

Construction of Plasmid pRBSII-4xHis

Figure 33:
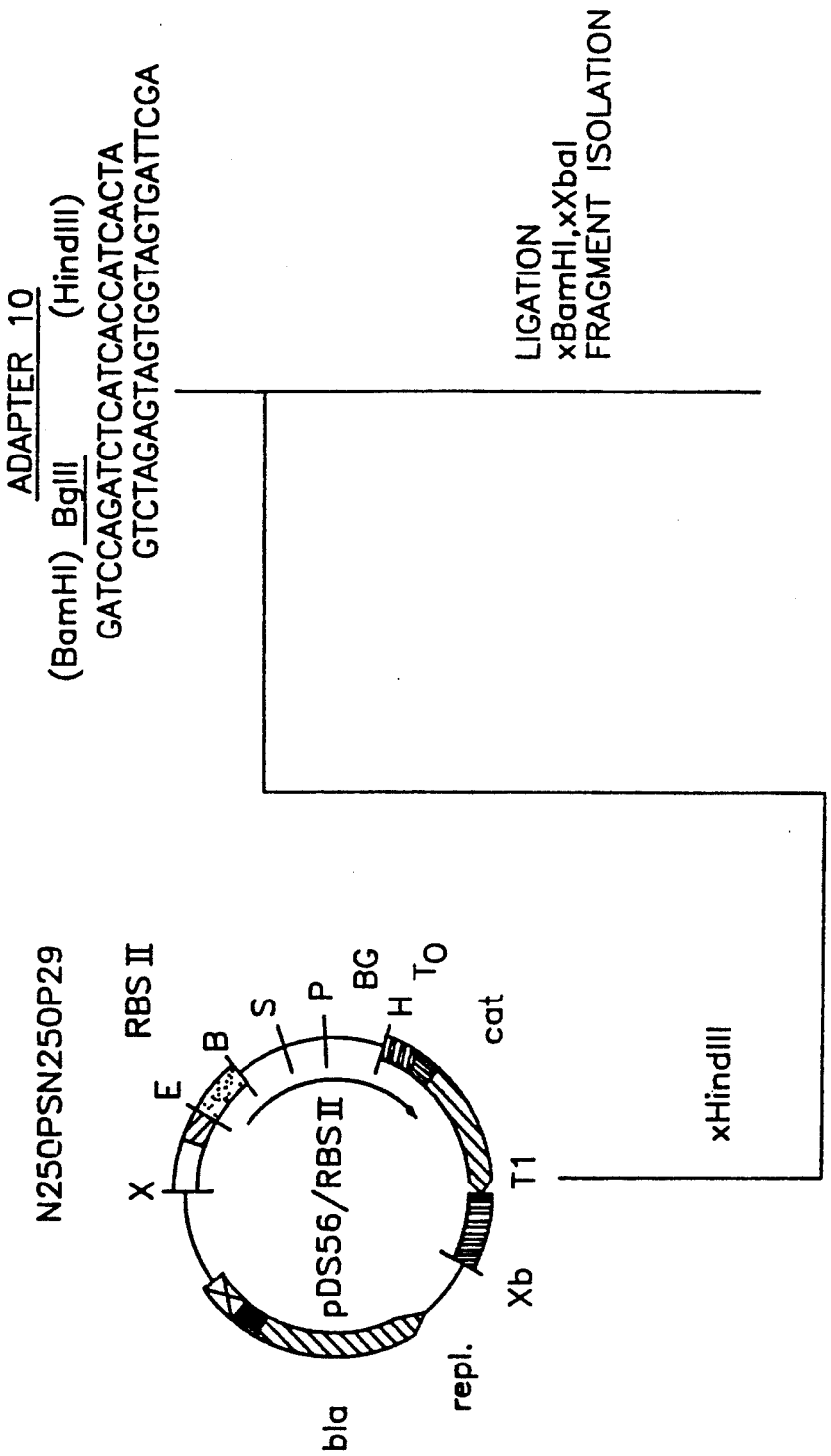
Figure 34:
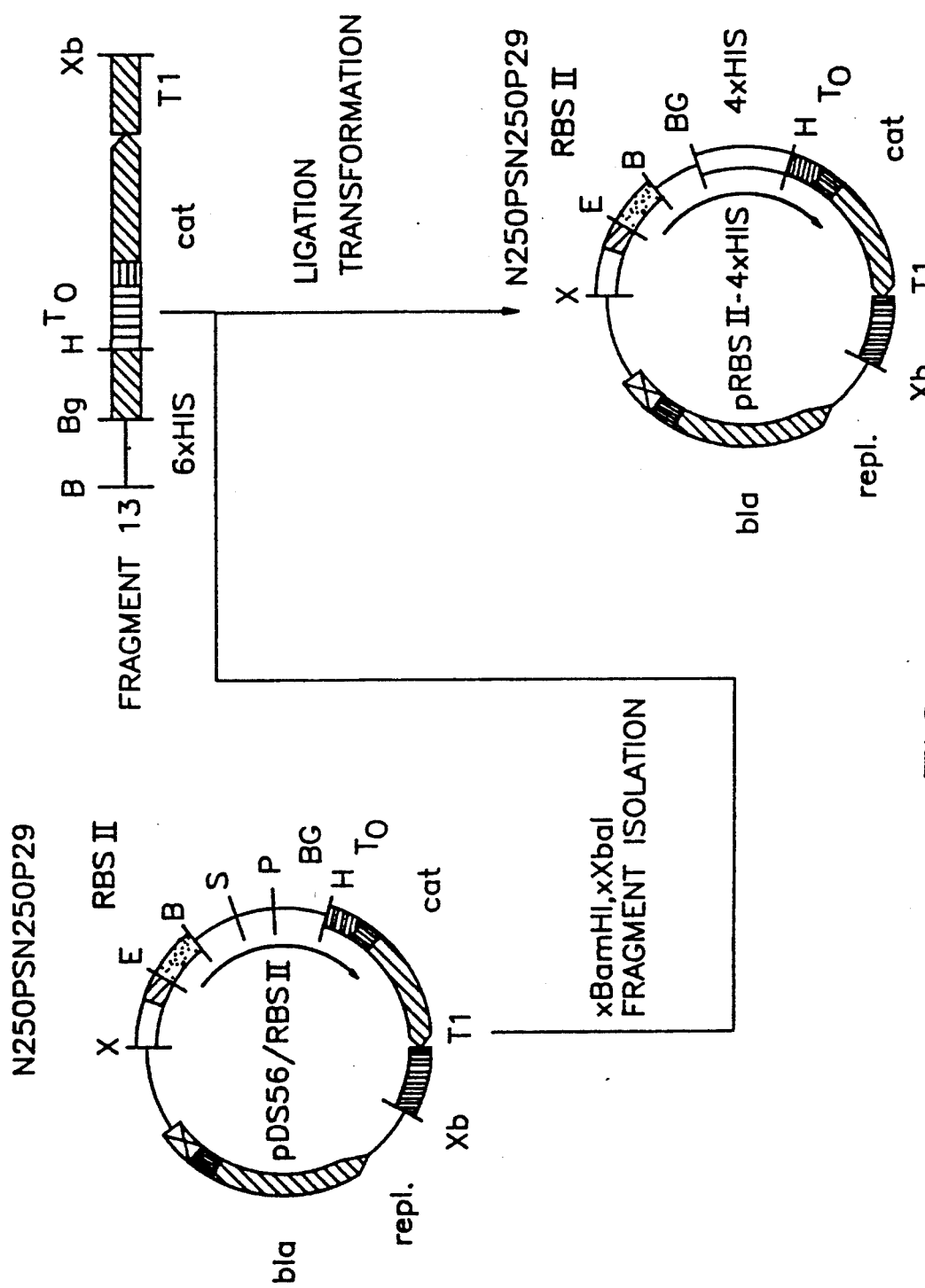

The construction of plasmid pRBSII-4xHis was carried out analogously to the construction of plasmid pRBSII-6xHis (Example 11), with the following DNA fragments being isolated and linked with each other (FIG. 34): 1) the region from the plasmid pDS56/RBSII having the terminator $t_o$, the cat gene and the terminator T1, which has been lengthened by adaptor 10 (which codes for 4 histidines), (fragment 13, FIG. 33) and 2) the XbaI/BamI fragment from plasmid pDS56/RBSII having the replication region, the bla gene, the promoter N25OPSN25OP29 and the ribosomal binding site RBSII (FIG. 34).

Example 13

Construction of Plasmid pRBSII-2xHis

Figure 35:
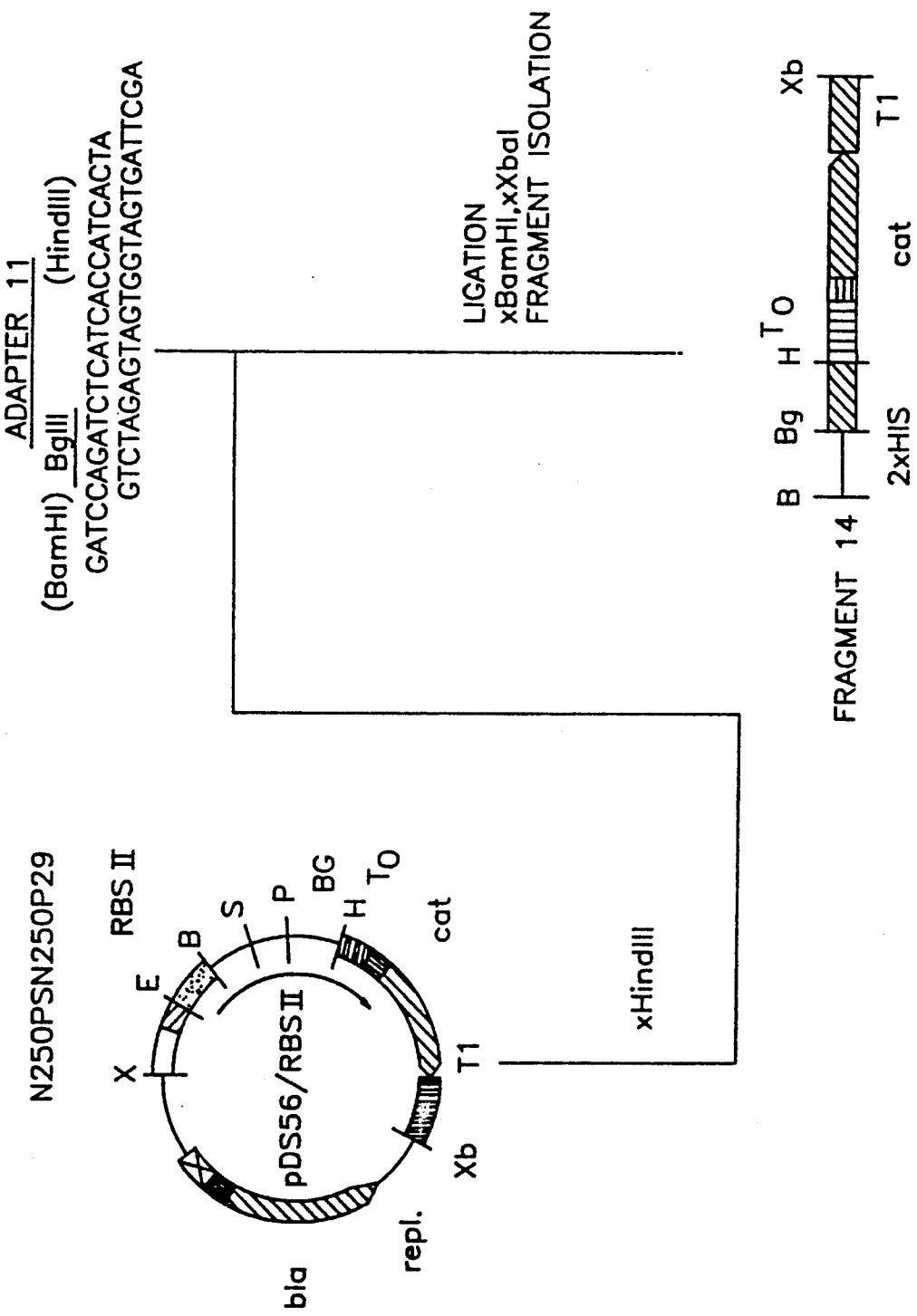
Figure 36:
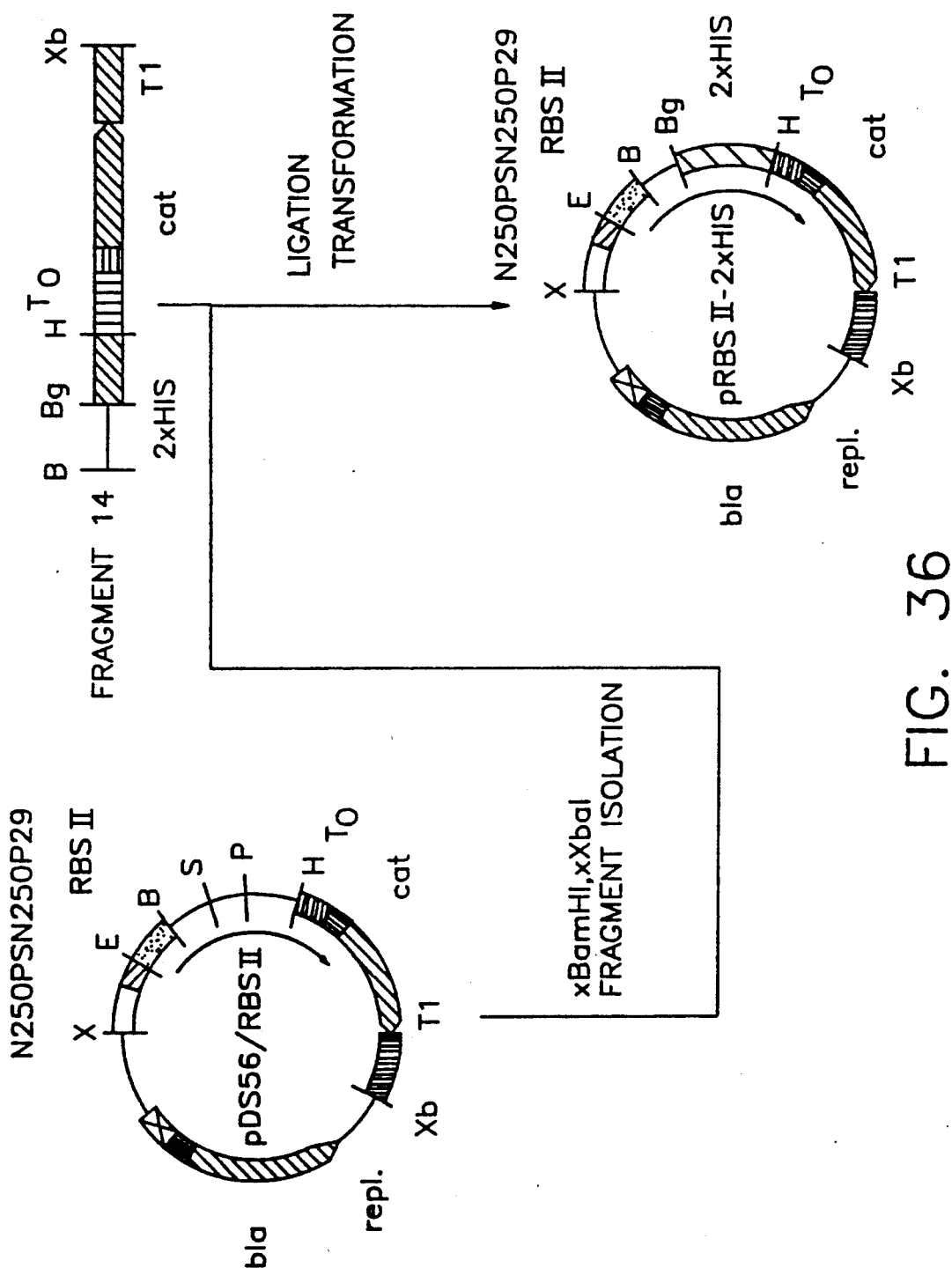

The construction of plasmid pRBSII-2xHis was carried out analogously to the construction of plasmid pRBSII-6xHis (Example 11), with the following DNA fragments being isolated and linked with each other (FIG. 36): 1) the region from plasmid pDS56/RBSII having the terminator $t_o$, the cat gene and the terminator T1, which has been lengthened by the adaptor 11 (which codes for 2 histidines), (fragment 14, FIG. 35) and 2) the XbaI/BamHI fragment from the plasmid pDS56/RBSII having the replication region, the bla gene, the promoter N25OPSN25OP29 and the ribosomal binding site RBSII (FIG. 36).

Example 14

Construction of Plasmid pDHFR-6xHis

A. Principles

Figure 37:
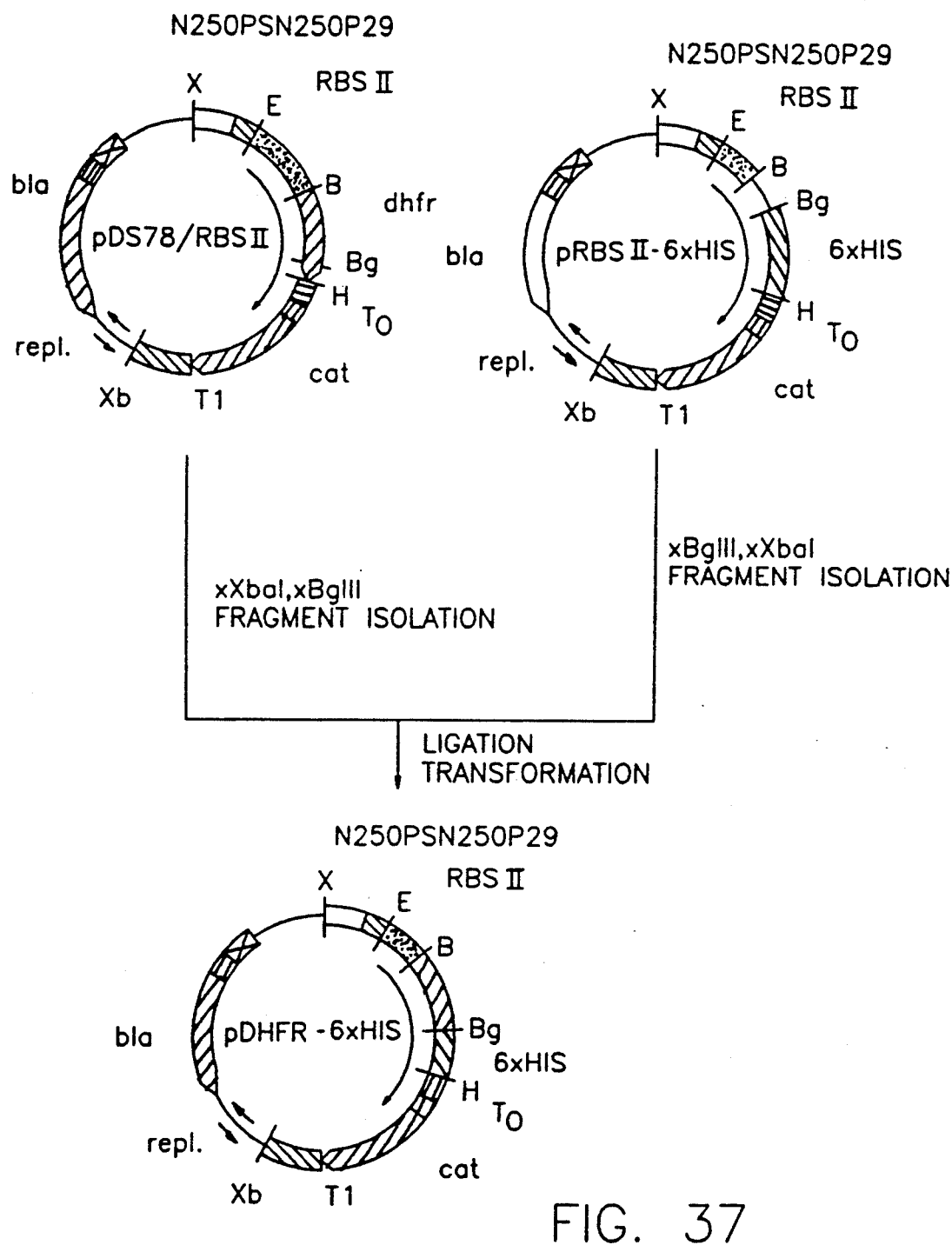

For the construction of plasmids pDHFR-6xHis, the following DNA fragments were isolated and linked with each other (FIG. 37): 1) the XbaI/BglII fragment from plasmid pDS78/RBSII having the replication region, the bla gene, the promoter N25OPSN25OP29, the ribosomal binding site RBSII and the dhfr gene and 2) the BglII/XbaI fragment from plasmid pRBSII-6xHis having the region coding for 6 histidines, the terminator $t_o$, the cat gene and the terminator T1. The resulting plasmid pDHFR-6xHis codes for the DHFR fusion protein Met-mDHFR-(His)$_6$.

B. Preparation of the XbaI/BqlII Fragment of Plasmid pDS78/RBSII 2 pmol of plasmid pDS78/RBSII were cleaved with the restriction enzymes XbaI and BglII. After working-up the sample the XbaI/BglII fragment having the replication region, the bla gene, the promoter N25OPSN25OP29, the ribosomal binding site RBSII and the dhfr gene was isolated as described.

C. Preparation of the BqlII/XbaI Fragment of Plasmid pRBSII-6xHis 2 pmol of plasmid pRBSII-6xHis were cleaved with the restriction enzymes BglII and XbaI. After working-up the sample the BglII/XbaI fragment having the region coding for 6 histidines, the terminator $t_o$, the cat gene and the terminator T1 was isolated as described.

D. Assembly of Plasmid pDHFR-6xHis

In each case 0.1 pmol of the isolated fragments were, as described (Example 9,D), ligated and transformed into *E. coli* strain M15 (pDMI,1). After plating and incubation (Example 9, D) individual colonies were grown up in 10 ml of medium as described and the plasmids were isolated according to the method of Birnboim and Doly (supra). A restriction analysis with the enzymes XbaI and BglII indicated that the two fragments had been linked with one another in the desired manner. These plasmids were designated pDHFR-6xHis.

Example 15

Construction of Plasmid pDHFR-2xHis

Figure 38:
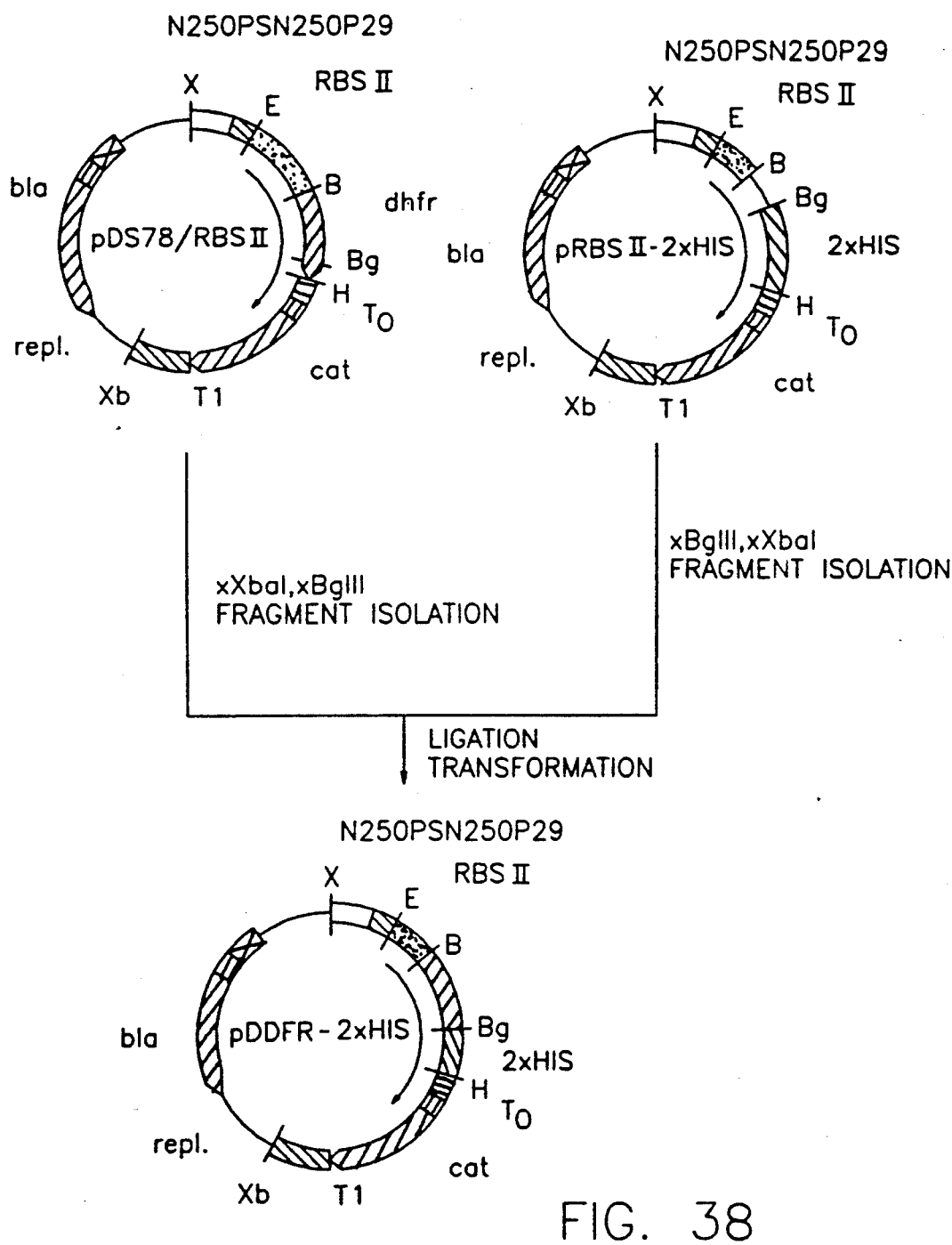

The construction of plasmid pDHFR-2xHis, which codes for the DHFR fusion protein Met-mDHFR-(His)$_2$, was carried out analogously to the construction of plasmid pDHFR-6xHis (Example 14), with the following DNA fragments being isolated and linked with each other (FIG. 38): 1) the XbaI/BglII fragment from plasmid pDS78/RBSII having the replication region, the bla gene, the promoter N25OPSN25OP29, the ribosomal binding site RBSII and the dhfr gene and 2) the BglII/XbaI fragment from plasmid pRBSII-2xHis having the region coding for 2 histidines, is the terminator $t_o$, the cat gene and the terminator T1.

Example 16

Construction of Plasmid p4xHis-DHFR-4xHis

Figure 39:
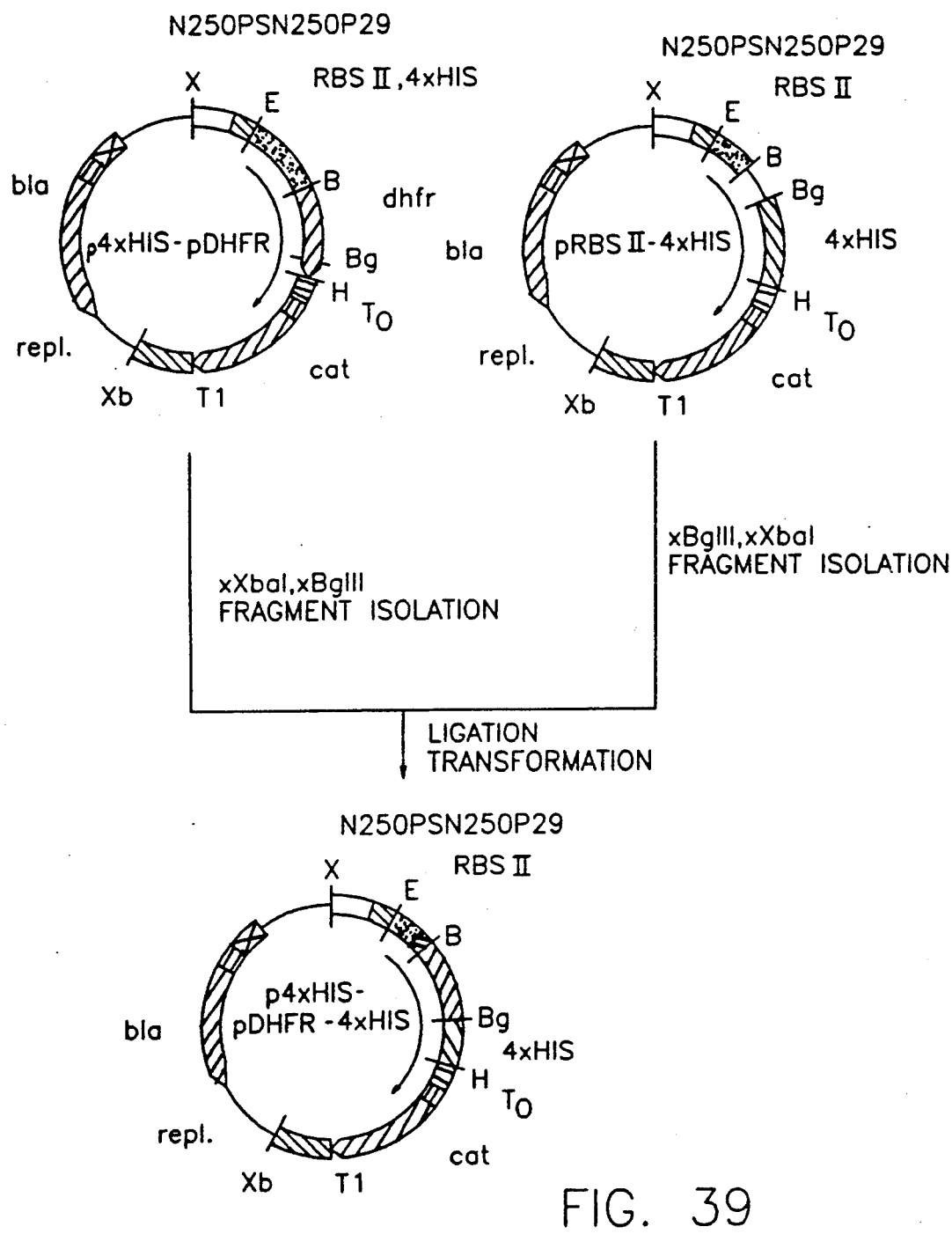

The construction of plasmid p4xHis-DHFR-4xHis, which codes for the DHFR fusion protein (His) 4-mDHFR-(His)$_4$, was carried out analogously to the construction of plasmid pDHFR-6xHis (Example 14), with the following DNA fragments being isolated and linked with each other (FIG. 39): 1) The XbaI/BglII fragment from plasmid p4xHis-DHFR having the replication region, the bla gene, the promoter N25OPSN-25OP29, the ribosomal binding site RBSII,4xHis and the dhfr gene and 2) the BglII/XbaI fragment from plasmid pRBSII-4xHis having the region coding for 4 histidines, the terminator $t_o$, the cat gene and the terminator T1.

Example 17

Preparation of the NTA Resin 41.7 g of bromoacetic acid were dissolved in 150 ml of 2 N sodium hydroxide solution and cooled to 0°. Thereto there was slowly added dropwise at 0° C. while stirring a solution of 42 g of $N^\epsilon$-Z-L-lysine in 225 ml of 2N sodium hydroxide solution. After 2 hours, the cooling was o removed and the mixture was stirred overnight. The reaction mixture was then held at 50° C. for 2 hours, and 450 ml of 1N hydrochloric acid were subsequently added. After the mixture had been cooled, the separated crystals were filtered off. The product was dissolved in 1N sodium hydroxide solution and again precipitated with the same amount of 1N hydrochloric acid and filtered off. There were obtained 40 g of N-[5-benzyloxycarbonylamino-1-carboxypentyl]-iminodiacetic acid in the form of white crystals, m.p. 172°–174° C. (dec.), $[CL]_D + 9.90°$ (c = 1; 0.1N NAOH).

7.9 g of the lysine derivative obtained were dissolved in 49 ml of 1N sodium hydroxide solution and, after the addition of a spatula tip of 5% palladium on charcoal (Pd/C). hydrogenated at room temperature and normal pressure. The catalyst was filtered off and the filtrate was evaporated. There resulted 6.2 g of N-[5-amino-1-carboxypentyl]-iminodiacetic acid whose structure, $NH_2(CH_2)_4$—CH(COOH)—N—$(CH_2COOH)_2$, was confirmed by the NMR spectrum.

100 ml of Sepharose ® (D CL-6B (Pharmacia) were washed twice on a glass suction filter with about 600 ml of water and then reacted at 30° C. for 4 hours in a 500 ml round flask with 16 ml of 4N sodium hydroxide solution and 8.22 ml of epibromohydrin. The total volume of the reaction mixture was 200 ml. The activated Sepharose was subsequently filtered off, washed neutral with water and transferred back into the reaction vessel.

6.5 g of N-[5-amino-1-carboxypentyl)-iminodiacetic acid were dissolved in 50 ml of water and added to the activated Sepharose together with 10.6 g of solid sodium carbonate. The mixture was stirred slowly at 600° C. overnight. The resulting chelate resin with the formula [Sepharose®CL-6B]—O—$CH_2$—CH(OH)—$CH_2$—NH—$(CH_2)_4$—CH(COOH)—N—$(CH_2COOH)_2$ (NTA resin) was subsequently washed in a chromatography column in succession with 500 ml of water, 100 ml of aqueous $NiSO_4.6H_2O$ (2 wt. %), 200 ml of water, 200 ml of 0.2M acetic acid (containing 0.2M NaCl and 0.1 wt./vol. % Tween 20) and 200 ml of water. The nickel ion concentration in the resulting chelate resin of the formula [Sepharose®CL-6B]—O—$CH_2$—CH(OH)—$CH_2$—NH——$(CH_2)_4$—CH(COOH)—$N(CH_2COO^-)_2Ni^{2+}$ amounted to about 7.1 micromol/ml.

Example 18

Metal Chelate Affinity Chromatography With Purified IFN-γ

A column (diameter, 1.6 cm; length, 7.0 cm) was filled with metal-free chelate resin of the formula [Sepharose ® CL-6B]—O—$CH_2$—CH(OH)—$CH_2$—NH—$(CH_2)_4$—CH(COOH)—$N(CH_2COOH)_2$ (NTA resin) and the resin was brought into the nickel form by rinsing with a three-fold column volume of 0.1M $NiSO_4.5H_2O$ and subsequently washing with a three-fold column volume of 0.2M acetic acid. The resin was subsequently equilibrated with 0.1M Tris.HCl buffer (pH 7.5) and 0.5M NaCl (throughflow in each case 60 ml/hr.).

1 mg of purified IFN-γ (Example 3, amino acid sequence see FIGS. 40A-B) was taken up in 3 ml of equilibration buffer and applied to the column. By means of enzyme immunoassay [Gallati, H., J. Clin. Chem. Clin. Biochem. 20, 907-914 (1982)] it could be detected that in spite of the two internal protein structural elements Gly-His-Ser and Ile-His-Glu no binding to the NTA column took place.

Example 19

Purification of His,His-Xa-IFN-γ By Means of NTA Resin

E. coli M15 cells containing plasmids pDMI.1 and pHis,His-Xa-IFN-γ (Example 6) were left to grow in 1 liter of LB medium containing 100 μg/ml ampicillin and 25 μg/ml kanamycin at 370° C. up to an optical density of $OD_{600}$ = 0.6. Then, IPTG was added (final concentration 0.5 mM) and the cells were incubated for a further 4 hours. Subsequently, the cells were separated (5 g wet weight) from the culture medium by centrifugation (4000 × g, 10 min. 40° C.) and extracted with 15 ml of 7M guanidine.HCl and 0.01M sodium borate (pH 8) (1 hour, 4° C., magnetic stirrer). The thus-obtained crude extract was centrifuged (10,000 × g, 151, 4° C.). the supernatant was diluted 10-fold with 0.1M Tris.HCl buffer (pH 7.5) and 0.5M NaCl, again centrifuged (10,000 × g, 15 minutes, 4° C.) and pumped up on the same NTA column as described in Example 18.

The column was subsequently washed with equilibrating buffer until the UV detector (280 nm) again showed the base value. The elution of the His,His-Xa-IFN-γ was effected by lowering the pH value to 5.5. By means of enzyme immunoassay [Gallati, H., supra] it could be detected that this protein was quantitatively absorbed on the NTA column and was eluted only by lowering the pH value. By means of SDS-polyacrylamide gel electrophoresis and RP-18 HPLC it could be detected that the protein obtained was pure His,His-Xa-IFN-γ (purity >90%). The expected amino-terminal sequence Met-His-His-Ala-Gly-Ile-Glu-Gly-Arg-Gln . . . was confirmed by Edman degradation.

Example 20

Purification of His,His-Ek-IFN-γ(-8) By Means of NTA Resin

His,His-Ek-IFN-γ(-8) (Example 7) was expressed in E. coli in an analogous manner to Example 19, extracted and purified via the NTA column. This fusion protein was also bonded to the NTA column at pH 7.5 and was eluted in pure form (purity > 90%) by lowering the pH value to 5.5. The expected sequence Met-His-His-Ala-Gly-Asp-Asp-Asp-Asp-Lys-Gln . . . was confirmed by Edman degradation.

Example 21

Purification of His,His-Xa-IFN-γ(-8)(Asn) By Means of NTA Resin

His,His-Xa-IFN-γ(-8)(Asn) (Example 8) was expressed in E. coli in an analogous manner to Example 19, extracted and purified via the NTA column. This protein was also bonded to the NTA column at pH 7.5 and was eluted in pure form (purity > 90%) by lowering the pH value to 5.5.

1 mg of the thus-obtained His-His-Xa-IFN-γ(-8)(Asn) was dialyzed against 0.1M Tris.HCl (pH 7.5), 0.5M NaCl and 1 mM $CaCl_2$. The dialysate (5 ml) was treated with 100 μl (1U) of coagulation factor Xa (Boehringer Mannheim) and incubated for 16 hours at 220° C. The enzymatic degradation of the His-His-affinity peptide was determined by means of SDS-polyacrylamide gel electrophoreses.

For the purpose of separating salts, bovine serum albumin (constituent of the commercial factor Xa preparation) and factor Xa, the incubation mixture was firstly dialyzed against water, then lyophilized and subsequently chromatographed on a RP-18 HPLC column (Nucleosil 5Cl8 column from Brownlee Labs, running agent 0.1% trifluoroacetic acid, gradient with acetonitrile, throughflow 1 ml/min). The resulting purified protein was then freed is from solvent and subjected to an Edman degradation. The expected amino-terminal sequence Gln-Asn-Pro-Tyr . . . could be confirmed by means of this method.

This experiment shows that the affinity sequence at the $NH_2$ terminus of the His-His-Xa-IFN-γ(-8)(Asn) can be cleaved off cleanly after the metal chelate affinity chromatography.

Example 22

Purification of (His)₆-mDHFR By Means of NTA Resin in 6 M Guanidine.HCl (His)₆-mDHFR (Example 9) was expressed in *E. coli* in an analogous manner to Example 19. The cells were extracted with 6M guanidine.HCl in 0.1M sodium phosphate buffer (pH 8.0) (5 ml of buffer solution per 1 g of cells, 1 hr., 22° C., magnetic stirrer). The thus-produced crude extract was subsequently centrifuged and the supernatant was pumped on to the same NTA column as described in Example 18. The chromatography was carried out analogously to Example 19 with the exception of the buffer solutions used. The buffers used contained in each case 6M guanidine.HCl in 0.1M sodium phosphate buffer having the following pH values: pH 8.0 to apply the proteins, pH 6.0 to wash-out the non-bound *E. coli* proteins and pH 4.5 in order to elute the (His)₆-mDHFR. The eluate obtained was dialyzed against water and subsequently lyophilized. By means of SDS-polyacrylamide gel electrophoresis, it was shown that the protein obtained was pure (His)₆-mDHFR (purity >90%). The expected sequence Met-Arg-Gly-Ser-His-His-His-His-His-His--Gly-Ser-Ile-Met . . . was confirmed by Edman degradation.

Example 23

Purification of (His)₄-mDHFR-(His)₄ By Means of NTA Resin in 6M Guanidine.HCl (His)₄-mDHFR-(His)₄ (Example 16) was expressed in *E. coli* in an analogous manner to Example 19, extracted and purified via the NTA column. In place of the stepwise gradients used in Example 22 there was used for the elution a linear pH gradient (pH 8.0 to pH 4.0. 2 hours). (His) 4- mDHFR-(His)4 fusion protein was eluted at pH 4.9 and had a purity of at least 90%.

Example 24

Purification of Met-mDHFR-(His) By Means of NTA Resin in 6M Urea

Met-mDHFR-(His) (Example 14) was expressed in *E. coli* in an analogous manner to Example 19. The centrifuged-off cells were extracted with 6M urea in 0.05M sodium phosphate buffer (pH 7.5) (1 g of cells per 10 ml of buffer solution) and ultrasound (10 minutes). After centrifugation of the cell debris, the supernatant was applied to a NTA column (4.5 cm × 2.6 cm) equilibrated with extraction buffer. After washing the column with extraction buffer the Met-mDHFR-(His)₆ fusion protein was eluted with a linear PH gradient of PH 7.5 (extraction buffer) to PH 4.8 (0.05M sodium phosphate buffer containing 6M urea) during 5 hours and at a pump velocity of 18 ml per hour. The fractions which contained protein were analyzed by means of SDS-polyacrylamide gel electrophoresis. 9 mg of Met-mDHFR-(His)₆ fusion protein with a purity of >90% were obtained.

Example 25

Purification of Met-mDHFR-(His)₂ By Means of NTA Resin

Met-mDHFR-(His)₂ (Example 15) was expressed in *E. coli* in an analogous manner to Example 19. The centrifuged-off cells in 0.05M potassium phosphate buffer (pH 8.0), containing 0.1M potassium chloride and 0.1% Tween 20, were treated with ultrasound in an ice bath during 15 minutes (1 g of cells per 10 ml of buffer solution). Subsequently, the cell debris were centrifuged off and the clear supernatant was placed on a NTA column (4.6 cm × 2.6 cm) equilibrated with extraction buffer. The column was washed with extraction buffer and the Met-mDHFR-(His)₂ fusion protein was eluted with a linear pH gradient of pH 8.0 (extraction buffer) to pH 5.0 (0.05M potassium phosphate buffer containing 0.1M potassium chloride and 0.1% Tween 20) during 10 hours and at a pump velocity of 50 ml per hour. The peak fractions of the eluent were analyzed by means of SDS-polyacrylamide gel electrophoresis. 7 mg of Met-mDHFR-(His)₂ fusion protein with a purity of >85% were obtained.

3 mg of the thus-obtained fusion protein Met-mDHFR-(His)₂ were dialyzed against 0.05M Tris.HCl (pH 6.0) at 60° C. The protein solution was then adjusted to pH 9.0 with 0.5M NAOH and incubated at 37° C. in the presence of 8.5 units of carboxypeptidase A from bovine pancreas (Serva, Feinbiochemica, Heidelberg BRD). After 0, 15, 30, 90 and 180 minutes, samples were removed and analyzed for their histidine content by means of HPLC. After 480 minutes the pH value was lowered to 8.0 and the reaction mixture was pumped onto an NTA column equilibrated with 0.05M potassium phosphate buffer (pH 8). The protein contained in the reaction mixture was detected in the flow-through by means of SDS-polyacrylamide gel electrophoresis. In addition, an amount of histidine residues increasing with time was detected in the samples which had been removed from the protein solution after 15, 30, 90 and 180 minutes.

This experiment shows that the affinity sequence at the carboxyl terminus can be removed cleanly after the purification on NTA resin.

What is claimed is:

1. A DNA sequence coding for a fusion protein comprising a biologically active polypeptide or protein linked by its amino- or carboxy-terminus to one or two affinity peptides, which peptides have from 2 through 6 adjacent histidine residues:

2. The DNA sequence of claim 1 in which the affinity peptides of the fusion protein have the formula:

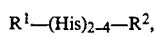

where $R^1$ is hydrogen or from 1 to about 30 amino acids; and $R^2$ is Q, Q-Ile-Glu-Gly-Arg- or Q-Asp-Asp-Asp-Asp-Lys-, where Q is a peptide bond or from 1 to about 30 amino acids.

3. A recombinant vector comprising a vector and a DNA sequence coding for a fusion protein comprising a biologically active polypeptide or protein linked by its amino- or carboxyl-terminus to one or two affinity peptides, which peptides have from two through six adjacent histidine residues, wherein the recombinant vector is capable of directing expression of the DNA sequence in a compatible unicellular host organism.

4. The recombinant vector of claim 3 in which the affinity peptides of the fusion protein have the formula:

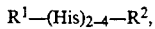

where $R^1$ is hydrogen or from 1 to about 30 amino acids; and R2 is Q, Q-Ile-Glu-Gly-Arg- or Q-Asp-Asp-Asp-Asp-Lys-, where Q is a peptide bond or from 1 to about 30 amino acids.

5. A unicellular organism containing a recombinant vector comprising a vector and a DNA sequence coding for a fusion protein comprising a biologically active polypeptide or protein linked by its amino- or carboxyl-terminus to one or two affinity peptides, which peptides have from two through six adjacent histidine residues, wherein the unicellular organism is capable of expressing the DNA sequence.

6. The unicellular organism of claim 5 which is *E. coli* strain M15.

7. A process for producing a fusion protein comprising:
   (a) culturing a unicellular organism containing a recombinant vector comprising a vector and a DNA sequence coding for a fusion protein comprising a biologically active polypeptide or protein linked by its amino- or carboxyl-terminus to one or two affinity peptides, which peptides have from two through six adjacent histidine residues, wherein the unicellular organism is capable of expressing the DNA sequence, under conditions in which the fusion protein is produced; and
   (b) isolating the fusion protein from the culture.

8. The process of claim 7 in which the fusion protein is isolated by a proc:: comprising:
   (a) contacting a lysate or extract of the unicellular organism containing the fusion is protein with a metal chelate resin of the structure:

carrier-spacer—NH—(CH$_2$)$_x$—CH(CO$_2$H)— where X is an integer from 2 to 4, under conditions in which the fusion protein binds to the resin to produce a resin-fusion protein complex;
   (b) washing the resin-fusion protein complex with a buffer to remove unbound proteins and other materials; and
   (c) eluting the bound fusion protein from the washed resin-fusion protein complex.

9. The process of claim 8 in which at least one of the links between the biologically active polypeptide or protein and the affinity peptides of the isolated fusion protein can be cleaved with a protease, and such links are cleaved after isolation by such protease.

10. The process of claim 8 in which the carrier is a beaded agarose.

11. The process of claim 8 in which the spacer is —O—CO— or —O—CH$_2$—CH(OH)—CH$_2$—.

* * * * *

UNITED STATES PATENT AND TRADEMARK OFFICE
CERTIFICATE OF CORRECTION

PATENT NO. : 5,310,663
DATED : May 10, 1994
INVENTOR(S) : Döbeli et al.

It is certified that error appears in the above-identified patent and that said Letters Patent is hereby corrected as shown below:

Column 28, line 40, Claim 1, "carboxy-terminus" should be

-- carboxyl-terminus --

Column 30, line 2, Claim 8, "proc::" should be

-- process --

Column 30, line 4, Claim 8, after "fusion" delete

-- is --

Column 30, line 8, Claim 8, after "-CH($CO_2$H)-" insert

-- N($CH_2CO_2$-)$_2$Ni$^{++}$ --

Signed and Sealed this

Sixth Day of September, 1994

Attest:

BRUCE LEHMAN

*Attesting Officer*   *Commissioner of Patents and Trademarks*